United States Patent
Sexton et al.

(10) Patent No.: US 11,739,152 B2
(45) Date of Patent: *Aug. 29, 2023

(54) ANTIBODIES WHICH BIND FC RECEPTORS (FCRN)

(71) Applicant: Takeda Pharmaceutical Company Limited, Osaka (JP)

(72) Inventors: Daniel J. Sexton, Melrose, MA (US); Christopher TenHoor, Hopkinton, MA (US); Malini Viswanathan, Acton, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 219 days.

This patent is subject to a terminal disclaimer.

(21) Appl. No.: 17/203,816

(22) Filed: Mar. 17, 2021

(65) Prior Publication Data

US 2021/0309741 A1 Oct. 7, 2021

Related U.S. Application Data

(60) Continuation of application No. 16/594,218, filed on Oct. 7, 2019, now Pat. No. 11,014,988, which is a division of application No. 15/830,998, filed on Dec. 4, 2017, now Pat. No. 10,479,834, which is a continuation of application No. 15/139,784, filed on Apr. 27, 2016, now Pat. No. 9,862,768, which is a continuation of application No. 14/122,880, filed as application No. PCT/US2012/040409 on Jun. 1, 2012, now Pat. No. 9,359,438.

(60) Provisional application No. 61/498,266, filed on Jun. 17, 2011, provisional application No. 61/492,617, filed on Jun. 2, 2011.

(51) Int. Cl.

| C07K 16/28 | (2006.01) |
| A61K 49/00 | (2006.01) |
| G01N 33/68 | (2006.01) |
| A61K 39/395 | (2006.01) |
| A61K 48/00 | (2006.01) |
| A61K 39/00 | (2006.01) |

(52) U.S. Cl.
CPC ........ C07K 16/283 (2013.01); A61K 39/3955 (2013.01); A61K 48/00 (2013.01); A61K 49/0002 (2013.01); G01N 33/6854 (2013.01); *A61K 2039/505* (2013.01); *C07K 2317/565* (2013.01); *C07K 2317/94* (2013.01)

(58) Field of Classification Search
CPC .................................................. C07K 16/283
See application file for complete search history.

(56) References Cited

U.S. PATENT DOCUMENTS

| 3,867,517 A | 2/1975 | Ling |
| 3,940,475 A | 2/1976 | Gross |
| 4,289,747 A | 9/1981 | Chu |
| 4,376,110 A | 3/1983 | David et al. |
| 4,399,216 A | 8/1983 | Axel et al. |
| 4,522,811 A | 6/1985 | Eppstein et al. |
| 4,634,665 A | 1/1987 | Axel et al. |
| 4,868,103 A | 9/1989 | Stavrianopoulos et al. |
| 5,030,002 A | 7/1991 | North, Jr. |
| 5,137,809 A | 8/1992 | Loken et al. |
| 5,179,107 A | 1/1993 | Afonso et al. |
| 5,223,409 A | 6/1993 | Ladner et al. |
| 5,225,539 A | 7/1993 | Winter |
| 5,374,548 A | 12/1994 | Caras |
| 5,399,331 A | 3/1995 | Loughrey et al. |
| 5,585,089 A | 12/1996 | Queen et al. |
| 5,627,037 A | 5/1997 | Ward et al. |
| 5,631,169 A | 5/1997 | Lakowicz et al. |
| 5,641,640 A | 6/1997 | Hanning |
| 5,658,727 A | 8/1997 | Barbas et al. |
| 5,693,761 A | 12/1997 | Queen et al. |
| 5,693,762 A | 12/1997 | Queen et al. |
| 5,849,992 A | 12/1998 | Meade et al. |
| 6,030,613 A | 2/2000 | Blumberg et al. |
| 6,086,875 A | 7/2000 | Blumberg et al. |
| 6,207,446 B1 | 3/2001 | Szostak et al. |
| 6,407,213 B1 | 6/2002 | Carter et al. |
| 6,960,178 B2 | 11/2005 | Chang et al. |
| 6,992,234 B2 | 1/2006 | Roopenian |
| 7,498,414 B2 | 3/2009 | Zhu |
| 7,662,928 B2 | 2/2010 | Balthasar et al. |
| 8,273,351 B2 | 9/2012 | TenHoor et al. |
| 8,815,246 B2 | 8/2014 | TenHoor et al. |
| 9,260,520 B2 | 2/2016 | TenHoor et al. |
| 9,359,438 B2 | 6/2016 | Sexton et al. |
| 9,862,768 B2 | 1/2018 | Sexton et al. |
| 10,479,834 B2 | 11/2019 | Sexton et al. |
| 11,014,988 B2 | 5/2021 | Sexton et al. |

(Continued)

FOREIGN PATENT DOCUMENTS

| EP | 0502 814 A2 | 9/1992 |
| EP | 2 409 991 | 1/2012 |

(Continued)

OTHER PUBLICATIONS

Paul, WE (1993) Fundamental Immunology, 3rd ed. Raven Press, NY, Chap. 9, pp. 292-295.*

(Continued)

*Primary Examiner* — Robert S Landsman

(74) *Attorney, Agent, or Firm* — Wolf, Greenfield & Sacks, P.C.

(57) ABSTRACT

The disclosure relates to antibodies that bind FcRn and methods of using these antibodies.

16 Claims, 14 Drawing Sheets

Specification includes a Sequence Listing.

(56) References Cited

U.S. PATENT DOCUMENTS

| | | | |
|---|---|---|---|
| 11,149,094 | B2 | 10/2021 | Chiu et al. |
| 2002/0138863 | A1 | 9/2002 | Roopenian |
| 2003/0070185 | A1 | 4/2003 | Jakobovits et al. |
| 2004/0005709 | A1 | 1/2004 | Hoogenboom et al. |
| 2007/0092507 | A1 | 4/2007 | Balthasar et al. |
| 2009/0123479 | A1 | 5/2009 | Bembridge et al. |
| 2009/0324614 | A1 | 12/2009 | TenHoor et al. |
| 2010/0266530 | A1 | 10/2010 | Roopenian et al. |
| 2010/0298542 | A1 | 11/2010 | Igawa et al. |
| 2013/0045218 | A1 | 2/2013 | TenHoor et al. |
| 2013/0078262 | A1 | 3/2013 | TenHoor et al. |
| 2014/0248287 | A1 | 9/2014 | TenHoor et al. |
| 2016/0194397 | A1 | 7/2016 | TenHoor et al. |
| 2016/0222108 | A1 | 8/2016 | TenHoor et al. |
| 2016/0222109 | A1 | 8/2016 | TenHoor et al. |
| 2016/0222110 | A1 | 8/2016 | TenHoor et al. |
| 2016/0222111 | A1 | 8/2016 | TenHoor et al. |
| 2016/0222112 | A1 | 8/2016 | TenHoor et al. |
| 2016/0304608 | A1 | 10/2016 | Sexton et al. |
| 2018/0305454 | A1 | 10/2018 | Sexton et al. |
| 2020/0024344 | A1 | 1/2020 | De Haard et al. |

FOREIGN PATENT DOCUMENTS

| | | |
|---|---|---|
| GB | 2 188 638 A | 10/1987 |
| JP | 2007-501847 A | 2/2007 |
| JP | 2011-501738 A | 1/2011 |
| JP | 5989159 B2 | 9/2016 |
| WO | WO 90/02809 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 96/33735 A1 | 10/1996 |
| WO | WO 96/34096 A1 | 10/1996 |
| WO | WO 98/52976 A1 | 11/1998 |
| WO | WO 99/51773 A1 | 10/1999 |
| WO | WO 1999/058572 A1 | 11/1999 |
| WO | WO 00/34317 A2 | 6/2000 |
| WO | WO 00/71694 A1 | 11/2000 |
| WO | WO 01/40803 A1 | 6/2001 |
| WO | WO 02/43658 A2 | 6/2002 |
| WO | WO 03/029456 A1 | 4/2003 |
| WO | WO 2005/013912 A2 | 2/2005 |
| WO | WO 2006/118772 | 11/2006 |
| WO | WO 2007/087289 A2 | 8/2007 |
| WO | WO 2007/092507 A2 | 8/2007 |
| WO | WO 2009/043933 A1 | 4/2009 |
| WO | WO 2009/131702 A2 | 10/2009 |
| WO | WO 2010/008051 A1 | 1/2010 |
| WO | WO 2010/070094 A1 | 6/2010 |
| WO | WO 2010/107110 A1 | 9/2010 |

OTHER PUBLICATIONS

Rudikoff, S et al. (1982) Proc. Natl. Acad. Sci. USA, 79:1979-1983 (doi: 10.1073/pnas.79.6.1979).*

Colman, PM (1994) Research in Immunology, Elsevier, NY, 145(1):33-36.*

Bendig M. M. (1995) Methods: A Companion to Methods in Enzymology, 8:83-93.*

MacCallum et al. (Oct. 11, 1996) J. Mol. Biol., 262(5):732-745. (doi: 10.1006/jmbi.1996.0548).*

Casset et al (2003) Biochemical and Biophysical Research Communications, 307:198-205. (doi:10.1016/S0006-291X(03)01131-8).*

Chen et al. (1995) EMBO J., 14(12):2784-2794. (doi: 10.1002/j.1460-2075.1995.tb07278.x).*

[No Author Listed] Therapeutic antibodies. BiotechSpain. Jan. 20, 2011. 1-7. Retrieved from https://biotechspain.com/generatepdf.cfm on Mar. 7, 2017.

Akilesh et al., The MHC class I-like Fc receptor promotes humorally mediated autoimmune disease. J Clin Invest. May 2004;113(9):1328-33.

Altschul et al., Gapped BLAST and PST-BLAST: a new generation of protein database search programs. Nucleic Acids Res. 1997;25(17):3389-3402.

Arbabi-Ghahroudi, Camelid Single-Domain Antibodies: Historical Perspective and Future Outlook. Front Immunol. Nov. 20, 2017;8:1589. doi: 10.3389/fimmu.2017.01589. eCollection 2017.

Berge et al., Review Article—Pharmaceutical Salts. J. Pharm. Sci. Jan. 1977;66:1-19.

Bergthorsdottir et al. Signals that Initiate Somatic Hypermutation of B Cells In Vitro. J. Immunol. 2001;166:2228-2234.

Bird et al., Single-Chain Antigen-Binding Proteins. Science. Oct. 1988. 21;242:423-426.

Bowie et al., Deciphering the Message in Protein Sequences: Tolerance to Amino Acid Substitutions. Science. Mar. 1990;247:1306-1310.

Brorson et al., Mutational analysis of avidity and fine specificity of anti-levan antibodies. J Immunol. Dec. 15, 1999;163(12):6694-701.

Brummell et al., Probing the combining site of an anti-carbohydrate antibody by saturation-mutagenesis: role of the heavy-chain CDR3 residues. Biochemistry. Feb. 2, 1993;32(4): 1180-7.

Buckley, 27. Transplantation immunology: organ and bone marrow. J Allergy Clin Immunol. Feb. 2003;111(2 Suppl):S733-44. doi: 10.1067/mai.2003.142.

Burks et al., In vitro scanning saturation mutagenesis of an antibody binding pocket. Proc Natl Acad Sci U S A. Jan. 21, 1997;94(2):412-7.

Burmeister et al: "Crystal structure of the complex of rat neonatal Fc receptor with Fc," Nature, 372, 379-383, Nov. 24, 1994.

Casset et al., A peptide mimetic of an anti-CD4 monoclonal antibody by rational design. Biochem Biophys Res Commun. Jul. 18, 2003;307(1):198-205.

Cauza et al., Expression of FcRn, the MHC class I-related receptor for IgG, in human keratinocytes. J Invest Dermatol. Jan. 2005;124(l):132-9.

Chen et al., Selection and analysis of an optimized anti-VEGF antibody: crystal structure of an affinity-matured Fab in complex with antigen. J Mol Biol. Nov. 5, 1999;293(4):865-81.

Chothia et al., Canonical Structures for the Hypervariable Regions of Immunoglobulins. J. Mol. Biol. 1987;196:901-917.

Clackson et al., Making antibody fragments using phage display libraries. Nature. Aug. 1991; 352:624-628.

Colcher et al., [76] Use of Monoclonal Antibodies as Radiopharmaceuticals for the Localization of Human Carcinoma Xenografts in Athymic Mice. Meth. Enzymol. 1986; 121:802-816.

Colman, Effects of amino acid sequence changes on antibody-antigen interactions. Res Immunol. Jan. 1994;145(1):33-6.

Cook et al., The human immunoglobulin VH repertoire. Immunol. Today. 1995;16(5):237-242.

Costagliola et al., Genetic Immunization Against the Human Thyroiditis and Allows Production of Monoclonal Antibodies Recognizing the Native Receptor. J. Immunology. 1998;160:1458-1465.

Dall' Acqua et al., Increasing the affinity of a human IgG1 for the neonatal Fc receptor: biological consequences. J Immunol. Nov. 1, 2002;169(9):5171-80.

De Haard et al., A Large Non-immunized Human Fab Fragment Phage Library That Permits Rapid Isolation and Kinetic Analysis of High Affinity Antibodies. J. Biol. Chem. 1999;274:18218-18230.

De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.

De Wildt et al., "Antibody arrays for high-throughput screening of antibody-antigen interactions", Nat. Biotechnol., 2000, vol. 18: pp. 989-994.

Dick Jr. et al., C-Terminal lysine variants in fully human monoclonal antibodies: investigation of test methods and possible causes. Biotechnology and Bioengineering. Aug. 2008;100:1132-1143 (available online at—DOI 10.1002/bit.21855).

(56) References Cited

OTHER PUBLICATIONS

Doria-Rose et al., Strategies to guide the antibody affinity maturation process. Curr Opin Virol. Apr. 2015;11:137-47. doi: 10.1016/j.coviro.2015.04.002. Epub Apr. 24, 2015.
Gershoni et al., Epitope mapping: the first step in developing epitope-based vaccines. BioDrugs. 2007;21(3):145-56. doi: 10.2165/00063030-200721030-00002.
Getman et al., Pharmacokinetic effects of 4C9, an anti-FcRn antibody, in rats: implications for the use of FcRn inhibitors for the treatment of humoral autoimmune and alloimmune conditions. J Pharm Sci. Apr. 2005;94(4):718-29.
Gram et al., In vitro selection and affinity maturation of antibodies from a naive combinatorial immunoglobulin library. PNAS USA. 1992;89:3576-3580.
Green et al., Antigen-specific human monoclonal antibodies from mice engineered with human Ig heavy and light chain YACs. Nature Genetics. May 1994;7:13-21.
Greenwood et al., The Preparation of 131I-Labelled Human Growth Hormone of High Specific Radioactivity. Biochem. J. 1963;89:114-123.
Hanes et al., [24] Selecting and Evolving Functional Proteins in Vitro by Ribosome Display. Methods Enzymol. 2000;328:404-430.
Hanes et al., Picomolar affinity antibodies from a fully synthetic naive library selected and evolved by ribosome display. Nat. Biotechnol. 2000;18:1287-1292.
Hawkins et al., Selection of Phage Antibodies by Affinity Mimicking Affinity Maturation. J. Mol. Biol. 1992;226:889-896.
Hinton et al., Engineered human IgG antibodies with longer serum half-lives in primates. J Biol Chem. Feb. 20, 2004;279(8):6213-6. Epub Dec 29, 2003.
Hnatowich et al., The Preparation of DTPA-Coupled Antibodies Radiolabeled with Metallic Radionuclides: an Improved Method. J. Immunol. Methods. 1983;65:147-157.
Holm et al., Functional mapping and single chain construction of the anti-cytokeratin 8 monoclonal antibody TS1. Mol Immunol. Feb. 2007;44(6):1075-84. Epub Sep. 20, 2006.
Hoogenboom et al., Antibody phage display technology and its applications. Immunotechnology. 1998;4:1-20.
Hoogenboom et al., Natural and designer binding sites made by phage display technology. Immunol. Today. 2000;2(8):371-378.
Hunter et al., Preparation of Iodine-131 Labelled Human Growth Hormone of High Specific Activity. Nature. May 1962; 194:495-496.
Huse et al., Generation of a Large Combinatorial Library of the Immunoglobulin Repertoire in Phage Lambda. Science. Dec. 8, 1989;246:1275-1281.
Huston et al., Protein engineering of antibody binding sites: Recovery of specific activity in an anti-digoxin single-chain Fv analogue produced in *Escherichia coli*. Proc. Natl. Acad. Sci. USA. 1988;85:5879-5883.
Igawa et al., Engineering the variable region of therapeutic IgG antibodies. MAbs. May-Jun. 2011;3(3):243-52. Epub May 1, 2011.
Israel et al., Expression of the neonatal Fc receptor, FcRn, on human intestinal epithelial cells. Immunology. 1997;92:69-74.
Janeway et al., The interaction of the antibody molecule with specific antigen. Immunobiology: The Immune System in Health and Disease.5th edition. New York: Garland Science; 2001. NCBI Bookshelf. 5 pages.
Jang et al., The structural basis for DNA binding by an anti-DNA autoantibody. Mol Immunol. Dec. 1998;35(18): 1207-17.
Jefferis et al., Icg-Fc-mediated effector functions: molecular definition of interaction sites for effector ligands and the role of glycosylation. Immunol. Rev. 1998;163:59-76.
Jones et al., Replacing the complementarity-determining regions in a human antibody with those from a mouse. Nature. May 29, 1986-Jun. 4;321(6069):522-5.
Jordan et al., Desensitization therapy with intravenous gammaglobulin (IVIG): applications in solid organ transplantation. Trans Am Clin Climatol Assoc. 2006;117:199-211; discussion 211.
Jowett et al., Defining Relapse of Ulcerative Colitis Using a Symptom-based Activity Index. Scan. J. Gastroenterol. 2003;38(2): 164-171.
Junghans et al., Finally! The Brambell Receptor (FcRB). Immunologic Research. 1997;16(1):29-57.
Junghans et al., The protection receptor for IgG catabolism is the B2-microglobulin-containing neonatal intestinal transport receptor. Proc. Natl. Acad. Sci. USA. May 1996;93:5512-5516.
Karlin et al., Methods for assessing the statistical significance of molecular sequence features by using general scoring schemes. Proc. Natl. Acad. Sci. USA. Mar. 1990;87:2264-2268.
Karlin et al., Applications and statistics for multiple high-scoring segments in molecular sequences. Proc. Natl. Acad. Sci. USA. Jun. 1993; 90:5873-5877.
Khatri et al., Effect of plasma exchange in accelerating natalizumab clearance and restoring leukocyte function. Neurology. Feb. 3, 2009;72(5):402-9.
Kobayashi et al., FcRn-mediated transcytosis of immunoglobulin G in human renal proximal tubular epithelial cells, Am J Physiol Renal Physiol 282:F358 (2002).
Kobayashi et al., Tryptophan H33 plays an important role in pyrimidine (6-4) pyrimidone photoproduct binding by a high-affinity antibody. Protein Eng. Oct. 1999;12(10):879-84.
Leach et al., Isolation from Human Placenta of the IgG Transporter, FcRn, and Localization to the Syncytiotrophoblast. The American Journal of Immunology. 1996;157: 3317-3322.
Levi et al., A complementarity-determining region synthetic peptide acts as a miniantibody and neutralizes human immunodeficiency virus type 1 in vitro. Proc Natl Acad Sci U S A. May 15, 1993;90(10):4374-8.
Li et al., Complete FcRn dependence for intravenous Ig therapy in autoimmune skin blistering diseases, J Clin Invest 115:3440-3450 (2005).
Liu et al., Amelioration of experimental autoimmune myasthenia gravis in rats by neonatal FcR blockade. J Immunol. Apr. 15, 2007;178(8):5390-8.
Liu et al., Heterogeneity of Monoclonal Antibodies. Journal of Pharmaceutical Sciences. Jul. 2008;97(7):2426-2447.
Lueking et al., Protein Microarrays for Gene Expression and Antibody Screening, Anal. Biochem. 1999;270:103-111.
Macbeath, et al., Printing Proteins as Microarrays for High-Throughput Function Determination. Science. Sep. 2000;289:1760-1763.
MacCallum et al., Antibody-antigen interactions: contact analysis and binding site topography. J Mol Biol. Oct. 11, 1996;262(5):732-45.
MacLennan, Germinal centers. Annu Rev Immunol. 1994;12:117-39.
Marchalonis, An Enzymic Method for the /Trace Iodination of Immunoglobulins and other Proteins. Biochem. J. 1969;113:299-305.
Margolies et al., Diversity of light chain variable region sequences among rabbit antibodies elicited by the same antigens. Proc Natl Acad Sci U S A. Jun. 1975;72(6):2180-4.
Mattheakis et al., An in vitro polysome display system for identifying ligands from very large peptide libraries. Proc. Natl. Acad. Sci. USA. Sep. 1994; 91:9022-9026.
Meredith et al., Intraperitoneal Radioimmunotherapy of Ovarian Cancer with Lutetium-177-CC49. J. Nucl. Med. 1996;37:1491-1496.
Morrison et al., Use of Lactoperoxidase Catalyzed Iodination in Immunochemical Studies. Immunochemistry. 1971;8:289-297.
Morrison, Transfectomas Provide Novel Chimeric Antibodies. Science. 1985;229:1202-1207.
Nixon et al., Fully human monoclonal antibody inhibitors of the neonatal Fc receptor reduce circulating IgG in non-human primates. Frontiers in Immunology. Apr. 23, 2015;6(Article 176):1-13.
Onuma et al., Generation of a humanized monoclonal antibody against human parathyroid hormone-related protein and its efficacy against humoral hypercalcemia of malignancy. Anticancer Res. Sep.-Oct. 2004;24(5A):2665-73.

(56) References Cited

OTHER PUBLICATIONS

Poser, et al., New Diagnostic Criteria for Multiple Sclerosis: Guidelines for Research Protocols. Ann. Neurol. Mar. 1983;13(3):227-231.
Powers, et al., Expression of single-chain Fv-Fc Fusions in Pichia pastoris, J. Immunol. Methods. 2001;251:123-35.
Raghavan et al., Analysis of the pH dependence of the neonatal Fc receptor/immunoglobulin G interaction using antibody and receptor variants. Biochemistry. Nov. 14, 1995;34(45):14649-57.
Raghavan et al., Investigation of the interaction between the class I MHC-related Fc receptor and its immunoglobulin G ligand. Immunity. Jul. 1994;1(4):303-15. doi: 10.1016/1074-7613(94)90082-5.
Ranade, Drug Delivery Systems, 1, Site-Specific Drug Delivery Using Liposomes as Carriers. J. Clin. Pharmacol. 1989;29:685-694.
Roopenian et al., FcRn: the neonatal Fc receptor comes of age. Nat Rev Immunol. Sep. 2007;7(9):715-25. Epub Aug. 17, 2007.
Roopenian et al., The MHC Class I-Like IgG Receptor Controls Perinatal IgG Transport, IgG Homeostasis, and Fate of IgG-Fc-Coupled Drugs. The Journal of Immunology. 2003;170:3528-3533.
Roskos et al., Molecular Engineering II: Antibody Affinity. Handbook of Therapeutic Antibodies. 2007:145-169.
Rudikoff et al., Single amino acid substitution altering antigen-binding specificity. Proc Natl Acad Sci U S A. Mar. 1982;79(6):1979-83.
Saldanha, Molecular Engineering I: Humanization. Handbook of Therapeutic Antibodies, Chapter 6. 2007:119-144.
Sesarman et al., The neonatal Fc receptor as therapeutic target in IgG-mediated autoimmune diseases. Cell. Mol. Life Sci. 2010; 67( 15):2533-2550.
Stuve et al., Potential risk of progressive multifocal leukoencephalopathy with natalizumab therapy: possible interventions. Arch Neurol. Feb. 2007;64(2):169-76. doi: 10.1001/archneur.64.2.169.
Torres et al., The immunoglobulin constant region contributes to affinity and specificity. Trends Immunol. Feb. 2008;29(2):91-7. doi:10.1016/j.it.2007.11.004. Epub Jan. 10, 2008.
Vajdos et al., Comprehensive functional maps of the antigen-binding site of an anti-ErbB2 antibody obtained with shotgun scanning mutagenesis. J Mol Biol. Jul. 5, 2002;320(2):415-28.
Wark et al., Latest technologies for the enhancement of antibody affinity. Adv Drug Deliv Rev. Aug. 7, 2006;58(5-6):657-70.
Wu et al., Humanization of a murine monoclonal antibody by simultaneous optimization of framework and CDR residues. J Mol Biol. Nov. 19, 1999;294(1):151-62.
Xu et al., Diversity in the CDR3 region of V(H) is sufficient for most antibody specificities. Immunity. Jul. 2000;13(1):37-45.
Yu et al., Mechanism of intravenous immune globulin therapy in antibody-mediated autoimmune diseases. N Engl J Med. Jan. 21, 1999;340(3):227-8.
Zhu et al., MHC class I-related neonatal Fc receptor for IgG is functionally expressed in monocytes, intestinal macrophages, and dendritic cells. J Immunol. Mar. 1, 2001;166(5):3266-76.
Zhu et al., The heavy chain of neonatal Fc receptor for IgG is sequestered in endoplasmic reticulum by forming oligomers in the absence of beta2-microglobulin association. Biochem J. Nov. 1, 2002;367(Pt 3):703-14.
Akbar et al., A compact vocabulary of paratope-epitope interactions enables predictability of antibody-antigen binding. Cell Rep. Mar. 16, 2021;34(11):108856(1-15). doi: 10.1016/j.celrep.2021.108856. Supplementary Information, 29 pages.
Arons et al., Immunoglobulin light chain repertoire in hairy cell leukemia. Leuk Res. Sep. 2007;31(9):1231-6. doi: 10.1016/j.leukres. 2006.11.019. Epub Apr. 25, 2007.
Kolker D., Antibodies and the written description requirement of 35 U.S.C. 112(a). Presentation at the USPTO Biotechnology Chemical Pharmaceutical Customer Partnership Meeting, Sep. 17, 2020, 36 pages.
Lo et al., Conformational epitope matching and prediction based on protein surface spiral features. BMC Genomics. May 31, 2021;22(Suppl 2):116(1-16). doi: 10.1186/s12864-020-07303-5.
Marks et al., How repertoire data are changing antibody science. J Biol Chem. Jul. 17, 2020;295(29):9823-9837. doi: 10.1074/jbc. REV120.010181. Epub May 14, 2020.
Vajda et al., Progress toward improved understanding of antibody maturation. Curr Opin Struct Biol. Apr. 2021;67:226-231. doi: 10.1016/j.sbi.2020.11.008. Epub Feb. 17, 2021.

\* cited by examiner

```
              FR1-L                      CDR1-L              FR2-L              CDR2-L
DX-2504:     QSALTQPASVSGSPGQSITISC TGTGSDVGSYNLVS WYQQHPGKAPKLMIY GDSQRPS

532A-X53-C02 QSALTQPASVSGSPGQSITISC TGTGSDVGSYNLVS WYQQHPGKAPKLMIY GDSQRPS

532A-X54-B03 QSALTQPASVSGSPGQSITISC TGTGSDVGSYNLVS WYQQHPGKAPKLMIY GDSQRPS

FR3-L                          CDR3-L        FR4-L
DX-2504:     GVSNRFSGSKSGNTASLTISGLQAEDEADYYC CSYAGSGIYV FGTGTKVTVL

532A-X53-C02 GVSNRFSGSKSGNTASLTISGLQAEDEADYYC SSYAGSGIYV FGTGTKVTVL

532A-X54-B03 GVSNRFSGSKSGNTASLTISGLQAEDEADYYC ASYAGSGIYV FGTGTKVTVL
```

Figure 9

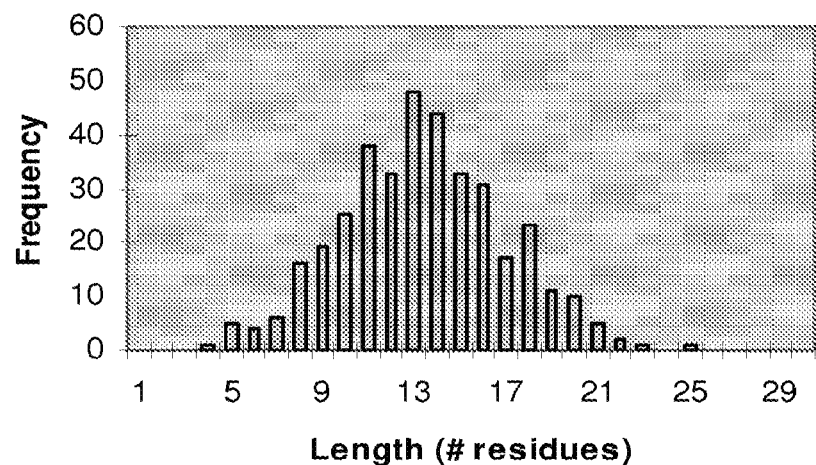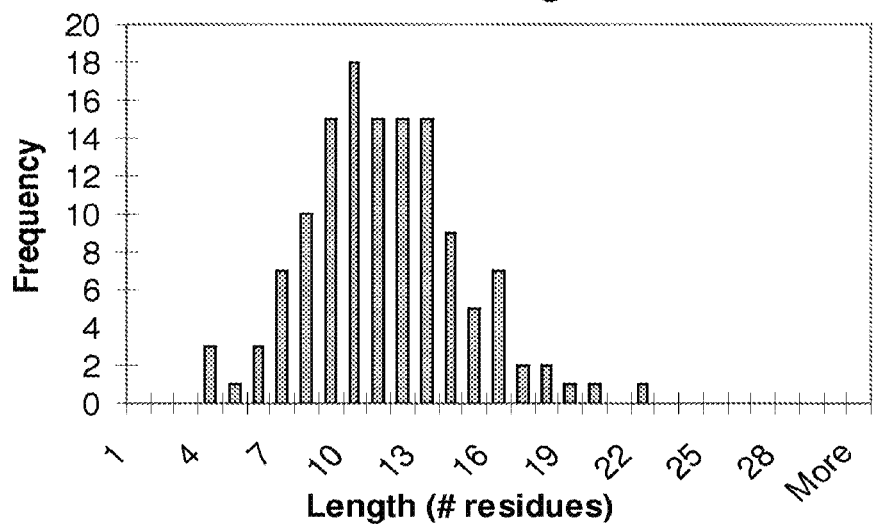
Figure 10

SEQUENCE LISTING

<160> NUMBER OF SEQ ID NOS: 26

<210> SEQ ID NO 1
<211> LENGTH: 365
<212> TYPE: PRT
<213> ORGANISM: H. sapiens

<400> SEQUENCE: 1

Met Gly Val Pro Arg Pro Gln Pro Trp Ala Leu Gly Leu Leu Leu Phe

```
                1               5                      10                          15
        Leu Leu Pro Gly Ser Leu Gly Ala Glu Ser His Leu Ser Leu Leu Tyr
                        20                      25                      30

His Leu Thr Ala Val Ser Ser Pro Ala Pro Gly Thr Pro Ala Phe Trp
                        35                      40                      45

Val Ser Gly Trp Leu Gly Pro Gln Gln Tyr Leu Ser Tyr Asn Ser Leu
                        50                      55                      60

Arg Gly Glu Ala Glu Pro Cys Gly Ala Trp Val Trp Glu Asn Gln Val
         65                      70                      75                      80

Ser Trp Tyr Trp Glu Lys Glu Thr Thr Asp Leu Arg Ile Lys Glu Lys
                                85                      90                      95

Leu Phe Leu Glu Ala Phe Lys Ala Leu Gly Lys Gly Pro Tyr Thr
                        100                     105                     110

Leu Gln Gly Leu Leu Gly Cys Glu Leu Gly Pro Asp Asn Thr Ser Val
                        115                     120                     125

Pro Thr Ala Lys Phe Ala Leu Asn Gly Glu Glu Phe Met Asn Phe Asp
                        130                     135                     140

Leu Lys Gln Gly Thr Trp Gly Gly Asp Trp Pro Glu Ala Leu Ala Ile
        145                     150                     155                     160

Ser Gln Arg Trp Gln Gln Asp Lys Ala Ala Asn Lys Glu Leu Thr
                        165                     170                     175

Phe Leu Leu Phe Ser Cys Pro His Arg Leu Arg Glu His Leu Glu Arg
                        180                     185                     190

Gly Arg Gly Asn Leu Glu Trp Lys Glu Pro Pro Ser Met Arg Leu Lys
                        195                     200                     205

Ala Arg Pro Ser Ser Pro Gly Phe Ser Val Leu Thr Cys Ser Ala Phe
        210                     215                     220

Ser Phe Tyr Pro Pro Glu Leu Gln Leu Arg Phe Leu Arg Asn Gly Leu
        225                     230                     235                     240

Ala Ala Gly Thr Gly Gln Gly Asp Phe Gly Pro Asn Ser Asp Gly Ser
                        245                     250                     255

Phe His Ala Ser Ser Ser Leu Thr Val Lys Ser Gly Asp Glu His His
                        260                     265                     270

Tyr Cys Cys Ile Val Gln His Ala Gly Leu Ala Gln Pro Leu Arg Val
                        275                     280                     285

Glu Leu Glu Ser Pro Ala Lys Ser Ser Val Leu Val Val Gly Ile Val
                        290                     295                     300

Ile Gly Val Leu Leu Leu Thr Ala Ala Ala Val Gly Ala Leu Leu
        305                     310                     315                     320

Trp Arg Arg Met Arg Ser Gly Leu Pro Ala Pro Trp Ile Ser Leu Arg
                        325                     330                     335

Gly Asp Asp Thr Gly Val Leu Leu Pro Thr Pro Gly Glu Ala Gln Asp
                        340                     345                     350

Ala Asp Leu Lys Asp Val Asn Val Ile Pro Ala Thr Ala
                        355                     360                     365

<210> SEQ ID NO 2
<211> LENGTH: 366
<212> TYPE: PRT
<213> ORGANISM: R. Rattus

<400> SEQUENCE: 2

Met Gly Met Ser Gln Pro Gly Val Leu Leu Ser Leu Leu Leu Val Leu
        1               5                      10                          15
```

Leu Pro Gln Thr Trp Gly Ala Glu Pro Arg Leu Pro Leu Met Tyr His
            20                  25                  30

Leu Ala Ala Val Ser Asp Leu Ser Thr Gly Leu Pro Ser Phe Trp Ala
        35                  40                  45

Thr Gly Trp Leu Gly Ala Gln Gln Tyr Leu Thr Tyr Asn Asn Leu Arg
    50                  55                  60

Gln Glu Ala Asp Pro Cys Gly Ala Trp Ile Trp Glu Asn Gln Val Ser
65                  70                  75                  80

Trp Tyr Trp Glu Lys Glu Thr Thr Asp Leu Lys Ser Lys Glu Gln Leu
                85                  90                  95

Phe Leu Glu Ala Ile Arg Thr Leu Glu Asn Gln Ile Asn Gly Thr Phe
            100                 105                 110

Thr Leu Gln Gly Leu Leu Gly Cys Glu Leu Ala Pro Asp Asn Ser Ser
        115                 120                 125

Leu Pro Thr Ala Val Phe Ala Leu Asn Gly Glu Glu Phe Met Arg Phe
    130                 135                 140

Asn Pro Arg Thr Gly Asn Trp Ser Gly Glu Trp Pro Glu Thr Asp Ile
145                 150                 155                 160

Val Gly Asn Leu Trp Met Lys Gln Pro Glu Ala Ala Arg Lys Glu Ser
                165                 170                 175

Glu Phe Leu Leu Thr Ser Cys Pro Glu Arg Leu Leu Gly His Leu Glu
            180                 185                 190

Arg Gly Arg Gln Asn Leu Glu Trp Lys Glu Pro Pro Ser Met Arg Leu
        195                 200                 205

Lys Ala Arg Pro Gly Asn Ser Gly Ser Ser Val Leu Thr Cys Ala Ala
    210                 215                 220

Phe Ser Phe Tyr Pro Pro Glu Leu Lys Phe Arg Phe Leu Arg Asn Gly
225                 230                 235                 240

Leu Ala Ser Gly Ser Gly Asn Cys Ser Thr Gly Pro Asn Gly Asp Gly
                245                 250                 255

Ser Phe His Ala Trp Ser Leu Leu Glu Val Lys Arg Gly Asp Glu His
            260                 265                 270

His Tyr Gln Cys Gln Val Glu His Glu Gly Leu Ala Gln Pro Leu Thr
        275                 280                 285

Val Asp Leu Asp Ser Pro Ala Arg Ser Ser Val Pro Val Val Gly Ile
    290                 295                 300

Ile Leu Gly Leu Leu Leu Val Val Val Ala Ile Ala Gly Gly Val Leu
305                 310                 315                 320

Leu Trp Asn Arg Met Arg Ser Gly Leu Pro Ala Pro Trp Leu Ser Leu
                325                 330                 335

Ser Gly Asp Asp Ser Gly Asp Leu Leu Pro Gly Gly Asn Leu Pro Pro
            340                 345                 350

Glu Ala Glu Pro Gln Gly Val Asn Ala Phe Pro Ala Thr Ser
        355                 360                 365

<210> SEQ ID NO 3
<211> LENGTH: 119
<212> TYPE: PRT
<213> ORGANISM: H. sapiens

<400> SEQUENCE: 3

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
                100                 105                 110

Val Lys Trp Asp Arg Asp Met
        115

<210> SEQ ID NO 4
<211> LENGTH: 119
<212> TYPE: PRT
<213> ORGANISM: R. Rattus

<400> SEQUENCE: 4

Met Ala Arg Ser Val Thr Val Ile Phe Leu Val Leu Val Ser Leu Ala
1               5                   10                  15

Val Val Leu Ala Ile Gln Lys Thr Pro Gln Ile Gln Val Tyr Ser Arg
                20                  25                  30

His Pro Pro Glu Asn Gly Lys Pro Asn Phe Leu Asn Cys Tyr Val Ser
        35                  40                  45

Gln Phe His Pro Pro Gln Ile Glu Ile Glu Leu Leu Lys Asn Gly Lys
        50                  55                  60

Lys Ile Pro Asn Ile Glu Met Ser Asp Leu Ser Phe Ser Lys Asp Trp
65                  70                  75                  80

Ser Phe Tyr Ile Leu Ala His Thr Glu Phe Thr Pro Thr Glu Thr Asp
                85                  90                  95

Val Tyr Ala Cys Arg Val Lys His Val Thr Leu Lys Glu Pro Lys Thr
                100                 105                 110

Val Thr Trp Asp Arg Asp Met
        115

<210> SEQ ID NO 5
<211> LENGTH: 1510
<212> TYPE: DNA
<213> ORGANISM: H. sapiens

<400> SEQUENCE: 5
gttcttcagg tacgaggagg gcattgttgt cagtctggac cgagcccgca gagcccctcc      60
tcggcgtcct ggtcccggcc gtgcccgcgg tgtcccggga ggaaggggcg ggccgggggt     120
cgggaggagt cacgtgcccc ctcccgcccc aggtcgtcct ctcagcatgg gggtcccgcg     180
gcctcagccc tggcgctggg gctcctgct ctttctcctt cctgggagcc tgggcgcaga     240
aagccacctc tccctcctgt accaccttac gcgggtgtcc tcgcctgccc cggggactcc     300
tgccttctgg gtgtccggct ggctgggccc gcagcagtac ctgagctaca atagcctgcg     360
gggcgaggcg gagccctgtg agcttgggt ctggaaaaac caggtgtcct ggtattggga     420
gaaagagacc acagatctga ggatcaagga gaagctcttt ctggaagctt tcaaagcttt     480 gggggaaaa ggtccctaca ctctgcaggg cctgctgggc tgtgaactgg ccctgacaa      540 cacctcggtg cccaccgcca agttcgccct gaacggcgag gagttcatga atttcgacct     600

-continued

| | |
|---|---|
| caagcagggc acctggggtg gggactggcc cgaggccctg gctatcagtc agcggtggca | 660 |
| gcagcaggac aaggcggcca acaaggagct caccttcctg ctattctcct gcccgcaccg | 720 |
| cctgcgggag cacctggaga ggggccgcgg aaacctggag tggaaggagc cccctccat | 780 |
| gcgcctgaag gcccgaccca gcagccctgg cttttccgtg cttacctgca gcgccttctc | 840 |
| cttctacccc tccggagctgc aacttcggtt cctgcggaat gggctggccg ctggcaccgg | 900 |
| ccagggtgac ttcggcccca acagtgacgg atccttccac gcctcgtcgt cactaacagt | 960 |
| caaaagtggc gatgagcacc actactgctg cattgtgcag cacgcggggc tggcgcagcc | 1020 |
| cctcagggtg gagctggaat ctccagccaa gtcctccgtg ctcgtggtgg gaatcgtcat | 1080 |
| cggtgtcttg ctactcacgg cagcggctgt aggaggagct ctgttgtgga aaggatgag | 1140 |
| gagtgggctg ccagccccctt ggatctccct tcgtggagac gacaccgggg tcctcctgcc | 1200 |
| caccccaggg gaggcccagg atgctgattt gaaggatgta aatgtgattc cagccaccgc | 1260 |
| ctgaccatcc gccattccga ctgctaaaag cgaatgtagt caggccccctt tcatgctgtg | 1320 |
| agacctcctg gaacactggc atctctgagc tccagaagg ggttctgggc ctagttgtcc | 1380 |
| tccctctgga gccccgtcct gtggtctgcc tcagttccc ctcctaatac atatggctgt | 1440 |
| tttccacctc gataatataa aacgagtttg ggcccgaaaa aaaaaaaaaa aaaaaaaaaa | 1500 |
| aaaaaaaaaa | 1510 |

<210> SEQ ID NO 6
<211> LENGTH: 984
<212> TYPE: DNA
<213> ORGANISM: H. sapiens

<400> SEQUENCE: 6

| | |
|---|---|
| atggggtcc cgcggcctca gccctgggcg ctggggctcc tgctcttct ccttcctggg | 60 |
| agcctgggcg cagaaagcca cctctccctc ctgtaccacc ttaccgcggt gtcctcgcct | 120 |
| gccccgggga ctcctgcctt ctgggtgtcc ggctggctgg gccgcagca gtacctgagc | 180 |
| tacaatagcc tgcggggcga ggcggagccc tgtggagctt gggtctggga aaaccaggtg | 240 |
| tcctggtatt gggagaaaga gaccacagat ctgaggatca aggagaagct cttctctggaa | 300 |
| gctttcaaag ctttgggggg aaaaggtccc tacactctgc agggcctgct gggctgtgaa | 360 |
| ctgggccctg acaacacctc ggtgcccacc gccaagttcg ccctgaacgg cgaggagttc | 420 |
| atgaatttcg acctcaagca gggcacctgg ggtggggact ggcccgaggc cctggctatc | 480 |
| agtcagcggt ggcagcagca ggacaaggcg ccaacaagg agctcacctt cctgctattc | 540 |
| tcctgcccgc accgctgcg ggagcacctg gagaggggcc gcggaaacct ggagtggaag | 600 |
| gagcccccct ccatgcgcct gaaggcccga cccagcagcc ctggcttttc cgtgcttacc | 660 |
| tgcagcgcct tctccttcta ccctccggag ctgcaacttc ggttcctgcg gaatgggctg | 720 |
| gccgctggca ccggccaggg tgacttcggc cccaacagtg acggatcctt ccacgcctcg | 780 |
| tcgtcactaa cagtcaaaag tggcgatgag caccactact gctgcattgt gcagcacgcg | 840 |
| gggctggcgc agcccctcag ggtggagctg aatctccag ccaagtcctc ccggccgctc | 900 |
| gacgggctac gagcatcagt aacactacta ggcgcaggcc tactactatc actactacca | 960 |
| gcactactac gatttgggcc ataa | 984 |

<210> SEQ ID NO 7
<211> LENGTH: 987
<212> TYPE: DNA
<213> ORGANISM: H. sapiens

<400> SEQUENCE: 7

```
aatataagtg aggcgtcgc gctggcgggc attcctgaag ctgacagcat tcgggccgag      60
atgtctcgct ccgtggcctt agctgtgctc gcgctactct ctctttctgg cctggaggct    120
atccagcgta ctccaaagat tcaggtttac tcacgtcatc cagcagagaa tggaaagtca    180
aatttcctga attgctatgt gtctgggttt catccatccg acattgaagt tgacttactg    240
aagaatggag agagaattga aaagtggag cattcagact tgtctttcag caaggactgg    300
tctttctatc tcttgtacta cactgaattc accccccactg aaaaagatga gtatgcctgc    360
cgtgtgaacc atgtgacttt gtcacagccc aagatagtta agtgggatcg agacatgtaa    420
gcagcatcat ggaggtttga agatgccgca tttggattgg atgaattcca aattctgctt    480
gcttgctttt taatattgat atgcttatac acttacactt tatgcacaaa atgtagggtt    540
ataataatgt taacatggac atgatcttct ttataattct actttgagtg ctgtctccat    600
gtttgatgta tctgagcagg ttgctccaca ggtagctcta ggagggctgg caacttagag    660
gtggggagca gagaattctc ttatccaaca tcaacatctt ggtcagattt gaactcttca    720
atctcttgca ctcaaagctt gttaagatag ttaagcgtgc ataagttaac ttccaattta    780
catactctgc ttagaatttg ggggaaaatt tagaaatata attgacagga ttattggaaa    840
tttgttataa tgaatgaaac attttgtcat ataagattca tatttacttc ttatacattt    900
gataaagtaa ggcatggttg tggttaatct ggtttatttt tgttccacaa gttaaataaa    960
tcataaaact tgatgtgtta tctctta                                        987
```

<210> SEQ ID NO 8
<211> LENGTH: 110
<212> TYPE: PRT
<213> ORGANISM: Artificial sequence
<220> FEATURE:
<223> OTHER INFORMATION: Light chain variable region for DX-2504

<400> SEQUENCE: 8

```
Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Gly Asp Ser Gln Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Gly Ile Tyr Val Phe Gly Thr Gly Thr Lys Val Thr Val Leu
            100                 105                 110
```

<210> SEQ ID NO 9
<211> LENGTH: 116
<212> TYPE: PRT
<213> ORGANISM: Artificial sequence
<220> FEATURE:
<223> OTHER INFORMATION: Heavy chain variable region for DX-2504

<400> SEQUENCE: 9

Glu Val Gln Leu Leu Glu Ser Gly Gly Gly Leu Val Gln Pro Gly Gly

```
                1               5                   10                  15
            Ser Leu Arg Leu Ser Cys Ala Ala Ser Gly Phe Thr Phe Ser Glu Tyr
                        20                  25                  30

Ala Met Gly Trp Val Arg Gln Ala Pro Gly Lys Gly Leu Glu Trp Val
                        35                  40                  45

Ser Ser Ile Gly Ser Ser Gly Gly Gln Thr Lys Tyr Ala Asp Ser Val
                        50                  55                  60

Lys Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                            85                  90                  95

Ala Arg Leu Ala Ile Gly Asp Ser Tyr Trp Gly Gln Gly Thr Met Val
                            100                 105                 110

Thr Val Ser Ser
                    115

<210> SEQ ID NO 10
<211> LENGTH: 110
<212> TYPE: PRT
<213> ORGANISM: Artificial sequence
<220> FEATURE:
<223> OTHER INFORMATION: Light chain Variable region for 532A-X53-C02

<400> SEQUENCE: 10

Gln Ser Ala Leu Thr Gln Pro Ala Ser Val Ser Gly Ser Pro Gly Gln
            1               5                   10                  15

Ser Ile Thr Ile Ser Cys Thr Gly Thr Gly Ser Asp Val Gly Ser Tyr
                            20                  25                  30

Asn Leu Val Ser Trp Tyr Gln Gln His Pro Gly Lys Ala Pro Lys Leu
                            35                  40                  45

Met Ile Tyr Gly Asp Ser Gln Arg Pro Ser Gly Val Ser Asn Arg Phe
                        50                  55                  60

Ser Gly Ser Lys Ser Gly Asn Thr Ala Ser Leu Thr Ile Ser Gly Leu
            65                  70                  75                  80

Gln Ala Glu Asp Glu Ala Asp Tyr Tyr Cys Ser Ser Tyr Ala Gly Ser
                            85                  90                  95

Gly Ile Tyr Val Phe Gly Thr Gly Thr Lys Val Thr Val Leu
                            100                 105                 110

<210> SEQ ID NO 11
<211> LENGTH: 110
<212> TYPE: PRT
<213> ORGANISM: Artificial sequence
<220> FEATURE:
<223> OTHER INFORMATION: Light chain Variable region for 532A-X54-B03

<400> SEQUENCE: 11

Gln Ser Ala Leu Thr Gln Pro Ala Ser Val Ser Gly Ser Pro Gly Gln
            1               5                   10                  15

Ser Ile Thr Ile Ser Cys Thr Gly Thr Gly Ser Asp Val Gly Ser Tyr
                            20                  25                  30

Asn Leu Val Ser Trp Tyr Gln Gln His Pro Gly Lys Ala Pro Lys Leu
                            35                  40                  45

Met Ile Tyr Gly Asp Ser Gln Arg Pro Ser Gly Val Ser Asn Arg Phe
                        50                  55                  60

Ser Gly Ser Lys Ser Gly Asn Thr Ala Ser Leu Thr Ile Ser Gly Leu
            65                  70                  75                  80
```

Gln Ala Glu Asp Glu Ala Asp Tyr Tyr Cys Ala Ser Tyr Ala Gly Ser
                85                  90                  95

Gly Ile Tyr Val Phe Gly Thr Gly Thr Lys Val Thr Val Leu
            100                 105                 110

<210> SEQ ID NO 12
<211> LENGTH: 10
<212> TYPE: PRT
<213> ORGANISM: Artificial sequence
<220> FEATURE:
<223> OTHER INFORMATION: Light chain variable region CDR3 of
      532A-X53-C02

<400> SEQUENCE: 12

Ser Ser Tyr Ala Gly Ser Gly Ile Tyr Val
1               5                   10

<210> SEQ ID NO 13
<211> LENGTH: 10
<212> TYPE: PRT
<213> ORGANISM: Artificial sequence
<220> FEATURE:
<223> OTHER INFORMATION: Light chain variable region CDR3 of
      532A-X54-B03

<400> SEQUENCE: 13

Ala Ser Tyr Ala Gly Ser Gly Ile Tyr Val
1               5                   10

<210> SEQ ID NO 14
<211> LENGTH: 14
<212> TYPE: PRT
<213> ORGANISM: Artificial sequence
<220> FEATURE:
<223> OTHER INFORMATION: Light chain variable region CDR1

<400> SEQUENCE: 14

Thr Gly Thr Gly Ser Asp Val Gly Ser Tyr Asn Leu Val Ser
1               5                   10

<210> SEQ ID NO 15
<211> LENGTH: 7
<212> TYPE: PRT
<213> ORGANISM: Artificial sequence
<220> FEATURE:
<223> OTHER INFORMATION: Light chain variable region CDR2

<400> SEQUENCE: 15

Gly Asp Ser Gln Arg Pro Ser
1               5

<210> SEQ ID NO 16
<211> LENGTH: 216
<212> TYPE: PRT
<213> ORGANISM: Artificial sequence
<220> FEATURE:
<223> OTHER INFORMATION: Full length light chain for DX-2504

<400> SEQUENCE: 16

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Leu Val Ser Trp Tyr Gln Gln His Pro Gly Lys Ala Pro Lys Leu
        35                  40                  45

```
Met Ile Tyr Gly Asp Ser Gln Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Gly Ile Tyr Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 17
<211> LENGTH: 446
<212> TYPE: PRT
<213> ORGANISM: Artificial sequence
<220> FEATURE:
<223> OTHER INFORMATION: Full length heavy chain for DX-2504

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Ala Met Gly Trp Val Arg Gln Ala Pro Gly Lys Gly Leu Glu Trp Val
        35                  40                  45

Ser Ser Ile Gly Ser Ser Gly Gly Gln Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 18
<211> LENGTH: 216
<212> TYPE: PRT
<213> ORGANISM: Artificial sequence
<220> FEATURE:
<223> OTHER INFORMATION: Full length light chain for DX-2507

<400> SEQUENCE: 18

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Asp Ser Gln Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Ser
                85                  90                  95

Gly Ile Tyr Val Phe Gly Thr Gly Thr Lys Val Thr Val Leu Gly Gln
            100                 105                 110

```
Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 19
<211> LENGTH: 445
<212> TYPE: PRT
<213> ORGANISM: Artificial sequence
<220> FEATURE:
<223> OTHER INFORMATION: Full length heavy chain for DX-2507

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Ala Met Gly Trp Val Arg Gln Ala Pro Gly Lys Gly Leu Glu Trp Val
        35                  40                  45

Ser Ser Ile Gly Ser Ser Gly Gly Gln Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255
```

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
                435                 440                 445

<210> SEQ ID NO 20
<211> LENGTH: 48
<212> TYPE: PRT
<213> ORGANISM: Artificial sequence
<220> FEATURE:
<223> OTHER INFORMATION: C-terminal fragment of DX-2504 heavy chain

<400> SEQUENCE: 20

Ser Asp Gly Ser Phe Phe Leu Tyr Ser Lys Leu Thr Val Asp Lys Ser
1               5                   10                  15

Arg Trp Gln Gln Gly Asn Val Phe Ser Cys Ser Val Met His Glu Ala
            20                  25                  30

Leu His Asn His Tyr Thr Gln Lys Ser Leu Ser Leu Ser Pro Gly Lys
        35                  40                  45

<210> SEQ ID NO 21
<211> LENGTH: 47
<212> TYPE: PRT
<213> ORGANISM: Artificial sequence
<220> FEATURE:
<223> OTHER INFORMATION: the C-terminal fragment of DX-2507 heavy chain

<400> SEQUENCE: 21

Ser Asp Gly Ser Phe Phe Leu Tyr Ser Lys Leu Thr Val Asp Lys Ser
1               5                   10                  15

Arg Trp Gln Gln Gly Asn Val Phe Ser Cys Ser Val Met His Glu Ala
            20                  25                  30

Leu His Asn His Tyr Thr Gln Lys Ser Leu Ser Leu Ser Pro Gly
        35                  40                  45

<210> SEQ ID NO 22
<211> LENGTH: 5
<212> TYPE: PRT
<213> ORGANISM: Artificial sequence

```
<220> FEATURE:
<223> OTHER INFORMATION: Heavy chain variable region CDR1

<400> SEQUENCE: 22

Glu Tyr Ala Met Gly
1               5

<210> SEQ ID NO 23
<211> LENGTH: 17
<212> TYPE: PRT
<213> ORGANISM: Artificial sequence
<220> FEATURE:
<223> OTHER INFORMATION: Heavy chain variable region CDR2

<400> SEQUENCE: 23

Ser Ile Gly Ser Ser Gly Gly Gln Thr Lys Tyr Ala Asp Ser Val Lys
1               5                   10                  15

Gly

<210> SEQ ID NO 24
<211> LENGTH: 7
<212> TYPE: PRT
<213> ORGANISM: Artificial sequence
<220> FEATURE:
<223> OTHER INFORMATION: Heavy chain variable region CDR3

<400> SEQUENCE: 24

Leu Ala Ile Gly Asp Ser Tyr
1               5

<210> SEQ ID NO 25
<211> LENGTH: 10
<212> TYPE: PRT
<213> ORGANISM: Artificial sequence
<220> FEATURE:
<223> OTHER INFORMATION: Light chain variable region CDR3 of DX-2504

<400> SEQUENCE: 25

Cys Ser Tyr Ala Gly Ser Gly Ile Tyr Val
1               5                   10

<210> SEQ ID NO 26
<211> LENGTH: 329
<212> TYPE: PRT
<213> ORGANISM: Artificial sequence
<220> FEATURE:
<223> OTHER INFORMATION: Heavy chain constant region of DX-2507

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325
```

ANTIBODIES WHICH BIND FC RECEPTORS (FCRN)

RELATED APPLICATIONS

This application is a continuation of U.S. patent application Ser. No. 16/594,218, tiled Oct. 7, 2019, now U.S. Pat. No. 11,014,988, which is a divisional of U.S. patent application Ser. No. 15/830,998, filed Dec. 4, 2017, now U.S. Pat. No. 10,479,834, which is a continuation of U.S. patent application Ser. No. 15/139,784, filed on Apr. 27, 2016, now U.S. Pat. No. 9,862,768, which is a continuation of U.S. patent application Ser. No. 14/122,880, filed on Jul. 2, 2014, now U.S. Pat. No. 9,359,438, which is a national stage filing under 35 U.S.C. § 371 of international application number PCT/US2012/040409, filed Jun. 1, 2012, which claims priority under 35 U.S.C. § 119 to U.S. Provisional Application No. 61/492,617, filed Jun. 2, 2011, and U.S. Provisional Application No. 61/498,266, filed Jun. 17, 2011, the entire-contents of each of which are herein incorporated by reference in their entirety.

FIELD OF THE INVENTION

The field of invention relates to proteins that bind the Fc receptor.

BACKGROUND OF THE INVENTION

The most abundant antibody isotype in the serum is IgG and it has a critical role in mediating protection against pathogens as well as in mediating allergic and inflammatory responses that hasten recruitment of immune system components to the tissues, mucosae, and dermal surfaces (Junghans, Immunologic Research 16(1):29 (1997)). Moreover, it is also a key component of a variety of autoimmune diseases. Under normal conditions, the halflife of IgG in the serum is in the range of 5-7 days in mice and 22-23 days in humans, which is a prolonged period, relative to the serum half life of other plasma proteins. In part, this occurs because the neonatal FcRn receptor (FcRn) rescues pinocytosed IgG from degradative lysosomes and recycles it back to the extracellular compartment (Junghans and Anderson, Proc. Natl. Acad. Sci. USA 93:5512 (1996), Roopenian et al. J. Immunology 170:3528 (2003)).

FcRn binds to the Fc portion of IgG. The interaction between the IgG Fc region and FcRn is pH-dependent. Upon entry into cells by fluid phase endocytosis, IgG is sequestered into endosomes and binds to FcRn with high affinity at acidic pH (6~6.5); when the IgG-FcRn complex cycles to the plasma membrane, IgG dissociates rapidly from FcRn in the bloodstream at slightly basic pH (~7.4). By this receptor-mediated recycling mechanism, FcRn effectively rescues the IgG from degradation in lysosomes, thereby prolonging the half-life of circulating IgG.

FcRn is a non-covalent heterodimer that typically resides in the endosomes of endothelial and epithelial cells. It is a membrane bound receptor with a single-pass transmembrane having three heavy chain alpha domains ($\alpha$1, $\alpha$2, and $\alpha$3) and a single soluble light chain $\beta$2-microglobulin ($\beta$2M) domain. Structurally, it belongs to a family of major histocompatibility complex class 1 molecules that have $\beta$2M as a common light chain. The FcRn $\alpha$ chain is a 46 kD protein composed of an extracellular domain containing the $\alpha$1, $\alpha$2, and $\alpha$3 heavy chain domains, a transmembrane region, and a relatively short cytoplasmic tail (Burmeister et al. Nature 372:366 (1994)).

FcRn was first identified in the neonatal rat gut, where it functions to mediate the absorption of IgG antibody from the mother's milk and facilitates its transport to the circulatory system (Leach et al. J Immunol 157:3317 (1996)). FcRn has also been isolated from human placenta, where it also mediates absorption and transport of maternal IgG to the fetal circulation. In adults, FcRn is expressed in a number of tissues, including epithelial tissues of the lung, intestine, kidney, as well as nasal, vaginal, and biliary tress surfaces (U.S. Pat. Nos. 6,030,613 and 6,086,875; Israel et al. Immunology 92:69 (1997); Kobayashi et al. Am J Physiol (2002); Renal Physiol 282:F358 (2002)).

In order to study the contributions of FcRn to IgG homeostasis, mice have been engineered so that at least part of the genes encoding $\beta$2M and FcRn heavy chains have been "knocked out" so that these proteins are not expressed (WO 02/43658; Junghans and Anderson, Proc Natl Acad Sci US 93:5512 (1996)). In these mice, the serum half-life and concentrations of IgG were dramatically reduced, suggesting a FcRn dependent mechanism for IgG homeostasis.

It has also been suggested that anti-human FcRn antibodies may be generated in these FcRn knockout mice and that these antibodies may prevent the binding of IgG to FcRn. However, such antibodies have not been generated or tested (WO 02/43658).

The inhibition of IgG binding to FcRn negatively alters IgG serum half-life by preventing IgG recycling. This principle has been shown to be therapeutically effective in a mouse model of autoimmune cutaneous bullous diseases (Li et al. J Clin Invest 115:3440-3450 (2005)). Accordingly, agents that block or antagonize the binding of IgG to FcRn may be used in a method to treat or prevent autoimmune and inflammatory diseases or disorders characterized by the presence of inappropriately regulated IgG antibodies. An antagonistic anti-rat FcRn monoclonal antibody (mAb)1G3 successfully prevented Experimental Autoimmune Myasthenia Gravis (EAMG) in a rat passive model at a dose of 30 mg/kg; that is about 100 fold lower than the intravenous IgG (IVIG) used in treatment of MG, SLE, and ITP. Further, FcRn-deficient mice genetically predisposed to develop autoimmune disorder such as lupus or arthritis have significant reduction in severity of the disease.

SUMMARY OF THE INVENTION

The present disclosure provides isolated antibodies that bind the human Fc receptor, nucleic acids encoding such antibodies, and methods of using these antibodies to detect presence of FcRn, modulate Fc receptor activity, and treat autoimmune disorders.

Accordingly, one aspect of the present disclosure features an isolated antibody that binds to human FcRn. This anti-FcRn antibody comprises a light chain variable region ($V_L$) that comprises a $V_L$ CDR1, a $V_L$ CDR2 and a $V_L$ CDR3 region, wherein the $V_L$ CDR3 region has at least 85% (e.g., 90% or 95%) homology with the $V_L$ CDR3 region of SSYAGSGIYV (SEQ ID NO:12) or ASYAGSGIYV (SEQ ID NO:13). Optionally, the $V_L$ CDR1 and $V_L$ CDR2 of the anti-FcRn antibody have at least 85% (e.g., at least 90% or 95%) homology with the $V_L$ CDR1 region TGTGSDVGSYNLVS (SEQ ID NO:14) and $V_L$ CDR2 region GDSQRPS (SEQ ID NO:15), respectively. The anti-FcRn antibody does not have a cysteine at the first position of at least one CDR3 region, e.g., at least one of the $V_L$ CDR3 regions.

In some embodiments, the above-described anti-FcRn antibody comprises a $V_L$ CDR1 having at least 90% homology with TGTGSDVGSYNLVS (SEQ ID NO:14), a $V_L$ CDR2 having at least 90% homology with GDSQRPS (SEQ ID NO:15), and/or a $V_L$ CDR3 having at least 90% homology with SSYAGSGIYV (SEQ ID NO:12) or ASYAGSGIYV (SEQ ID NO:13). In one example, the anti-FcRn antibody comprises the $V_L$ CDR1 region TGTGSDVGSYNLVS (SEQ ID NO:14), the $V_L$ CDR2 region GDSQRPS (SEQ ID NO:15), and/or the $V_L$ CDR3 region SSYAGSGIYV (SEQ ID NO:12) or ASYAGSGIYV (SEQ ID NO:13).

In other embodiments, the isolated anti-FcRn antibody disclosed herein comprises a $V_L$ that comprises an amino acid sequence having at least 85% (e.g., at least 90%, 95% or 98%) homology with SEQ ID NO:10 or SEQ ID NO:11. In one example, the $V_L$ of the isolated antibody comprises the amino acid sequence of SEQ ID NO: 10 or SEQ ID NO: 11.

Another aspect of the present disclosure features an isolated anti-FcRn antibody comprising a light chain variable region ($V_L$) that comprises a $V_L$ CDR1, a $V_L$ CDR2 and a $V_L$ CDR3 region, wherein the $V_L$ CDR3 region has up to 3 amino acid substitutions as compared to the following sequence: SSYAGSGIYV (SEQ ID NO: 12) or ASYAGSGIYV (SEQ ID NO:13), and wherein the isolated antibody does not have a cysteine at the first position of at least one CDR3 region e.g., at least one of the $V_L$ CDR3 regions. Optionally, the $V_L$ CDR1, $V_L$ CDR2 and $V_L$ CDR3 of the anti-FcRn antibody, collectively, contain up to 10 amino acid substitutions as compared to the following sequences (a) CDR1:
TGTGSDVGSYNLVS (SEQ ID NO: 14)

(b) CDR2:
GDSQRPS (SEQ ID NO: 15)

(c) CDR3:
SSYAGSGIYV, (SEQ ID NO: 12)
or
ASYAGSGIYV (SEQ ID NO: 13)

Any of the anti-FcRn antibodies described above can further comprise a heavy chain variable region ($V_H$) that comprises a $V_H$ CDR1, a $V_H$ CDR2, and a $V_H$ CDR3, wherein the $V_H$ CDR3 has at least 85% (e.g., at least 90% or 95%) homology with LAIGDSY (SEQ ID NO:24). Optionally, the $V_H$ CDR1 and $V_H$ CDR2 of the anti-FcRn antibody have at least 85% (e.g., at least 90% or 95%) homology with EYAMG (SEQ ID NO:22) and SIGSSGGQTKYADSVKG (SEQ ID NO:23), respectively.

In some embodiments, the anti-FcRn antibody comprises a $V_H$ CDR1 having at least 90% homology with EYAMG (SEQ ID NO:22), a $V_H$ CDR2 has at least 90% homology with SIGSSGGQTKYADSVKG (SEQ ID NO:23), and/or a $V_H$ CDR3 has at least 90% homology with LAIGDSY (SEQ ID NO:24). In one example, the anti-FcRn antibody comprises the $V_H$ CDR1 region EYAMG (SEQ ID NO:22), the $V_H$ CDR2 region SIGSSGGQTKYADSVKG (SEQ ID NO:23), and/or the $V_H$ CDR3 region LAIGDSY (SEQ ID NO:24).

In other embodiments, the anti-FcRn antibody disclosed herein comprises a $V_H$ that share at least 85% (e.g., at least 90%, 95%, or 98%) sequence identity to SEQ ID NO:9. In one example, the $V_H$ of the isolated antibody comprises the amino acid sequence of SEQ ID NO:9.

In another aspect, the present disclosure provides an isolated anti-FcRn antibody comprising a heavy chain that comprises a heavy chain variable region ($V_H$) and a heavy chain constant region, wherein the $V_H$ comprises a CDR3 region having at least 85% (e.g., at least 90% or 95%) homology with LAIGDSY (SEQ ID NO:24) and the constant region has a deletion at the position corresponding to the C-terminal lysine residue of SEQ ID NO: 17. In some examples, the heavy chain variable of this anti-FcRn antibody further comprises a $V_H$ CDR1 and a $V_H$ CDR2, which have at least 85% (e.g., at least 90% or 95%) homology with EYAMG (SEQ ID NO:22), and SIGSSGGQTKYADSVKG (SEQ ID NO:23), respectively. In other examples, the heavy chain constant region of the anti-FcRn antibody comprises the amino acid sequence of SEQ ID NO:26.

The above-described anti-FcRn antibody can further comprise a light chain variable region ($V_L$) that comprises a $V_L$ CDR3 at least 85% (e.g., at least 90% or 95%) identical to that of DX-2504 (CSYAGSGIYV; SEQ ID NO:25) and, optionally, a $V_L$ CDR1 at least 85% (e.g., at least 90% or 95%) identical TGTGSDVGSYNLVS (SEQ ID NO:14) and a $V_L$ CDR2 at least 85% (e.g., at least 90% or 95%) identical to GDSQRPS (SEQ ID NO: 15). In one example, the anti-FcRn antibody comprises the $V_L$ CDR1 region TGTGSDVGSYNLVS (SEQ ID NO:14), the $V_L$ CDR2 region GDSQRPS (SEQ ID NO:15), and/or the $V_L$ CDR3 region CSYAGSGIYV (SEQ ID NO:25), SSYAGSGIYV (SEQ ID NO:12), or ASYAGSGIYV (SEQ ID NO: 13). In another example, the $V_L$ of the anti-FcRn antibody comprises the amino acid sequence of SEQ ID NO:8, SEQ ID NO:10, or SEQ ID NO:11.

Any of the anti-FcRn antibodies described above can bind human FcRn with a dissociation constant ($K_D$) of less than 10 nM. The anti-FcRn antibodies provided in the present disclosure can be human or humanized antibodies, or non-immunogenic in a human. For example, they can comprise a human antibody framework region. Alternatively, the anti-FcRn antibodies can be murine antibodies. In other examples, they can be chimeric antibodies.

In some embodiments, the anti-FcRn antibodies provided herein are full-length antibodies (comprising a Fc domain). Alternatively, they can be antigen-binding fragments such as Fab, F(ab)'2, Fv, or ScFv. When desired, the anti-FcRn antibodies are monoclonal antibodies.

Also disclosed herein are (i) a pharmaceutical composition comprising any of the antibodies described herein and a pharmaceutically acceptable carrier, (ii) an isolated nucleic acid comprising a sequence that encodes any of the antibodies provided herein, (iii) a vector comprising any of the nucleic acids comprising a sequence that encodes any of the antibodies provided herein, and (iv) a host cell comprising the vector comprising any of the nucleic acids comprising a sequence that encodes any of the antibodies provided herein.

Any of the anti-FcRn antibodies described herein can be used to detect the presence of an FcRn or modulate the activity of an FcRn, either in vivo or in vitro.

In one aspect, provide herein is a method of detecting an FcRn in a sample, the method comprising: contacting the sample with any of the antibodies provided herein, and detecting an interaction between the antibody and the FcRn if present.

In another aspect the present disclosure provides a method of detecting an FcRn in a subject, the method comprising: administering to the subject any of the antibodies provided herein, which can be conjugated with a detectable molecule such as an imaging label (fluorescent or radioactive), and detecting an interaction between the antibody and the FcRn if present.

In yet another aspect, the present disclosure provides a method of modulating an FcRn activity, the method comprising: contacting an FcRn with any of the antibodies provided herein thereby modulating the activity of the FcRn.

In one aspect the invention provides a method of treating an autoimmune disorder or modulating the half life/levels of circulating IgG in a subject, the method comprising: administering to the subject any of the antibodies provided herein in an amount effective to treat the autoimmune disorder or to modulate the half life/levels of circulating IgG in the subject.

Also within the scope of the present disclosure are (a) pharmaceutical compositions for use in modulating the activity of an FcRn, modulating the half life/levels of circulating IgG, and/or treating an autoimmune disorder in a subject in need thereof, wherein the pharmaceutical compositions each comprise one of more of the anti-FcRn antibodies described herein and a pharmaceutically acceptable carrier, (b) the use of any of the anti-FcRn antibodies described herein for any of the just-noted purposes, and (c) the use of any of the anti-FcRn antibodies for the manufacture of a medicament for modulating the activity of FcRn, modulating the half life/levels of circulating IgG, and/or treating an autoimmune disorder in a subject (e.g., a human patient).

These and other aspects and embodiments of the invention are described in greater detail below.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

FIG. 9 shows the sequences of DX2504 (SEQ ID NO:8), 532A-X53-C02 (SEQ ID NO:10), and 532A-X54-B03 (SEQ ID NO:11).

FIG. 10 shows the anti-hFcRn H-CDR3 vs. Fab-310 length distributions.

DETAILED DESCRIPTION OF THE INVENTION

Figure 1:
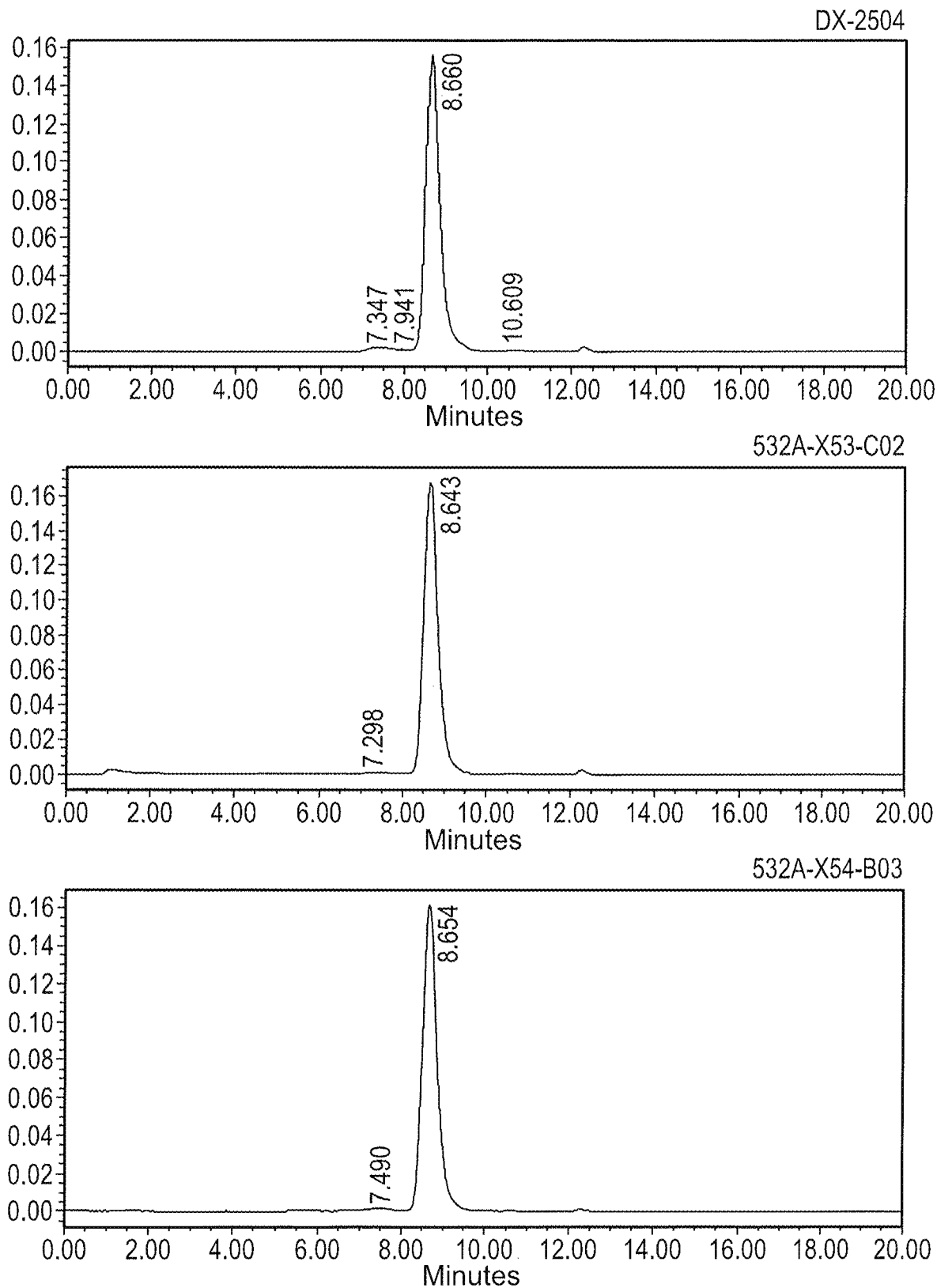
FIG. 1 shows a Size Exclusion Chromatography (SEC) analysis of DX-2504, 532A-X53-C02 and 532A-X54-B03.

Disclosed herein are isolated antibodies capable of binding to human FcRn and uses thereof in detecting presence of FcRn, modulating FcRn activity, regulating the half-life/level of circulating IgGs, and/or treating disorders associated with IgG abnormality, such as autoimmune disorders (e.g., multiple sclerosis, rheumatoid arthritis, lupus, immune thrombocytopenia, ankylosing spondylitis, and pemphigus), and inflammatory disorders such as inflammatory bowel disease. Preferably, such anti-FcRn antibodies can (a) block the binding of non-specific human IgG/Fc portion to the FcRn-Fc interacting site; (b) bind to both human and rat FcRn (soluble and cells); (c) bind to FcRn at pH 6; and/or (d) not exclusively bind to β2M.

In normal circumstances, FcRn can extend the half-life of circulating IgG. Antibodies that bind to FcRn can be used to modulate FcRn function, for example, by preventing its interaction with IgG. In particular, antibodies that block FcRn interaction with IgG can be used to reduce the half-life of IgG molecules.

In one aspect, the disclosure provides, inter alia, human antagonistic anti-human FcRn antibodies that are available for the treatment of autoimmune disorders and reduction of circulating levels of IgGs. Also disclosed are high affinity soluble Fabs (sFab) with the ability to bind through the antigen binding domain and block the interaction between IgG-Fc and human FcRn or rat FcRn.

Definitions

The term "binding protein" refers to a protein that can interact with a target molecule. This term is used interchangeably with "ligand." An "FcRn-binding protein" or "FcRn-binding ligand" refers to a protein that can interact with an FcRn, and includes, in particular, proteins that preferentially interact with an FcRn, e.g., IgG.

As used herein, the term "antibody" refers to a protein that includes at least one immunoglobulin variable domain or immunoglobulin variable domain sequence. For example, an antibody can include a heavy (H) chain variable region (abbreviated herein as $V_H$), and a light (L) chain variable region (abbreviated herein as $V_L$). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and dAb fragments) as well as complete antibodies (full-length antibodies).

The $V_H$ and $V_L$ regions can be further subdivided into regions of hypervariability, termed "complementarity determining regions" ("CDR"), interspersed with regions that are more conserved, termed "framework regions" ("FR"). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, see also http://www.hgmp.mrc.ac.uk). Kabat definitions are used herein. Each VH and VL is typically composed of three CDR's and four FR's, arranged from amino-terminus to carboxy-terminus in the following order: FR1, CDR1, FR2, CDR2, FR3, CDR3, FR4.

The term "antigen-binding fragment" of a full length antibody (or simply "antibody portion," or "fragment"), as used herein, refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the $V_L$, $V_H$, $C_L$ and $C_H1$ domains; (ii) a F(ab')$_2$ fragment, a bivalent fragment including two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) that retains functionality. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition. As used herein, "isotype" refers to the antibody class (e.g., IgM or IgG1) that is encoded by heavy chain constant region genes.

As used herein, "binding affinity" refers to the apparent association constant or $K_a$. The $K_a$ is the reciprocal of the dissociation constant ($K_d$). A binding protein may, for example, have a binding affinity of at least $10^{-5}$, $10^{-6}$, $10^{-7}$, $10^{-8}$, $10^{-9}$, $10^{-10}$ and $10^{-11}$ M for a particular target molecule. Higher affinity binding of a binding ligand to a first target relative to a second target can be indicated by a higher $K_a$ (or a smaller numerical value $K_d$) for binding the first target than the $K_a$ (or numerical value $K_d$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 50, 70, 80, 100, 500, 1000, or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in PBS (phosphate buffered saline) at pH 7.2 at 30° C. These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[\text{Bound}] = N \cdot [\text{Free}]/((1/K_a) + [\text{Free}]).$$

It is not always necessary to make an exact determination of $K_a$, though, since sometimes it is sufficient to obtain a quantitative measurement of affinity, e.g., determined using a method such as ELISA or FACS analysis, is proportional to $K_a$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term "cognate ligand" refers to a naturally occurring ligand of an FcRn, including naturally occurring variants thereof (e.g., splice variants, naturally occurring mutants, and isoforms).

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). It is possible for many framework and CDR amino acid residues to include one or more conservative substitutions.

Consensus sequences for biopolymers can include positions which can be varied among various amino acids. For example, the symbol "X" in such a context generally refers to any amino acid (e.g., any of the twenty natural amino acids or any of the nineteen non-cysteine amino acids). Other allowed amino acids can also be indicated for example, using parentheses and slashes. For example, "(A/W/F/N/Q)" means that alanine, tryptophan, phenylalanine, asparagine, and glutamine are allowed at that particular position.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blosum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In one embodiment, the length of a reference sequence aligned for comparison purposes is at least 30%, at least 40%, at least 50%, at least 60%, at least 70%, 80%, 90%, 92%, 95%, 97%, 98%, or 100% of the length of the reference sequence. For example, the reference sequence may be the length of the immunoglobulin variable domain sequence.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and non-aqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The disclosure includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence.

An FcRn binding protein may have mutations (e.g., at least one, two, or four, and/or less than 15, 10, 5, or 3) relative to a binding protein described herein (e.g., a conservative or non-essential amino acid substitutions), which do not have a substantial effect on the protein functions. Whether or not a particular substitution will be tolerated, i.e., will not adversely affect biological properties, such as binding activity can be predicted, e.g., using the method of Bowie, et al. (1990) *Science* 247:1306-1310.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 *Ann. Rev Immunol.* 6:381-405).

As used herein, an "immunoglobulin variable domain sequence" refers to an amino acid sequence which can form the structure of an immunoglobulin variable domain such that one or more CDR regions are positioned in a conformation suitable for an antigen binding site. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form a target binding structure (or "antigen binding site"), e.g., a structure that preferentially interacts with an FcRn structure.

The $V_H$ or $V_L$ chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, $C_H1$, $C_H2$ and $C_H3$. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The term "antibody" includes intact immunoglobulins of types IgA, IgG, IgE, IgD, IgM (as well as subtypes thereof). The light chains of the immunoglobulin may be of types: kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human or effectively human. In one embodiment, at least 70, 75, 80, 85, 90, 92, 95, or 98% of, or the entire of, the antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

The term "mimic," in the context of a mimic of a conformation of an FcRn or portion thereof, refers to a modified FcRn which has a bias for at least one particular conformation relative to a naturally occurring FcRn, or portion thereof.

A "non-essential" amino acid residue is a residue that can be altered from the wild-type sequence of the binding agent, e.g., the antibody, without abolishing or without substantially altering a biological activity, whereas an "essential" amino acid residue results in such a change.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The terms "polypeptide" or "peptide" (which may be used interchangeably) refer to a polymer of three or more amino acids linked by a peptide bond, e.g., between 3 and 30, 12 and 60, or 30 and 300, or over 300 amino acids in length. The polypeptide may include one or more unnatural amino acids. Typically, the polypeptide includes only natural amino acids. A "protein" can include one or more polypeptide chains. Accordingly, the term "protein" encompasses polypeptides. A protein or polypeptide can also include one or more modifications, e.g., a glycosylation, amidation, phosphorylation, nitrosylation, and so forth. The term "small peptide" can be used to describe a polypeptide that is between 3 and 30 amino acids in length, e.g., between 8 and 24 amino acids in length.

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher. In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding, that are statistically significant (e.g., P value<0.05 or 0.02). The terms "induce", "inhibit", "potentiate", "elevate", "increase", "decrease" or the like, e.g., which denote distinguishable qualitative or quantitative differences between two states, and may refer to a difference, e.g., a statistically significant difference, between the two states.

A "therapeutically effective dosage" modulates a measurable parameter, e.g., levels of circulating IgG antibodies by a statistically significant degree or at least about 20%, by at least about 40%, by at least about 60%, or by at least about 80% relative to untreated subjects. The ability of a compound to modulate a measurable parameter, e.g., autoimmunity, can be evaluated in an animal model system predictive of efficacy in human autoimmune disorders. Alternatively, this property of a composition can be evaluated by examining the ability of the compound to modulate a parameter in vitro, e.g., by assays known to the skilled practitioner.

Other features and advantages of the instant invention will become more apparent from the following detailed description and claims. Embodiments of the invention can include any combination of features described herein. In no case does the term "embodiment" exclude one or more other features disclosed herein.

FcRn Sequences

The following sequence alignment is of a human FcRn alpha chain amino acid sequence with a rat FcRn alpha chain amino acid sequence An exemplary FcRn protein can include one of these two sequences, or a fragment thereof, e.g., a fragment without the signal sequence:

```
             Signal Sequence                            α₁ domain
α_HUMAN:     MGVPRPQPWALGLLLFLLPGSLG AESHLSLLYHLTAVSSPAPGTPAFWVSGWLGPQQYLS
α_RAT:       MGMSQPGV-LLSLLLVLLPQTWG AEPRLPLMYHLAAVSDLSTGLPSFWATGWLGAQQYLT α₁ domain                               α₂ domain
α_HUMAN:     YNSLRGEAEPCGAWVWENQVSWYWEKETTDLRIKEKLFLEAFKALGGK--GP YTLQGLLG
α_RAT:       YNNLRQEADPCGAWIWENQVSWYWEKETTDLKSKEQLFLEAIRTLENQINGT FTLQGLLG α₂ domain
α_HUMAN:     CELGPDNTSVPTAKFALNGEEFMNFDLKQGTWGGDWPEALAISQRWQQQDKAANKELTFL
α_RAT:       CELAPDNSSLPTAVFALNGEEFMRFNPRTGNWSGEWPETDIVGNLWMKQPEAARKESEFL α₂ domain                          α₃ domain
α_HUMAN:     LFSCPHRLREHLERGRGNLEWK EPPSMRLKARPSSPGFSVLTCSAFSFYPPELQLRFLRN
α_RAT:       LTSCPERLLGHLERGRQNLEWK EPPSMRLKARPGNSGSSVLTCAAFSFYPPELKFRFLRN α₃ domain
α_HUMAN:     GLAAGTGQGDFGPNSDGSFHASSSLTVKSGDEHHYCCIVQHAGLAQPLRVELE
α_RAT:       GLASGSGNCSTGPNGDGSFHAWSLLEVKRGDEHHYQCQVEHEGLAQPLTVDLD Transmembrane                 Cytoplasmic domain
α_HUMAN:     SPAKSSVLVVGIVIGVLLLTAAAVGGALLW RRMRSGLPAPWISLRGDDTGVLLPTPGEAQ
α_RAT:       SPARSSVPVVGIILGLLLVVVAIAGGVLLW NRMRSGLPAPWLSLSGDDSGDLLPGGNLPP α_HUMAN:     DADLKDVNVIPATA (SEQ ID NO: 1)
α_RAT:       EAEPOGVNAFPATS (SEQ ID NO: 2)
```

The following sequence alignment is of a human β2 microglobulin amino acid sequence with a rat β2 microglobulin amino acid sequence. An exemplary FcRn protein can include one of these two sequences, or a fragment thereof, e.g., a fragment without the signal sequence:

```
             Signal Sequence              β2 microglobulin
β2m_human:   MSRSVALAVLALLSLSGLEA IQRTPKIQVYSRHPAENGKSNFLNCYVSGFHPSDIEVDLL
β2m_rat:     MARSVTVIFLVLVSLAVVLA IQKTPQIQVYSRHPPENGKPNFLNCYVSQFHPPQIEIELL β2 microglobulin
β2m_human:   KNGERIEKVEHSDLSFSKDWSFYLLYYTEFTPTEKDEYACRVNHVTLSQPKIVKWDRDM (SEQ ID NO: 3)
β2m_rat:     KNGKKIPNIEMSDLSFSKDWSFYILAHTEFTPTETDVYACRVKHVTLKEPKTVTWDRDM (SEQ ID NO: 4)
```

An exemplary nucleic acid sequence encoding an FcRn protein alpha chain can include the following sequences:

```
FcRn alpha nucleotide sequence (Homo sapiens):
                                                (SEQ ID NO: 5)
GTTCTTCAGGTACGAGGAGGGCATTGTTGTCAGTCTGGACCGAGCCCGCAGAGCCCCTCCTCGGCGTCCT

GGTCCCGGCCGTGCCCGCGGTGTCCCGGGAGGAAGGGGCGGGCCGGGGGTCGGGAGGAGTCACGTGCCCC

CTCCCGCCCCAGGTCGTCCTCTCAGCATGGGGGTCCCGCGGCCTCAGCCCTGGGCGCTGGGGCTCCTGCT

CTTTCTCCTTCCTGGGAGCCTGGGCGCAGAAAGCCACCTCTCCCTCCTGTACCACCTTACCGCGGTGTCC

TCGCCTGCCCCGGGGACTCCTGCCTTCTGGGTGTCCGGCTGGCTGGGCCCGCAGCAGTACCTGAGCTACA

ATAGCCTGCGGGGCGAGGCGGAGCCCTGTGGAGCTTGGGTCTGGGAAAACCAGGTGTCCTGGTATTGGGA

GAAAGAGACCACAGATCTGAGGATCAAGGAGAAGCTCTTTCTGGAAGCTTTCAAAGCTTTGGGGGGAAAA

GGTCCCTACACTCTGCAGGGCCTGCTGGGCTGTGAACTGGGCCCTGACAACACCTCGGTGCCCACCGCCA

AGTTCGCCCTGAACGGCGAGGAGTTCATGAATTTCGACCTCAAGCAGGGCACCTGGGGTGGGGACTGGCC

CGAGGCCCTGGCTATCAGTCAGCGGTGGCAGCAGCAGGACAAGGCGGCCAACAAGGAGCTCACCTTCCTG

CTATTCTCCTGCCCGCACCGCCTGCGGGAGCACCTGGAGAGGGGCCGCGGAAACCTGGAGTGGAAGGAGC

CCCCCTCCATGCGCCTGAAGGCCCGACCCAGCAGCCCTGGCTTTTCCGTGCTTACCTGCAGCGCCTTCTC

CTTCTACCCTCCGGAGCTGCAACTTCGGTTCCTGCGGAATGGGCTGGCCGCTGGCACCGGCCAGGGTGAC

TTCGGCCCCAACAGTGACGGATCCTTCCACGCCTCGTCGTCACTAACAGTCAAAAGTGGCGATGAGCACC

ACTACTGCTGCATTGTGCAGCACGCGGGGCTGGCGCAGCCCCTCAGGGTGGAGCTGGAATCTCCAGCCAA
```

```
GTCCTCCGTGCTCGTGGTGGGAATCGTCATCGGTGTCTTGCTACTCACGGCAGCGGCTGTAGGAGGAGCT

CTGTTGTGGAGAAGGATGAGGAGTGGGCTGCCAGCCCCTTGGATCTCCCTTCGTGGAGACGACACCGGGG

TCCTCCTGCCCACCCCAGGGGAGGCCCAGGATGCTGATTTGAAGGATGTAAATGTGATTCCAGCCACCGC

CTGACCATCCGCCATTCCGACTGCTAAAAGCGAATGTAGTCAGGCCCCTTTCATGCTGTGAGACCTCCTG

GAACACTGGCATCTCTGAGCCTCCAGAAGGGGTTCTGGGCCTAGTTGTCCTCCCTCTGGAGCCCCGTCCT

GTGGTCTGCCTCAGTTTCCCCTCCTAATACATATGGCTGTTTTCCACCTCGATAATATAACACGAGTTTG

GGCCCGAAAAAAAAAAAAAAAAAAAAAAAAAAAAAAAAAA
```

The nucleic acid sequence of an exemplary human FcRn 15 (extra-cellular domain) plus GPI DNA sequences (lowercase bold) is set forth below.

(SEQ ID NO: 6)
```
ATGGGGGTCCCGCGGCCTCAGCCCTGGGCGCTGGGGCTCCTGCTCTTTCTCCTTCCTGGGAGCCTGGGCG

CAGAAAGCCACCTCTCCCTCCTGTACCACCTTACCGCGGTGTCCTCGCCTGCCCCGGGGACTCCTGCCTT

CTGGGTGTCCGGCTGGCTGGGCCCGCAGCAGTACCTGAGCTACAATAGCCTGCGGGGCGAGGCGGAGCCC

TGTGGAGCTTGGGTCTGGGAAAACCAGGTGTCCTGGTATTGGGAGAAAGAGACCACAGATCTGAGGATCAA

GGAGAAGCTCTTTCTGGAAGCTTTCAAAGCTTTGGGGGGAAAAGGTCCCTACACTCTGCAGGGCCTGCTGG

GCTGTGAACTGGGCCCTGACAACACCTCGGTGCCCACCGCCAAGTTCGCCCTGAACGGCGAGGAGTTCATG

AATTTCGACCTCAAGCAGGGCACCTGGGGTGGGGACTGGCCCGAGGCCCTGGCTATCAGTCAGCGGTGGCA

GCAGCAGGACAAGGCGGCCAACAAGGAGCTCACCTTCCTGCTATTCTCCTGCCCGCACCGCCTGCGGGAGC

ACCTGGAGAGGGCCGCGGAAACCTGGAGTGGAAGGAGCCCCCCTCCATGCGCCTGAAGGCCCGACCCAGC

AGCCCTGGCTTTTCCGTGCTTACCTGCAGCGCCTTCTCCTTCTACCCTCCGGAGCTGCAACTTCGGTTCCT

GCGGAATGGGCTGGCCGCTGGCACCGGCCAGGGTGACTTCGGCCCCAACAGTGACGGATCCTTCCACGCCT

CGTCGTCACTAACAGTCAAAAGTGGCGATGAGCACCACTACTGCTGCATTGTGCAGCACGCGGGGCTGGCG

CAGCCCCTCAGGGTGGAGCTGGAATCTCCAGCCAAGTCCTCCcggccgctcgacgggctacgagcatcagt aacactactaggcgcaggcctactactatcactactaccagcactactacgatttgggccataa
```

An exemplary nucleic acid sequence encoding a Beta-2-microglobulin (β2M) can include the following sequences:

Beta-2-microglobulin (B2M) nucleotide (Homo sapiens):
(SEQ ID NO: 7)
```
AATATAAGTGGAGGCGTCGCGCTGGCGGGCATTCCTGAAGCTGACAGCATTCGGGCCGAGATGTCTCGCT

CCGTGGCCTTAGCTGTGCTCGCGCTACTCTCTCTTTCTGGCCTGGAGGCTATCCAGCGTACTCCAAAGAT

TCAGGTTTACTCACGTCATCCAGCAGAGAATGGAAAGTCAAATTTCCTGAATTGCTATGTGTCTGGGTTT

CATCCATCCGACATTGAAGTTGACTTACTGAAGAATGGAGAGAGAATTGAAAAAGTGGAGCATTCAGACT

TGTCTTTCAGCAAGGACTGGTCTTTCTATCTCTTGTACTACACTGAATTCACCCCCACTGAAAAAGATGA

GTATGCCTGCCGTGTGAACCATGTGACTTTGTCACAGCCCAAGATAGTTAAGTGGGATCGAGACATGTAA

GCAGCATCATGGAGGTTTGAAGATGCCGCATTTGGATTGGATGAATTCCAAATTCTGCTTGCTTGCTTTT

TAATATTGATATGCTTATACACTTACACTTTATGCACAAAATGTAGGGTTATAATAATGTTAACATGGAC

ATGATCTTCTTTATAATTCTACTTTGAGTGCTGTCTCCATGTTTGATGTATCTGAGCAGGTTGCTCCACA

GGTAGCTCTAGGAGGGCTGGCAACTTAGAGGTGGGGAGCAGAGAATTCTCTTATCCAACATCAACATCTT

GGTCAGATTTGAACTCTTCAATCTCTTGCACTCAAAGCTTGTTAAGATAGTTAAGCGTGCATAAGTTAAC

TTCCAATTTACATACTCTGCTTAGAATTTGGGGGAAAATTTAGAAATATAATTGACAGGATTATTGGAAA
```

```
TTTGTTATAATGAATGAAACATTTTGTCATATAAGATTCATATTTACTTCTTATACATTTGATAAAGTAA

GGCATGGTTGTGGTTAATCTGGTTTATTTTTGTTCCACAAGTTAAATAAATCATAAAACTTGATGTGTTA

TCTCTTA
```

FcRn Binding Antibodies

DX2504 is an FcRn binding antibody that is described in WO2009/131702 and US-2009-0324614-A1. Both WO2009/131702 and US-2009-0324614-A1 are incorporated by reference into this application in their entirety. DX2504 was generated by a combination of monoclonal antibody technology and phage display experiments using FcRn polypeptides or cells expressing FcRn as the target. In addition, the sequence of DX2504 was germlined to lower immunogenicity. The sequences of DX2504 light chain and heavy chain are shown below:

Cysteine Mutants

The cysteine mutants of DX2504 described herein lack a cysteine residue at the first position of at least one CDR3, for example, the first position of the $V_L$ CDR3 of DX2504 being replaced with another amino acid residue such as Ala, Ser, or a conservative substitution thereof. Exemplary cysteine mutants include, but are not limited to, 532A-X53-C02 (having a $V_L$ set forth as SEQ ID NO:10) and 532A-X53-B03 (having a $V_L$ set forth as SEQ ID NO: 11). Such mutants preserve the FcRn-binding activity, e.g., binding to human FcRn with a dissociation constant ($K_D$) of less than 10 nM,

```
Light chain Variable Region (SEQ ID NO: 8):
FR1-L                       CDR1-L                  FR2-L         CDR2-L
QSALTQPASVSGSPGQSITISC TGTGSDVGSYNLVS WYQQHPGKAPKLMIY GDSQRPS FR3-L                      CDR3-L          FR4-L
GVSNRFSGSKSGNTASLTISGLQAEDEADYYC CSYAGSGIYV FGTGTKVTVL Light Chain Full Length (SEQ ID NO: 16; C_L underlined):
QSALTQPASVSGSPGQSITISCTGTGSDVGSYNLVSWYQQHPGKAPKLMIYGDSQRPSGVSNRFSGSKSGNTASL
TISGLQAEDEADYYCCSYAGSGIYVFGTGTKVTVLGQPKANPTVTLFPPSSEELQANKATLVCLISDFYPGAVTV
AWKADGSPVKAGVETTKPSKQSNNKYAASSYLSLTPEQWKSHRSYSCQVTHEGSTVEKTVAPTECS Heavy chain Variable Region (SEQ ID NO: 9):
        FR1-H                       CDR1-H  FR2-H              CDR2-H
EVQLLESGGGLVQPGGSLRLSCAASGFTFS EYAMG WVRQAPGKGLEWVS SIGSSGGQTKYADSVKG FR3-H                       CDR3-H     FR4-H
RFTISRDNSKNTLYLQMNSLRAEDTAVYYCAR LAIGDSY WGQGTMVTVSS Heavy Chain Full :Length (SEQ ID NO: 17; C_H underlined)
EVQLLESGGGLVQPGGSLRLSCAASGFTFSEYAMGWVRQAPGKGLEWVSSIGSSGGQTKYADSVKGRFTISRDNS

KNTLYLQMNSLRAEDTAVYYCARLAIGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICNVNHKPSNTKVDKRVEPKSCDKTHTC

PPCPAPELLGGPSVFLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCSVMHEALHNHYTQKSLSLSPGK
```

In addition to binding FcRn, DX2504, or precursor antibodies, has been shown to block the binding of IgG-Fc to FcRn expressing cells (Example 21 of WO2009/131702). Furthermore, administering DX2504 to Tg32B mice, a mouse in which the mouse FcRn is replaced by the human FcRn, lowered the levels of a human IgG which was administered to the mice previously (Example 27 of WO2009/131702). Moreover, the administration of DX2504 in cynomolgus monkeys resulted in the lowering of IgG serum levels (Example 27 of WO2009/131702).

It was unexpectedly found herein that altering either the CDR3 of the light chain (e.g., the cysteine mutants described herein) or the constant region of the heavy chain (e.g., the deletion mutants described herein) of DX2504 resulted in FcRn binding antibodies with improved properties when compared to DX2504. This finding was unexpected at least in part because, generally, an antibody that has gone through as many rounds of sequence optimization, such as DX2504, cannot be easily optimized further by introducing additional mutations.

which can be determined by a routine method. In some examples, the cysteine mutant contains two $V_L$ chains, either one or both of which do not have a cysteine at the first position of the $V_L$ CDR3 region.

The cysteine mutant described herein can comprise a $V_L$ chain, in which the CDR1, CDR2, and CDR3 share at least 70% (e.g., at least 75%, 80%, 85%, 90%, or 95%) sequence identity to the $V_L$ CDR1 and $V_L$ CDR2 of DX2504 (SEQ ID NOs: 14 and 15, respectively; identical to those in 532A-X53-C02 or 532A-X53-B03) and an altered $V_L$ CDR3 of DX2504 (SEQ ID NO:12 or 13, the $V_L$ CDR3 of 532A-X53-C02 or 532A-X53-B03). In some embodiments, one or more of the $V_L$ CDRs share at least 70% sequence identity to that of the corresponding CDR(s) of 532A-X53-C02 or 532A-X53-B03. For example, the cysteine mutant has at least 70% homology (at least 75%, 80%, 85%, 90%, or 95%) in the $V_L$ CDR3 region with the sequences SSYAGSGIYV (SEQ ID NO:12), or ASYAGSGIYV (SEQ ID NO:13).

In other embodiments, the $V_L$ CDRs of the cysteine mutant, in combination, share at least 70% sequence identity to those of 532A-X53-C02 or 532A-X53-B03, in combination. For example, an antibody with at least 90% homology in the CDR1, CDR2 and CDR3 region with the reference CDR sequences refers to an antibody that has at least 9 out of every 10 amino acids in the combined CDR1, CDR2 and CDR3 regions identical to the amino acids found in the combined CDR1, CDR2 and CDR3 regions of 532A-X53-C02.

Alternatively, the antibody can have up to 1, up to 2, up to 3, up to 4, or up to 5 amino acid substitutions in the $V_L$ CDR3 region as compared to the sequences SSYAGSGIYV (SEQ ID NO:12) or ASYAGSGIYV (SEQ ID NO:13). In some embodiments, the cysteine mutant can contain up to 3 substitutions in the $V_L$ CDR3 region as compared to the CDR3 region of DX2504. The one or more of the amino acids substitutions can be conservative amino acid substitutions.

Moreover, the cysteine mutant antibodies can have up to 1, up to 2, up to 3, up to 4, up to 5, up to 6, up to 7, up to 8, up to 9, up to 10, or up to 15 amino acid substitutions in the CDR1, CDR2 and CDR3 region as compared to the sequences of the CDR1, CDR2 and CDR3 regions of 532A-X53-C02 or 532A-X53-B03. In some embodiments, they can contain up to 10 substitutions in the $V_L$ CDR1, CDR2, and CDR3 regions collectively. In one example, the one or more of the amino acids substitutions are conservative amino acid substitutions.

In some embodiments, the cysteine mutant comprises a $V_L$ chain that share at least 70% (e.g., at least 75%, 80%, 85%, 90%, 95%, 97%, or 98%) sequence identity to the $V_L$ sequence of 532A-X53-C02 (SEQ ID NO:10) or that of 532A-X53-B03 (SEQ ID NO:11). In one example, the cysteine mutant comprises the same $V_L$ CDR3 region as 532A-X53-C02 or 532A-X53-B03, and optionally, the same $V_L$ CDR1 and CDR2 regions as the two exemplary mutants.

The "percent identity" of two amino acid sequences can be determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some embodiments, the cysteine mutants described herein can contain one or more mutations (e.g., conservative amino acid substitutions) within the framework regions (FRs) as compared to the two exemplary mutants described above and in Example 1 below. As known in the art, mutations within the FR regions are unlikely to affect the antigen-binding activity of the antibody. In other embodiments, the cysteine mutants described herein can contain one or more mutations (e.g., 1, 2, or 3 mutations such as conservative amino acid substitutions) within one or more of the CDR regions as compared to 532A-X53-C02 or that of 532A-X53-B03. Preferably, such mutants retain the same regions/residues responsible for antigen-binding as the parent, such as the same specificity-determining residues inside the CDRs.

Figure 2:
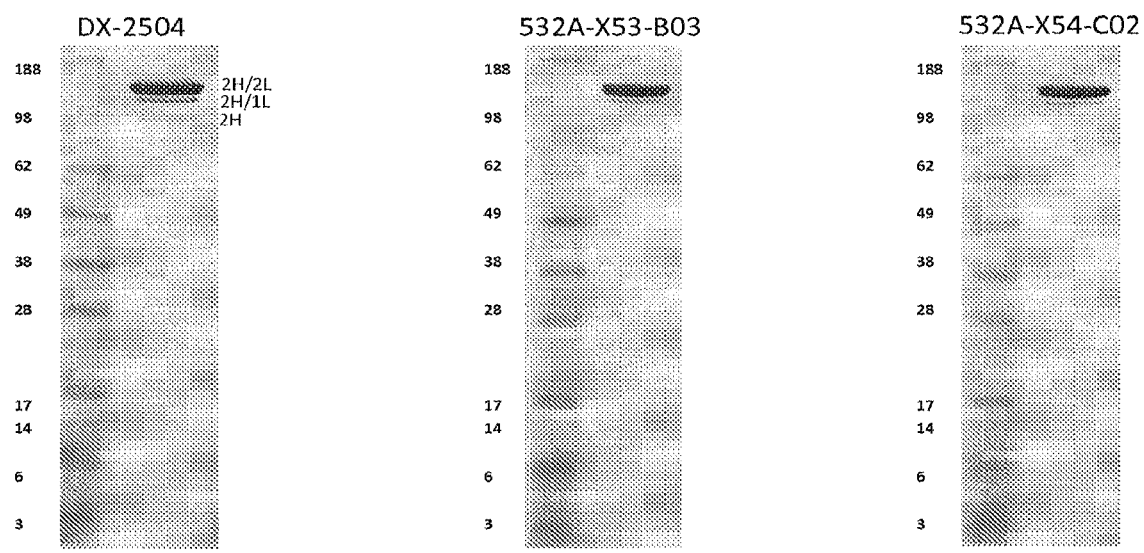
FIG. 2 shows an SDS-PAGE analysis of DX-2504, 532A-X53-C02 and 532A-X54-B03.
Figure 3:
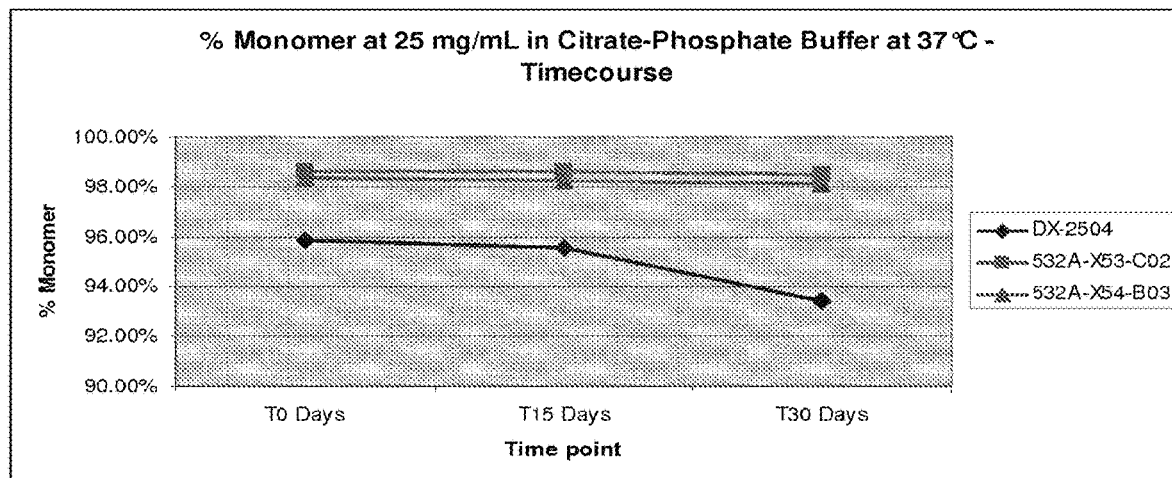
FIG. 3 shows the temperature stability of DX-2504, 532A-X53-C02 and 532A-X54-B03.
Figure 4:
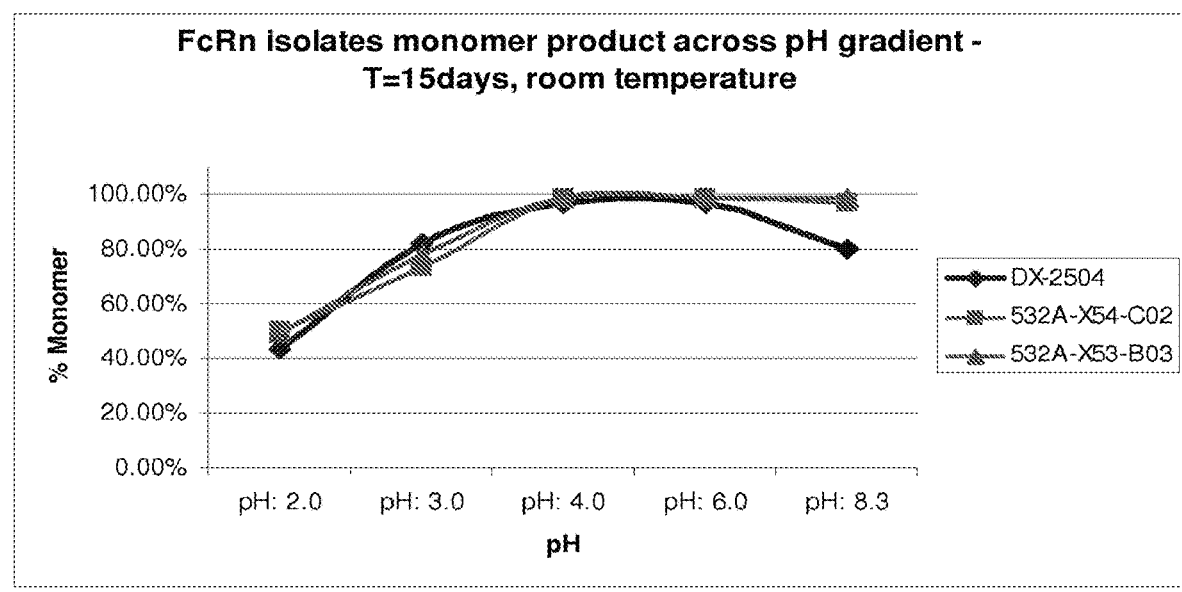
FIG. 4 shows the pH stability of DX-2504, 532A-X53-C02 and 532A-X54-B03.
Figure 7:
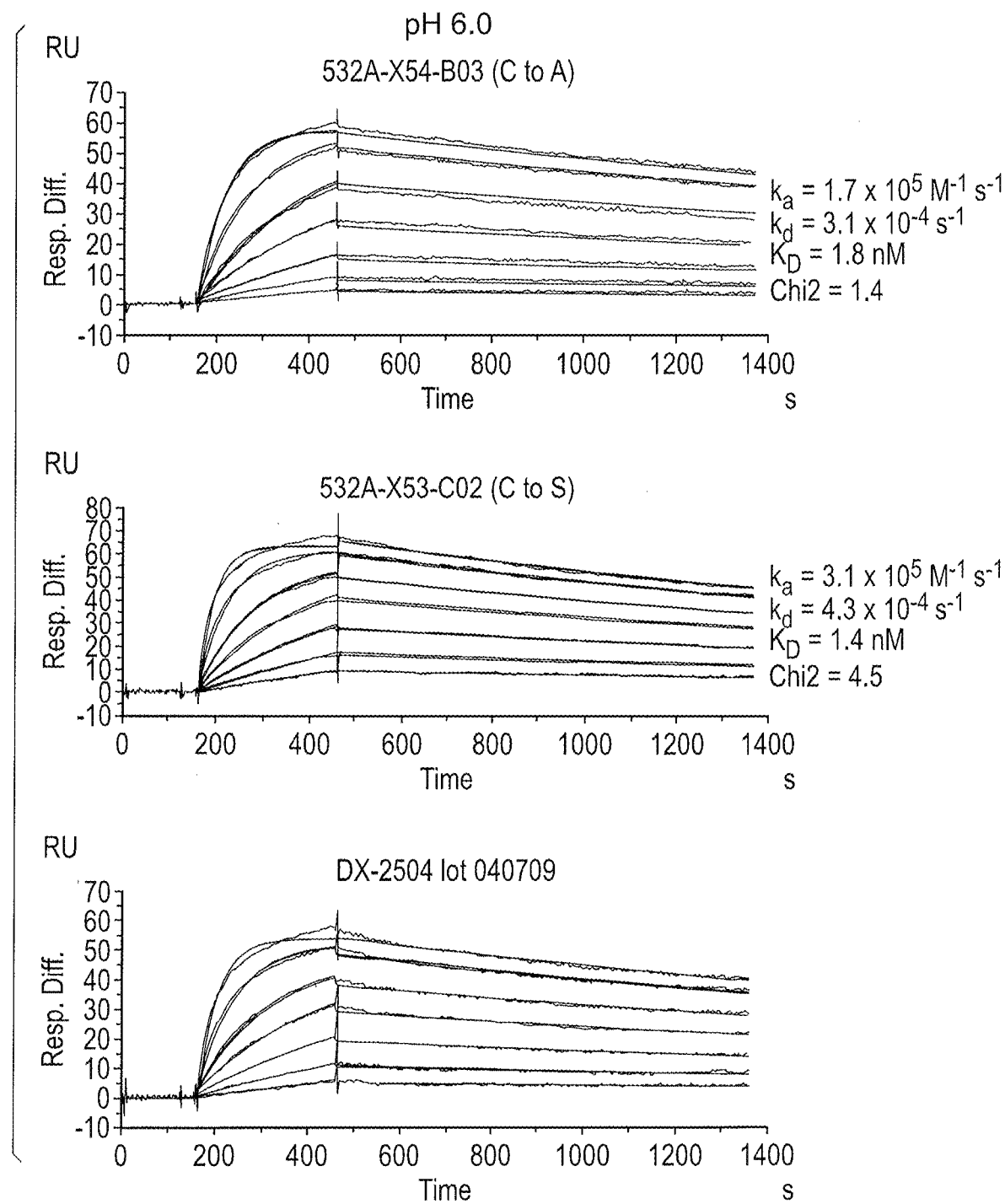
FIG. 7 shows the kinetic analysis of the interaction of hFcRn at pH6 with immobilized DX-2504, 532A-X53-C02 and 532A-X54-B03.
Figure 8:
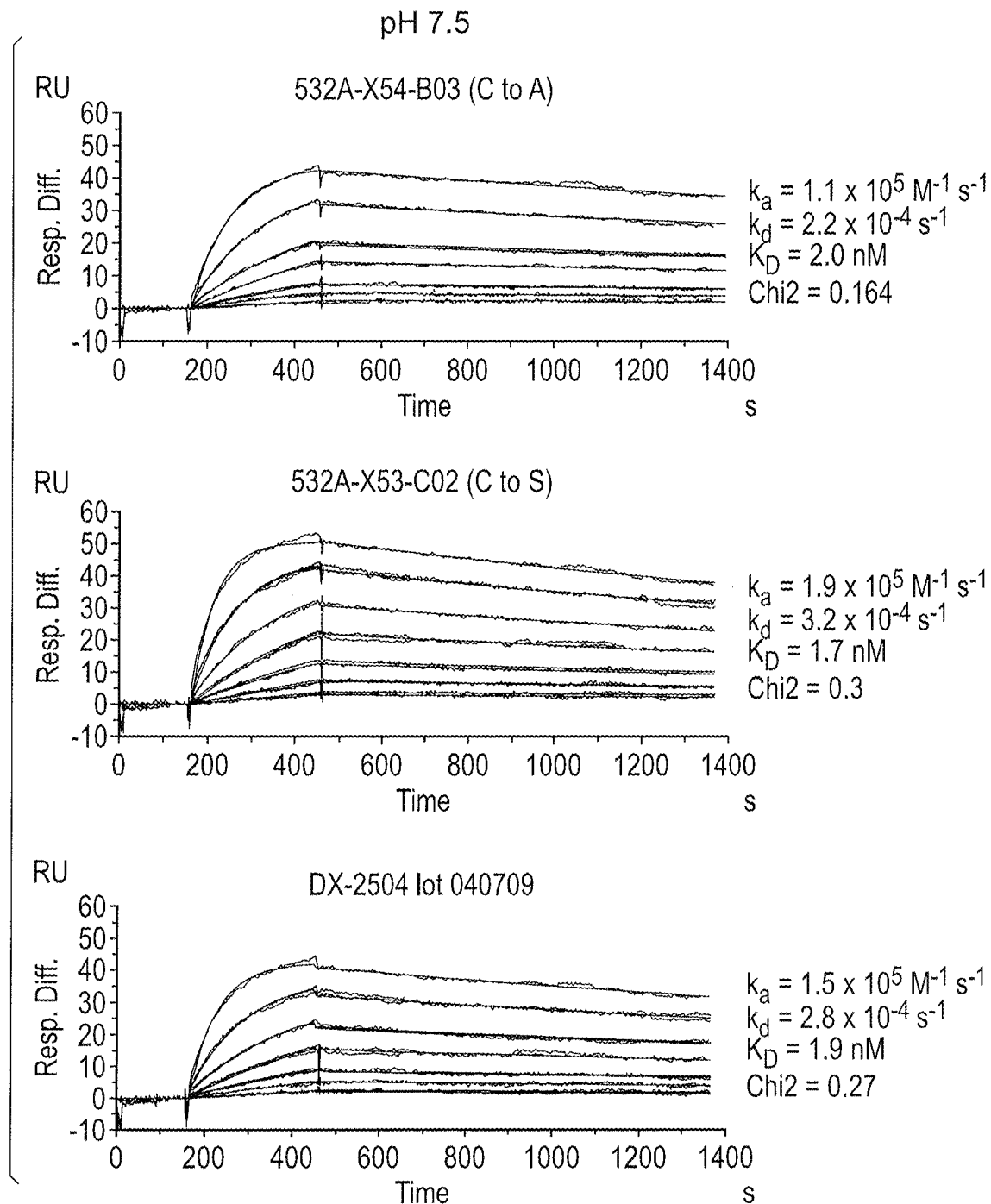
FIG. 8 shows the kinetic analysis of the interaction at pH7.5 of hFcRn with immobilized DX-2504, 532A-X53-C02 and 532A-X54-B03.
Figure 11:
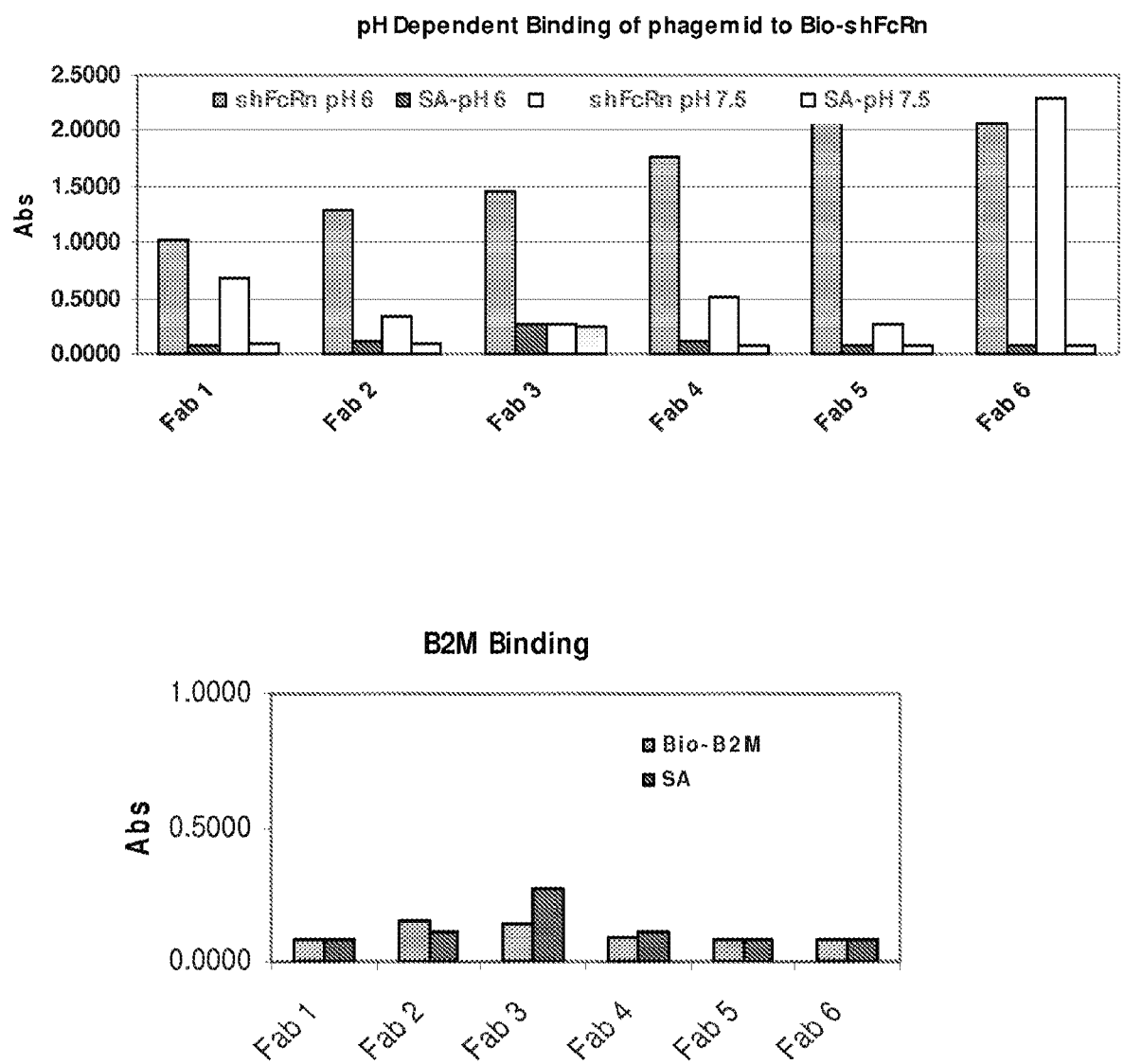
FIG. 11 shows two graphs characterizing some of the properties of selected anti-FcRn binding proteins.
Figure 12:
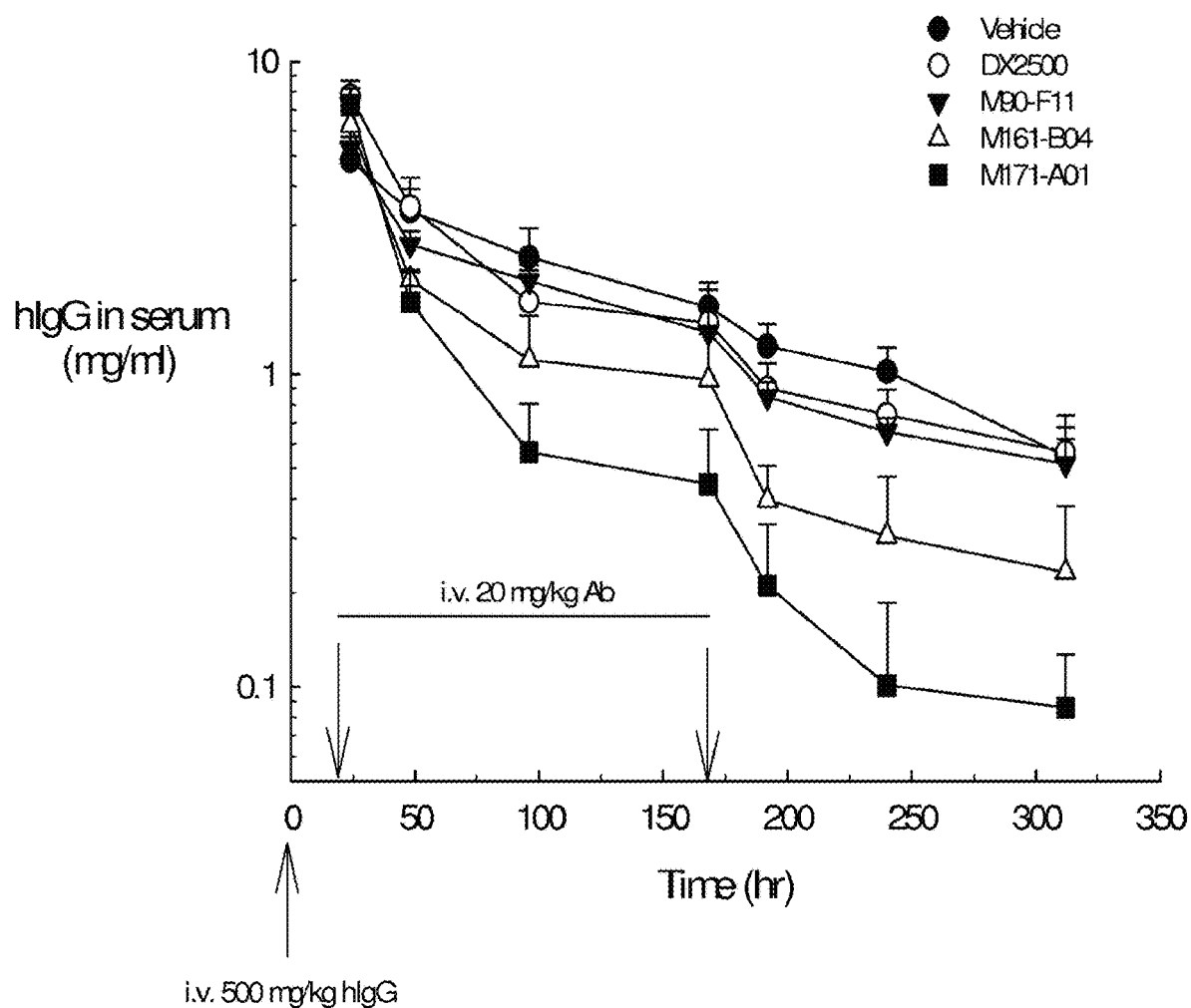
FIG. 12 shows the effect of anti-FcRn antibodies on the catabolism of hIgG in TG32B mice.

In general, a cysteine residue provides a protein with unique properties because a cysteine residue can form a covalent bond with other cysteines. Mutating a cysteine often results in proteins with significantly altered properties. It was therefore unexpected that the antibodies with the cysteine in CDR3 of light chain mutated to either a serine (C54-C02) or an alanine (X54-B03) were found to be more homogeneous than DX-2504, as measured by size exclusion chromatography (FIG. 1) and by SDS-PAGE analysis (FIG. 2). It was also unexpected that cysteine mutants would be more stable, with respect to the percent monomeric IgG species, over a 30 day incubation at 37° C. incubation (FIG. 3) or following a 15 day incubation at pH 8.3 (FIG. 4). Mutations in the CDRs of an antibody often diminish the affinity of antigen binding. It was therefore further unexpected that mutating a cysteine in the CDR3 of the light chain of DX-2504 did not affect the affinity of antigen binding (FIGS. 7 and 8).

Any of the cysteine mutants described above can further comprise a heavy chain variable region ($V_H$), which comprises $V_H$ CDR1, $V_H$ CDR2, and $V_H$ CDR3 regions. The $V_H$ can be the same as that of DX2504 (SEQ ID NO:9) or a functional variant thereof. In some embodiments, the $V_H$ CDRs in the functional variant share at least 70% (e.g., at least 75%, 80%, 85%, 90%, or 95%) sequence identity to those of DX2504 (SEQ ID NOs: 22, 23, and 24). In one example, one or more of the $V_H$ CDRs share at least 70% sequence identity to that of the corresponding $V_H$ CDR(s) of DX2504, for example, having at least 70% homology (at least 75%, 80%, 85%, 90%, or 95%) in the $V_H$ CDR3 region with the sequences LAIGDSY (SEQ ID NO:24).

In another example, the $V_H$ CDRs of the functional variant, in combination, share at least 70% sequence identity to those of DX2504, in combination. For example, an antibody with at least 90% homology in the CDR1, CDR2 and CDR3 region with the reference CDR sequences refers to an antibody that has at least 9 out of every 10 amino acids in the combined CDR1, CDR2 and CDR3 regions identical to the amino acids found in the combined CDR1, CDR2 and CDR3 regions of DX2504.

Alternatively, the functional mutant can contain up to 1, up to 2, up to 3, up to 4, or up to 5 amino acid substitutions in the CDR3 region as compared to the CDR3 sequences of DX2504 (LAIGDSY; SEQ ID NO:24). In some embodiments, the functional variants include up to 3 substitutions in the $V_H$ CDR3 region as compared to the CDR3 region of DX2504. In one example, the one or more of the amino acids substitutions are conservative amino acid substitutions.

Moreover, the functional variant can contain up to 1, up to 2, up to 3, up to 4, up to 5, up to 6, up to 7, up to 8, up to 9, up to 10, up to 11, up to 12, up to 13, up to 14, or up to 15 amino acid substitutions in the CDR1, CDR2 and CDR3 region as compared to the sequences of the CDR1, CDR2 and CDR3 regions of DX2504. In some embodiments, they contain up to 10 substitutions in the $V_H$ CDR1, CDR2, and CDR3 regions collectively. In one example, the one or more of the amino acids substitutions are conservative amino acid substitutions.

In some embodiments, the functional variant comprises a $V_H$ chain that share at least 70% (e.g., at least 75%, 80%, 85%, 90%, 95%, 97%, or 98%) sequence identity to the $V_H$ sequence of DX2504 (SEQ ID NO:9). In one example, the functional variant comprises the same $V_H$ CDR3 region as DX2504, and optionally, the same $V_H$ CDR1 and CDR2 regions as DX2504.

When desired, the functional variant of DX2504 heavy chain as described herein can contain one or more mutations (e.g., conservative amino acid substitutions) within the framework regions (FRs) of DX2504 (see above description). As known in the art, mutations within the FR regions are unlikely to affect the antigen-binding activity of the antibody. In other embodiments, the cysteine mutants described herein can contain one or more mutations (e.g., 1, 2, or 3 mutations such as conservative amino acid substitutions) within one or more of the CDR regions as compared to DX2504. Preferably, such variants retain the same regions/residues responsible for antigen-binding as the parent, such as the same specificity-determining residues inside the CDRs.

In one example, the cysteine mutant of DX2504 described herein comprises a light chain at least 70% (e.g., at least 75%, 80%, 85%, 90%, or 95%) homology with 532A-X53-C02 or 532A-X53-B03, and a heavy chain comprising the same CDRs as that of DX2504 (e.g., the same heavy chain variable region as that of DX2504). In another example, the mutant comprises the same $V_L$ as 532A-X53-C02 or 532A-X53-B03, and the same $V_H$ as DX2504.

Deletion Mutants

Figure 13:
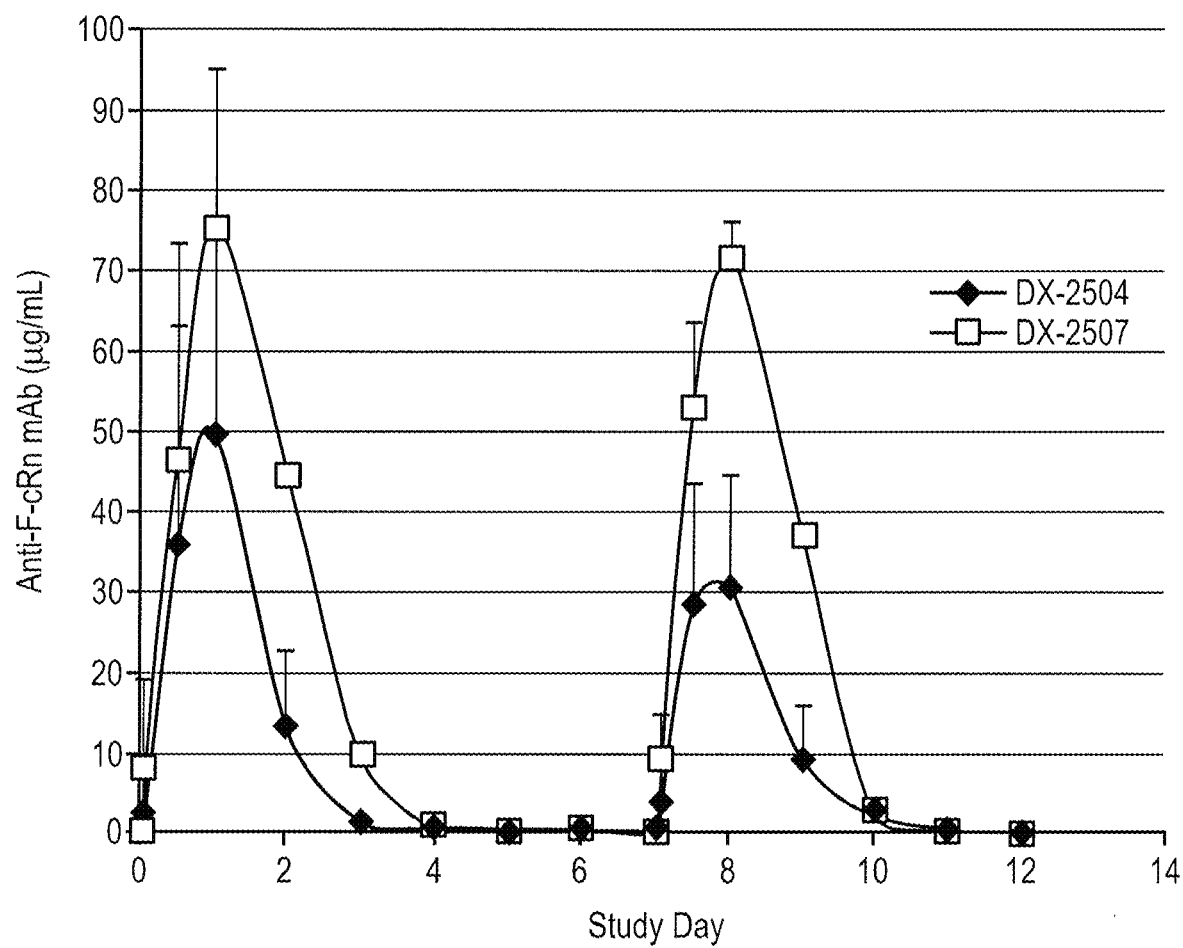
FIG. 13 shows serum concentrations of DX-2504 and DX-2507 administered to cynomolgus monkeys.
Figure 14:
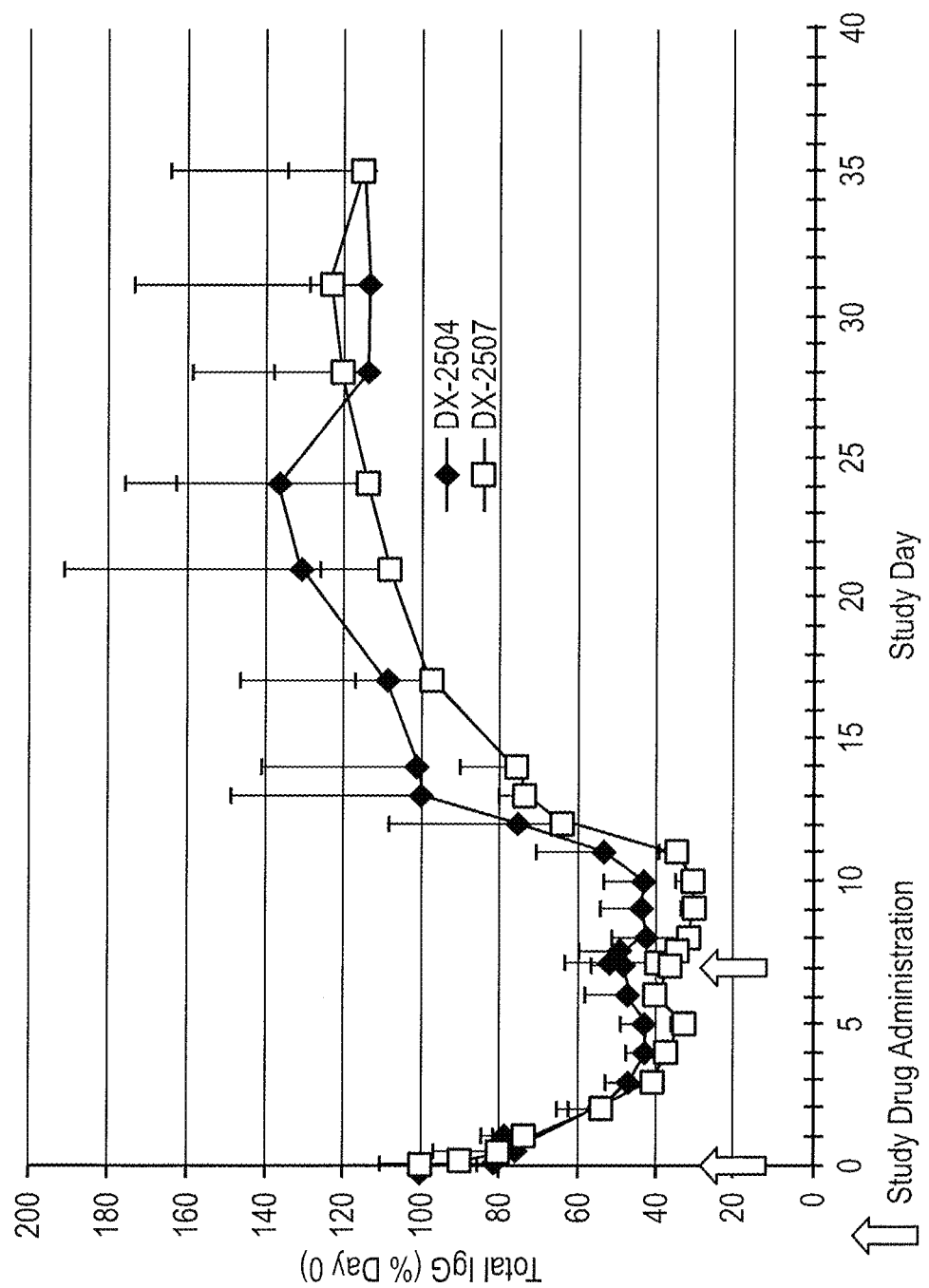
FIG. 14 shows IgG levels in cynomolgus monkeys following administration of DX-2504 and DX-2507.

It has also been discovered, unexpectedly, that the deletion of the C-terminal lysine residue of the heavy chain of DX2504 resulted in an anti-FcRn antibody (DX2507) having increased antibody retention and a higher reduction of IgG in an animal model as compared to DX2504 (FIGS. 13 and 14).

Accordingly, also described herein are deletion mutants that lack the C-terminal lysine residue in its heavy chain as compared to the heavy chain of DX2504. More specifically, the heavy chain of the deletion mutant described herein can be otherwise identical to the heavy chain of DX2504 (SEQ ID NO: 17) or to the heavy chain of any of the functional variants of DX2504 as described above except for the deletion of the amino acid residue corresponding to the C-terminal lysine residue in the heavy chain of DX2504 (SEQ ID NO:17). One example of such a heavy chain is that of DX2507 (SEQ ID NO:19) described in Example 2 below.

The deletion mutants described above can further comprise a light chain, which can comprise the $V_L$ region of DX2504 or the $V_L$ region of any of the cysteine mutants described herein.

In some examples, the deletion mutant comprises a light chain comprising the same $V_L$ CDRs as DX2504, 532A-X53-C02, or 532A-X53-B03 (e.g., the same $V_L$ as DX2504, 532A-X53-C02, or 532A-X53-B03), a heavy chain comprising the same $V_H$ CDRs as DX2504 (e.g., the same $V_H$ as DX2504) and a heavy chain constant region having a deletion at the position corresponding to the C-terminal lysine residue of the heavy chain of DX2504.

Any of the cysteine and deletion mutants described herein can bind to human FcRn with a dissociation constant ($K_D$) of less than 10 nM.

In addition to having the amino acids sequences described herein, the anti-FcRn antibodies described herein may have any structural framework. Thus, for instance the CDR1, CDR2, ad CDR3 regions described above, may be embedded in a "traditional" antibody framework, or may embedded in a scFv or Fab framework. The anti-FcRn antibody described herein can be a full-length antibody or an antigen-binding fragment thereof, e.g., Fab, F(ab)'2, Fv or ScFv antibody. It can be a non-human antibody such as a murine antibody (e.g., a monoclonal antibody produced by a hybridoma cell line), a chimeric antibody, or a humanized antibody.

Also within the scope of the present disclosure are nucleic acids comprising nucleotide sequences encoding the $V_H$ and/or $V_L$ of any of the anti-FcRn antibodies described herein (e.g., any of the cysteine mutants or any of the deletion mutants described above). Such nucleic acid sequences can be inserted into expression vectors, which can be introduced into suitable host cells (e.g., bacterial cells such as E. coli cells, yeast cells, insect cells, plant cells, or mammalian cells) for production of the anti-FcRn antibodies via recombinant technology.

Methods of Making Mouse Monoclonal Antibodies

Methods of making monoclonal antibodies have been described (Harlow et al., Antibodies A Laboratory Manual, Cold Spring Harbor Laboratory, Cold Spring Harbor, N.Y. (1988)). In some instances, as a first step, a rodent, e.g., a mouse is immunized with an antigenic polypeptide to generate an antibody response. Because FcRn is expressed ubiquitously and exhibits high degree of homology between species, polypeptide immunization has not been successful in producing high affinity FcRn specific monoclonal antibodies or FcRn monoclonal blocking antibodies. To solve this problem DNA vaccination can be performed (Castagliola et al., J. Immunology 160:1458 (1998)). DNA vaccination involves immunizing a rodent, e.g., a mouse with a cDNA construct encoding FcRn or a fragment thereof. Immunization can be administered intramuscularly, intraperitoneally, subcutaneously, intravenously, intradermally or directly into the lymph node. In one embodiment the immunizations administered intramuscularly. DNA vaccination can be administered with an adjuvant, e.g. Freunds complete adjuvant or Freund's incomplete adjuvant. The DNA vaccination can be accompanied by administration of a cardiotoxin to increase the antibody titer. Administration of a cardiotoxin causes cell death and cell regeneration which enhances cellular uptake of the administered DNA vaccine. The cardiotoxin can also increase inflammation which results in a more robust immune response.

Antibody secreting cells (B cells) are isolated from the rodent. Typically the B cell can be isolated from the rodents spleen and fused with a myeloma cell line. The myeloma cell lines are immortalized cell lines that do not produce antibodies. The myeloma cell line can be chosen from, but is not limited to P3-X63Ag8, X63Ag8.653, Sp2/0-Ag14, FO, NSI/1-Ag4-1, NSO/1, FOX-NY, Y3-Ag1.2.3, YB2/0 and IR983F.

Splenocytes are fused with the myeloma cell line to form a hybridoma. Fusion can be mediated by mixing the two cell types with polyethylene glycol for an appropriate period of time (e.g. five minutes). The formed hybridomas are grown in cell culture using an appropriate selection media (e.g. HAT) and screened for their ability to produce a monoclonal antibody against FcRn. Screening can be performed using known immunological techniques, e.g. an ELISA.

Another approach to making FcRn specific monoclonal antibodies is to immunize a transgenic FcRn knockout mouse with soluble human FcRn, see, PCT Application WO 02/43658. WO 02/43658 describes a transgenic mouse whose genome comprises a homozygous disruption in its endogenous FcRn gene, wherein said homozygous disruption prevents expression of a functional FcRn protein. The monoclonal antibody of the invention is not made in a transgenic mouse whose genome comprises a homozygous disruption in its endogenous FcRn gene, wherein said homozygous disruption prevents expression of a functional FcRn protein. The monoclonal antibody of the invention is not comprised of a B cell from a transgenic mouse whose genome comprises a homozygous disruption in its endogenous FcRn gene, wherein said homozygous disruption prevents expression of a functional FcRn protein.

Humanized Anti-FcRn Antibodies Display Libraries

A display library can be used to identify antibodies that bind to the FcRn. A display library is a collection of entities; each entity includes an accessible polypeptide component and a recoverable component that encodes or identifies the polypeptide component. The polypeptide component is varied so that different amino acid sequences are represented. The polypeptide component can be of any length, e.g. from three amino acids to over 300 amino acids. In a selection, the polypeptide component of each member of the library is probed with the FcRn and if the polypeptide component binds to the FcRn, the display library member is identified, typically by retention on a support. In addition, a display library entity can include more than one polypeptide component, for example, the two polypeptide chains of an sFab.

Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component and purification of the polypeptide component for detailed characterization.

A variety of formats can be used for display libraries. Examples include the following.

Phage Display. One format utilizes viruses, particularly bacteriophages. This format is termed "phage display." The protein component is typically covalently linked to a bacteriophage coat protein. The linkage results from translation of a nucleic acid encoding the protein component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibody Hybridomas* 3:81-85; Huse et al. (1989) *Science* 246:1275-1281; Griffiths et al. (1993) *EMBO J* 12:725-734; Hawkins et al. (1992). *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; and Hoogenboom et al. (1991) *Nuc Acid Res* 19:4133-4137.

Phage display systems have been developed for filamentous phage (phage f1, fd, and M13) as well as other bacteriophage. The filamentous phage display systems typically use fusions to a minor coat protein, such as gene III protein, and gene VIII protein, a major coat protein, but fusions to other coat proteins such as gene VI protein, gene VII protein, gene IX protein, or domains thereof can also been used (see, e.g., WO 00/71694). In one embodiment, the fusion is to a domain of the gene III protein, e.g., the anchor domain or "stump," (see, e.g., U.S. Pat. No. 5,658,727 for a description of the gene III protein anchor domain). It is also possible to physically associate the protein being displayed to the coat using a non-peptide linkage.

Bacteriophage displaying the protein component can be grown and harvested using standard phage preparatory methods, e.g., PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

Other Display Formats. Other display formats include cell based display (see, e.g., WO 03/029456), protein-nucleic acid fusions (see, e.g., U.S. Pat. No. 6,207,446), and ribosome display (See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30; and Schaffitzel et al. (1999) *J Immunol Methods.* 231(1-2):119-35).

Scaffolds. Scaffolds for display can include: antibodies (e.g., Fab fragments, single chain Fv molecules (scFV), single domain antibodies, camelid antibodies, and camelized antibodies); T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin and heat shock proteins; intracellular signaling domains (such as SH2 and SH3 domains); linear and constrained peptides; and linear peptide substrates. Display libraries can include synthetic and/or natural diversity. See, e.g., US 2004-0005709.

Display technology can also be used to obtain antibodies that bind particular epitopes of a target. This can be done, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library members that are not specific to the target.

Iterative Selection. In one embodiment, display library technology is used in an iterative mode. A first display library is used to identify one or more antibodies that bind a target. These identified antibodies are then varied using a mutagenesis method to form a second display library. Higher affinity antibodies are then selected from the second library, e.g., by using higher stringency or more competitive binding and washing conditions.

In some implementations, the mutagenesis is targeted to regions known or likely to be at the binding interface. In the case of antibodies, the mutagenesis can be directed to the CDR regions of the heavy or light chains as described herein. Further, mutagenesis can be directed to framework regions near or adjacent to the CDRs. In the case of antibodies, mutagenesis can also be limited to one or a few of the CDRs, e.g., to make precise step-wise improvements. Exemplary mutagenesis techniques include: error-prone PCR, recombination, DNA shuffling, site-directed mutagenesis and cassette mutagenesis.

In one example of iterative selection, the methods described herein are used to first identify an antibody from a display library that binds an FcRn with at least a minimal binding specificity for a target or a minimal activity, e.g., an equilibrium dissociation constant for binding of less than 1 nM, 10 nM, or 100 nM. The nucleic acid sequence encoding the initial identified antibodies are used as a template nucleic acid for the introduction of variations, e.g., to identify a second antibody that has enhanced properties (e.g., binding affinity, kinetics, or stability) relative to the initial antibody.

Off-Rate Selection. Since a slow dissociation rate can be predictive of high affinity, particularly with respect to interactions between antibodies and their targets, the methods described herein can be used to isolate antibodies with a desired kinetic dissociation rate (e.g., reduced) for a binding interaction to a target.

To select for slow dissociating antibodies from a display library, the library is contacted to an immobilized target. The immobilized target is then washed with a first solution that removes non-specifically or weakly bound biomolecules. Then the bound antibodies are eluted with a second solution that includes a saturating amount of free target or a target specific high-affinity competing monoclonal antibody, i.e., replicates of the target that are not attached to the particle. The free target binds to biomolecules that dissociate from the target. Rebinding is effectively prevented by the saturating amount of free target relative to the much lower concentration of immobilized target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

Selecting or Screening for Specificity. The display library screening methods described herein can include a selection or screening process that discards display library members that bind to a non-target molecule. Examples of non-target molecules include streptavidin on magnetic beads, blocking agents such as bovine serum albumin, non-fat bovine milk, any capturing or target immobilizing monoclonal antibody, or non-transfected cells which do not express the human FcRn target.

In one implementation, a so-called "negative selection" step is used to discriminate between the target and related non-target molecule and a related, but distinct non-target molecules. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target as well as for cross species reactivity to related targets or subunits of the target (e.g., rat FcRn; β2 microglobulin) and also under different condition such as pH6 or pH 7.5. The non-target and target binding data are compared (e.g., using a computer and software) to identify library members that specifically bind to the target.

Other Expression Libraries

Other types of collections of proteins (e.g., expression libraries) can be used to identify proteins with a particular property (e.g., ability to bind FcRn and/or ability to modulate FcRn), including, e.g., protein arrays of antibodies (see, e.g., De Wildt et al. (2000) Nat. Biotechnol. 18:989-994), lambda gt11 libraries, two-hybrid libraries and so forth.

Antibody Libraries

In one embodiment, the library presents a diverse pool of polypeptides, each of which includes an immunoglobulin domain, e.g., an immunoglobulin variable domain. Display libraries are particularly useful, for example, for identifying human or "humanized" antibodies that recognize human antigens. Such antibodies can be used as therapeutics to treat human disorders such as autoimmune disorders. Because the constant and framework regions of the antibody are human, these therapeutic antibodies may avoid themselves being recognized and targeted as antigens. The constant regions may also be optimized to recruit effector functions of the human immune system. The in vitro display selection process surmounts the inability of a normal human immune system to generate antibodies against self-antigens.

A typical antibody display library displays a polypeptide that includes a VH domain and a $V_L$ domain. An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay, 1988, *Ann. Rev. Immunol.* 6:381-405). The display library can display the antibody as a Fab fragment (e.g., using two polypeptide chains) or a single chain Fv (e.g., using a single polypeptide chain). Other formats can also be used.

As in the case of the Fab and other formats, the displayed antibody can include one or more constant regions as part of a light and/or heavy chain. In one embodiment, each chain includes one constant region, e.g., as in the case of a Fab. In other embodiments, additional constant regions are displayed.

Antibody libraries can be constructed by a number of processes (see, e.g., de Haard et al., 1999, *J. Biol. Chem.* 274:18218-30; Hoogenboom et al., 1998, *Immunotechnology* 4:1-20; and Hoogenboom et al., 2000, *Immunol. Today* 21:371-378. Further, elements of each process can be combined with those of other processes. The processes can be used such that variation is introduced into a single immunoglobulin domain (e.g., $V_H$ or $V_L$) or into multiple immunoglobulin domains (e.g., $V_H$ and $V_L$). The variation can be introduced into an immunoglobulin variable domain, e.g., in the region of one or more of CDR1, CDR2, CDR3, FR1, FR2, FR3, and FR4, referring to such regions of either and both of heavy and light chain variable domains. In one embodiment, variation is introduced into all three CDRs of a given variable domain. In another embodiment, the variation is introduced into CDR1 and CDR2, e.g., of a heavy chain variable domain. Any combination is feasible. In one process, antibody libraries are constructed by inserting diverse oligonucleotides that encode CDRs into the corresponding regions of the nucleic acid. The oligonucleotides can be synthesized using monomeric nucleotides or trinucleotides. For example, Knappik et al., 2000, *J. Mol. Biol.* 296:57-86 describe a method for constructing CDR encoding oligonucleotides using trinucleotide synthesis and a template with engineered restriction sites for accepting the oligonucleotides.

In another process, an animal, e.g., a rodent, is immunized with the FcRn. The animal is optionally boosted with the antigen to further stimulate the response. Then spleen cells are isolated from the animal, and nucleic acid encoding $V_H$ and/or $V_L$ domains is amplified and cloned for expression in the display library.

In yet another process, antibody libraries are constructed from nucleic acid amplified from naïve germline immunoglobulin genes. The amplified nucleic acid includes nucleic acid encoding the $V_H$ and/or $V_L$ domain. Sources of immunoglobulin-encoding nucleic acids are described below. Amplification can include PCR, e.g., with primers that anneal to the conserved constant region, or another amplification method.

Nucleic acid encoding immunoglobulin domains can be obtained from the immune cells of, e.g., a human, a primate, mouse, rabbit, camel, llama or rodent. In one example, the cells are selected for a particular property. B cells at various stages of maturity can be selected. In another example, the B cells are naïve.

In one embodiment, fluorescent-activated cell sorting (FACS) is used to sort B cells that express surface-bound IgM, IgD, or IgG molecules. Further, B cells expressing different isotypes of IgG can be isolated. In another embodiment, the B or T cell is cultured in vitro. The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohaemagglutinin, or pokeweed mitogen.

In still one embodiment, the cells are isolated from a subject that has an autoimmune disorder, e.g., systemic lupus erythematosus (SLE), rheumatoid arthritis, vasculitis, Sjogren syndrome, systemic sclerosis, or anti-phospholipid syndrome. The subject can be a human, or an animal, e.g., an animal model for the human disease, or an animal having an analogous disorder. In yet one embodiment, the cells are isolated from a transgenic non-human animal that includes a human immunoglobulin locus.

In one embodiment, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al., 2001, *J. Immunol.* 166:2228). In one embodiment, the cells are naïve.

The nucleic acid encoding an immunoglobulin variable domain can be isolated from a natural repertoire by the following exemplary method. First, RNA is isolated from the immune cell. Full length (i.e., capped) mRNAs are separated (e.g., by degrading uncapped RNAs with calf intestinal phosphatase). The cap is then removed with tobacco acid pyrophosphatase and reverse transcription is used to produce the cDNAs.

The reverse transcription of the first (antisense) strand can be done in any manner with any suitable primer. See, e.g., de Haard et al., 1999, *J. Biol. Chem.* 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. In one embodiment, poly-dT primers may be used (and may be preferred for the heavy-chain genes).

A synthetic sequence can be ligated to the 3' end of the reverse transcribed strand. The synthetic sequence can be used as a primer binding site for binding of the forward primer during PCR amplification after reverse transcription. The use of the synthetic sequence can obviate the need to use a pool of different forward primers to fully capture the available diversity.

The variable domain-encoding gene is then amplified, e.g., using one or more rounds. If multiple rounds are used, nested primers can be used for increased fidelity. The amplified nucleic acid is then cloned into a display library vector.

Secondary Screening Methods

After selecting candidate library members that bind to a target, each candidate library member can be further analyzed, e.g., to further characterize its binding properties for the target. Each candidate library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. Exemplary assays for binding properties include the following.

ELISA. Antibodies selected from an expression library can also be screened for a binding property using an ELISA. For example, each antibody is contacted to a microtitre plate whose bottom surface has been coated with the target, e.g., a limiting amount of the target. The plate is washed with buffer to remove non-specifically bound polypeptides. Then the amount of the antibody bound to the plate is determined by probing the plate with an antibody that can recognize the test antibody, e.g., a tag or constant portion of the antibody. The detection antibody is linked to an enzyme such as alkaline phosphatase or horse radish peroxidase (HRP) which produces a colorimetric product when appropriate substrates are provided.

In the case of an antibody from a display library, the antibody can be purified from cells or assayed in a display library format, e.g., as a fusion to a filamentous bacteriophage coat. In another version of the ELISA, each antibody selected from an expression library is used to coat a different well of a microtitre plate. The ELISA then proceeds using a constant target molecule to query each well.

Homogeneous Binding Assays. The binding interaction of candidate antibody with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means well known in the art (e.g., using a fluorimeter). By titrating the amount of the first or second binding molecule, a binding curve can be generated to estimate the equilibrium binding constant.

Another example of a homogenous assay is ALPHASCREEN™ (Packard Bioscience, Meriden Conn.). ALPHASCREEN™ uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding.

The homogenous assays can be performed while the candidate polypeptide is attached to the display library vehicle, e.g., a bacteriophage.

Surface Plasmon Resonance (SPR). The binding interaction of a molecule isolated from an expression library and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether, 1988, Surface Plasmons Springer Verlag; Sjolander and Urbaniczky, 1991, *Anal. Chem.* 63:2338-2345; Szabo et al., 1995, *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_d$), and kinetic parameters, including $K_{on}$ and $K_{off}$, for the binding of a biomolecule to a target. Such data can be used to compare different biomolecules. For example, selected proteins from an expression library can be compared to identify proteins that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

Cellular Assays. A library of candidate antibodies (e.g., previously identified by a display library or otherwise) can be screened for target binding on cells which transiently or stably express and display the target of interest on the cell surface. For example, the target can include vector nucleic acid sequences that include segments that encode only the extracellular portion of the polypeptides such that the chimeric target polypeptides are produced within the cell, secreted from the cell, or attached to the cell surface through the anchor e.g., in fusion with a membrane anchoring proteins such as Fc. The cell surface expressed target can be used for screening antibodies that bind to FcRn and block the binding of IgG-Fc. For example, non-specific human IgG-Fc could be fluorescently labeled and its binding to FcRn in the presence of absence of antagonistic antibody can be detected by a change in fluorescence intensity using flow cytometry e.g., a FACS machine.

Other Methods for Obtaining FcRn-Binding Antibodies

In addition to the use of display libraries, other methods can be used to obtain a FcRn-binding antibody. For example, the FcRn protein or a region thereof can be used as an antigen in a non-human animal, e.g., a rodent.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies (Mabs) derived from the genes with the desired specificity may be produced and selected. See, e.g., XENOMOUSE™, Green et al., 1994, *Nat. Gen.* 7:13-21; U.S. 2003-0070185, WO 96/34096, published Oct. 31, 1996, and PCT Application No. PCT/US96/05928, filed Apr. 29, 1996.

In one embodiment, a monoclonal antibody is obtained from the non-human animal, and then modified, e.g., humanized or deimmunized. Winter describes a CDR-grafting method that may be used to prepare the humanized antibodies (UK Patent Application GB 2188638A, filed on Mar. 26, 1987; U.S. Pat. No. 5,225,539. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above. The recombinant DNA encoding the humanized antibody, or fragment thereof, can then be cloned into an appropriate expression vector.

An FcRn-binding antibody may also be modified by specific deletion of human T cell epitopes or "deimmunization" by the methods disclosed in WO 98/52976 and WO 00/34317, the contents of which are specifically incorporated by reference herein. Briefly, the heavy and light chain variable regions of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions or by single amino acid substitutions. As far as possible conservative substitutions are made, often but not exclusively, an amino acid common at this position in human germline antibody sequences may be used. Human germline sequences are disclosed in Tomlinson, I. A. et al., 1992, *J. Mol. Biol.* 227:776-798; Cook, G. P. et al., 1995, *Immunol. Today* Vol. 16 (5): 237-242; Chothia, D. et al., 1992, *J. Mol. Bio.* 227:799-817. The V BASE directory provides a comprehensive directory of human immunoglobulin variable region sequences (compiled by Tomlinson, I. A. et al. MRC Centre for Protein Engineering, Cambridge, UK). After the deimmunizing changes are identified, nucleic acids encoding $V_H$ and $V_L$ can be constructed by mutagenesis or other synthetic methods (e.g., de novo synthesis, cassette replacement, and so forth). Mutagenized variable sequence can, optionally, be fused to a human constant region, e.g., human IgG1 or K constant regions.

In some cases, a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs were eliminated by substitutions outside the CDRs. In some cases, an alteration within a CDR is the only option, and thus variants with and without this substitution should be tested. In other cases, the substitution required to remove a potential T cell epitope is at a residue position within the framework that might be critical for antibody binding. In these cases, variants with and without this substitution should be tested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

Germlining Antibodies.

An antibody used to treat an IgG-mediated autoimmune disease can be used for multiple administrations. Precautions that would lower the immunogenicity of the therapeutic antibody include reverting one or more non-germline amino acids in framework regions to corresponding germline amino acids (e.g., so long as binding properties are substantially retained) of the antibody (especially of Fabs).

It is possible to modify an antibody that binds FcRn, e.g., an antibody described herein, in order to make the variable regions of the antibody more similar to one or more germline sequences. For example, an antibody can include one, two, three, or more amino acid substitutions, e.g., in a framework, CDR, or constant region, to make it more similar to a reference germline sequence. One exemplary germlining method can include identifying one or more germline sequences that are similar (e.g., most similar in a particular database) to the sequence of the isolated antibody. Mutations (at the amino acid level) can then be made in the isolated antibody, either incrementally or in combination with other mutations. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a framework and/or constant region. For example, a germline framework and/or constant region residue can be from a germline sequence that is similar (e.g., most similar) to the non-variable region being modified. After mutagenesis, activity (e.g., binding or other functional activity) of the antibody can be evaluated to determine if the germline residue or residues are tolerated (i.e., do not abrogate activity). Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may including using two germline sequences that separately contribute to the amino-terminal portion and the carboxy-terminal portion. In other implementations more than one or two germline sequences are used, e.g., to form a consensus sequence.

In one embodiment, with respect to a particular reference variable domain sequence, e.g., a sequence described herein, a related variable domain sequence has at least 30, 40, 50, 60, 70, 80, 90, 95 or 100% of the CDR amino acid positions that are not identical to residues in the reference CDR sequences, residues that are identical to residues at corresponding positions in a human germline sequence (i.e., an amino acid sequence encoded by a human germline nucleic acid).

In one embodiment, with respect to a particular reference variable domain sequence, e.g., a sequence described herein, a related variable domain sequence has at least 30, 50, 60, 70, 80, 90 or 100% of the FR regions are identical to FR sequence from a human germline sequence, e.g., a germline sequence related to the reference variable domain sequence.

Accordingly, it is possible to isolate an antibody which has similar activity to a given antibody of interest, but is more similar to one or more germline sequences, particularly one or more human germline sequences. For example, an antibody can be at least 90, 91, 92, 93, 94, 95, 96, 97, 98, 99, or 99.5% identical to a germline sequence in a region outside the CDRs (e.g., framework regions). Further, an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity) can be within a factor or 100, 10, 5, 2, 0.5, 0.1, and 0.001 of the original antibody.

Exemplary germline reference sequences for $V_{kappa}$ include: O12/O2, O18/O8, A20, A30, L14, L1, L15, L4/18a, L5/L19, L8, L23, L9, L24, L11, L12, O11/O1, A17, A1, A18, A2, A19/A3, A23, A27, A11, L2/L16, L6, L20, L25, B3, B2, A26/A10, and A14. See, e.g., Tomlinson et al., 1995, *EMBO J.* 14(18):4628-3.

A germline reference sequence for the HC variable domain can be based on a sequence that has particular canonical structures, e.g., 1-3 structures in the H1 and H2 hypervariable loops. The canonical structures of hypervariable loops of an immunoglobulin variable domain can be inferred from its sequence, as described in Chothia et al., 1992, *J. Mol. Biol.* 227:799-817; Tomlinson et al., 1992, *J. Mol. Biol.* 227:776-798); and Tomlinson et al., 1995, *EMBO J.* 14(18):4628-38. Exemplary sequences with a 1-3 structure include: DP-1, DP-8, DP-12, DP-2, DP-25, DP-15, DP-7, DP-4, DP-31, DP-32, DP-33, DP-35, DP-40, 7-2, hv3005, hv3005f3, DP-46, DP-47, DP-58, DP-49, DP-50, DP-51, DP-53, and DP-54.

Ligand Production

Standard recombinant nucleic acid methods can be used to express an antibody that binds to FcRn. Generally, a nucleic acid sequence encoding the antibody is cloned into a nucleic acid expression vector. Of course, if the antibody includes multiple polypeptide chains, each chain can be cloned into an expression vector, e.g., the same or different vectors, that are expressed in the same or different cells.

Antibody Production. Some antibodies, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al., 2001, *J. Immunol. Methods.* 251:123-35), Hanseula, or *Saccharomyces*.

In one embodiment, antibodies are produced in mammalian cells. Mammalian host cells for expressing the clone antibodies or antigen-binding fragments thereof include Chinese Hamster Ovary (CHO cells) (including dhfr− CHO cells, described in Urlaub and Chasin, 1980, *Proc. Natl. Acad. Sci. USA* 77:4216-4220, used with a DHFR selectable marker, e.g., as described in Kaufman and Sharp, 1982, *Mol. Biol.* 159:601 621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr− CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, *Adv. Immunol.* 51:1-84; Jefferis et al., 1998, *Immunol. Rev.* 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

One method for producing a transgenic mouse is as follows. Briefly, a targeting construct that encodes the antibody is microinjected into the male pronucleus of fertilized oocytes. The oocytes are injected into the uterus of a pseudopregnant foster mother for the development into viable pups. Some offspring incorporate the transgene.

Assay Systems for FcRn Candidate Antibodies

FcRn candidate antibodies can be further characterized in assays that measure their modulatory activity toward FcRn or fragments thereof in vitro or in vivo. For example, FcRn can be combined with a substrate such as non-specific IgG or Fc portion of the IgG or albumin under assay conditions permitting reaction of the FcRn with the substrate. The assay is performed in the absence of the FcRn candidate antibody, and in the presence of increasing concentrations of the FcRn candidate antibody. The concentration of candidate antibody at which 50% of the FcRn activity (e.g., binding to the substrate) is inhibited by the candidate antibody is the $IC_{50}$ value (Inhibitory Concentration 50%) or $EC_{50}$ (Effective Concentration 50%) value for that antibody. Within a series or group of candidate antibodies, those having lower $IC_{50}$ or $EC_{50}$ values are considered more potent inhibitors of FcRn than those antibodies having higher $IC_{50}$ or $EC_{50}$ values. In some embodiments, antibodies have an $IC_{50}$ value of 800 nM, 400 nM, 100 nM, 25 nM, 5 nM, 1 nM, or less as measured in an in vitro assay for inhibition of FcRn activity.

The candidate antibodies can also be evaluated for selectivity toward FcRn. For example, a FcRn candidate antibody can be assayed for its potency toward FcRn and a panel of cell surface receptors, such as receptors that also utilize the β2M domain, and an $IC_{50}$ value or $EC_{50}$ value can be determined for each receptor protein. In one embodiment, a compound that demonstrates a low $IC_{50}$ value or $EC_{50}$ value for the FcRn, and a higher $IC_{50}$ value or $EC_{50}$ value for other receptors within the test panel (e.g., MHC class I molecules) is considered to be selective toward FcRn.

Ex vivo endothelial cells or epithelial cells expressing the endogenous FcRn could be used to follow the endocytosis or transcytosis of the candidate antibodies under different pH and temperature conditions. IgG transcytosis or recycling by FcRn can be measured by following a labeled antibody in the presence or absence of various chemicals and under different conditions that are known to influence or affect the intracellular trafficking pathway.

A pharmacokinetics study in rat, mice, or monkey could be performed with pH dependent and independent FcRn binding antibodies for determining their half-life in the serum. Likewise, the protective effect of the antibody can be assessed in vivo for potential use in immunomodulating therapy or as an salvage immunotherapy by injecting the antibody in the presence or absence of a labeled IgG or the labeled Fc portion of the IgG. A decrease in the half-life of the labeled IgG/Fc in the presence of the candidate antibody is an indication of the therapeutic efficacy of the antibody.

Pharmaceutical Compositions

In another aspect, the disclosure provides compositions, e.g., pharmaceutically acceptable compositions or pharmaceutical compositions, which include an FcRn-binding antibody. The FcRn-binding antibody can be formulated together with a pharmaceutically acceptable carrier. Pharmaceutical compositions include therapeutic compositions and diagnostic compositions, e.g., compositions that include labeled FcRn-binding antibodies for in vivo imaging.

A pharmaceutically acceptable carrier includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal, or epidermal administration (e.g., by injection or infusion). Depending on the route of administration, the FcRn-binding antibody may be coated in a material to protect the compound from the action of acids and other natural conditions that may inactivate the compound.

A pharmaceutically acceptable salt is a salt that retains the desired biological activity of the parent compound and does not impart any undesired toxicological effects (see e.g., Berge, S. M., et al., 1977, *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like.

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Many compositions are in the form of injectable or infusible solutions, such as compositions similar to those used for administration of humans with antibodies. An exemplary mode of administration is parenteral (e.g., intravenous, subcutaneous, intraperitoneal, intramuscular). In one embodiment, the FcRn-binding antibody is administered by intravenous infusion or injection. In another embodiment, the FcRn-binding antibody is administered by intramuscular or subcutaneous injection.

The composition can be formulated as a solution, microemulsion, dispersion, liposome, or other ordered structure suitable to high drug concentration. Sterile injectable solutions can be prepared by incorporating the active compound (i.e., the ligand) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An FcRn-binding antibody can be administered by a variety of methods known in the art, although for many applications, the route/mode of administration is intravenous injection or infusion. For example, for therapeutic applications, the FcRn-binding antibody can be administered by intravenous infusion at a rate of less than 30, 20, 10, 5, or 1 mg/min to reach a dose of about 1 to 100 mg/m$^2$ or 7 to 25 mg/m$^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., 1978, Marcel Dekker, Inc., New York.

In certain embodiments, the antibody may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound disclosed herein by other than parenteral administration, it may be necessary to coat the compound with, or co-administer the compound with, a material to prevent its inactivation.

Pharmaceutical compositions can be administered with medical devices known in the art. For example, in one embodiment, a pharmaceutical composition disclosed herein can be administered with a device, e.g., a needleless hypodermic injection device, a pump, or implant.

In certain embodiments, an FcRn-binding antibody can be formulated to ensure proper distribution in vivo. For example, the blood-brain barrier (BBB) excludes many highly hydrophilic compounds. To ensure that the therapeutic compounds disclosed herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade, 1989, *J. Clin. Pharmacol.* 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody disclosed herein is 0.1-20 mg/kg, or 1-10 mg/kg. An anti-FcRn antibody can be administered, e.g., by intravenous infusion, e.g., at a rate of less than 30, 20, 10, 5, or 1 mg/min to reach a dose of about 1 to 100 mg/m$^2$ or about 5 to 30 mg/m$^2$. Dosage values may vary with the type and severity of the condition to be alleviated. For a particular subject, specific dosage regimens can be adjusted over time according to the individual need and the professional judgment of the person administering or supervising the administration of the compositions.

The pharmaceutical compositions disclosed herein may include a therapeutically effective amount or a prophylactically effective amount of an FcRn-binding antibody disclosed herein. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the antibody to elicit a desired response in the individual. A therapeutically effective amount is also one in which any toxic or detrimental effects of the composition is outweighed by the therapeutically beneficial effects.

Stabilization and Retention

In one embodiment, an FcRn-binding antibody is physically associated with a moiety that improves its stabilization and/or retention in circulation, e.g., in blood, serum, lymph, or other tissues, e.g., by at least 1.5, 2, 5, 10, or 50 fold. For example, an FcRn-binding antibody can be associated with a polymer, e.g., a substantially non-antigenic polymers, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used. For example, an FcRn-binding antibody can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

Kits

An FcRn-binding antibody described herein can be provided in a kit, e.g., as a component of a kit. For example, the kit includes (a) an FcRn-binding antibody, e.g., a composition that includes an FcRn-binding antibody, and, optionally (b) informational material. The informational material can be descriptive, instructional, marketing or other material that relates to the methods described herein and/or the use of an FcRn-binding antibody for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to using the antibody to treat, prevent, or diagnosis a disorder described herein, e.g., an autoimmune disorder.

In one embodiment, the informational material can include instructions to administer an FcRn-binding antibody in a suitable manner to perform the methods described herein, e.g., in a suitable dose, dosage form, or mode of administration (e.g., a dose, dosage form, or mode of administration described herein). In one embodiment, the informational material can include instructions to administer an FcRn-binding antibody to a suitable subject, e.g., a human, e.g., a human having, or at risk for, an autoimmune disorder (e.g., rheumatoid arthritis or systemic lupus erythematosis). For example, the material can include instructions to administer an FcRn-binding antibody to a patient with lupus or a patient with another autoimmune disorder.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In one embodiment, the informational material of the kit is contact information, e.g., a physical address, email address, website, or telephone number, where a user of the kit can obtain substantive information about an FcRn-binding antibody and/or its use in the methods described herein. Of course, the informational material can also be provided in any combination of formats.

In addition to an FcRn-binding antibody, the composition of the kit can include other ingredients, such as a solvent or buffer, a stabilizer, a preservative, a flavoring agent (e.g., a bitter antagonist or a sweetener), a fragrance or other cosmetic ingredient, and/or a second agent for treating an autoimmune disorder described herein, e.g., rheumatoid arthritis or systemic lupus erythematosis. Alternatively, the other ingredients can be included in the kit, but in different compositions or containers than an FcRn-binding antibody.

In such embodiments, the kit can include instructions for admixing an FcRn-binding antibody and the other ingredients, or for using an FcRn-binding antibody together with the other ingredients.

An FcRn-binding antibody can be provided in any form, e.g., liquid, dried or lyophilized form. It is preferred that an FcRn-binding antibody be substantially pure and/or sterile. When an FcRn-binding antibody is provided in a liquid solution, the liquid solution preferably is an aqueous solution, with a sterile aqueous solution being preferred. When an FcRn-binding antibody is provided as a dried form, reconstitution generally is by the addition of a suitable solvent. The solvent, e.g., sterile water or buffer, can optionally be provided in the kit.

The kit can include one or more containers for the composition containing an FcRn-binding antibody. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an FcRn-binding antibody. For example, the kit includes a plurality of syringes, ampules, foil packets, or blister packs, each containing a single unit dose of an FcRn-binding antibody. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In one embodiment, the device is an implantable device that dispenses metered doses of the antibody. The disclosure also features a method of providing a kit, e.g., by combining components described herein.

Treatments

Antibodies that bind to FcRn and identified by the method described herein and/or detailed herein have therapeutic and prophylactic utilities. These antibodies can be administered to a subject to treat, prevent, and/or diagnose a variety of disorders, including autoimmune disorders, or even to cells in culture, e.g., in vitro or ex vivo.

The term "treating" refers to administering a therapy in an amount, manner, and/or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the subject. The subject can be a human or a non-human animal, e.g., a non-human mammal.

The FcRn-binding antibody can be administered in a therapeutically effective amount, e.g., such that upon single or multiple dose administration to a subject, the subject exhibits an amelioration of symptoms of a disorder, e.g., an autoimmune disorder (e.g., rheumatoid arthritis or systemic lupus erythematosis) or of a parameter indicative of presence or risk for the disorder.

Exemplary disorders which affect many organs or localized organs in the body include: Multiple Sclerosis, rheumatoid arthritis, inflammatory bowel diseases (IBD), lupus, and ankylosing spondylitis. Some of these disorders are discussed below. In one aspect, the invention provides methods for the treatment of cancer. Still other disorders that can be treated using an FcRn-binding antibody include: scleroderma, Sjogren's syndrome, Goodpasture's syndrome, Wegener's granulomatosis, polymyalgia rheumatica, temporal arteritis/gian cell arteritis, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, CREST Syndrome, Crohn's disease, Dego's disease, dermatomyositis, juvenile dermatomyositis, discoid lupus, essential mixed cryoglobulinemia, fibromyalgia, fibromyositis, Grave's disease, Guillain-Barre syndrome, Hashimoto's thyroiditis, idiopathic pulmonary fibrosis, idiopathic thrombocytopenia purpura (ITP), IgA nephropathy, insulin dependent diabetes (Type I), juvenile arthritis, Meniere's disease, mixed connective tissue disease, myasthenia gravis, pemphigus vulgaris, pemphigus foliaceus, paraneoplastic pemphigus, pernicious anemia, polyarteritis nodosa, polychondritis, polyglancular syndromes, polymyalgia rheumatica, polymyositis, dermatomyositis, primary agammaglobulinemia, primary biliary cirrhosis, psoriasis, Raynaud's phenomenon, Reiter's syndrome, rheumatic fever, sarcoidosis, stiff-man syndrome, Takayasu arteritis, ulcerative colitis, uveitis, vasculitis, vitiligo.

In some embodiments, the anti-FcRn binding antibody is administered to remove an unwanted therapeutic antibody from the bloodstream.

In some embodiments, the anti-FcRn binding antibody is administered to suppress the level of anti-HLA antibodies. In some embodiments the level of anti-HLA antibodies is suppressed in connection with organ transplant.

Methods of administering FcRn-binding antibodies are described in "Pharmaceutical Compositions." Suitable dosages of the molecules used will depend on the age and weight of the subject and the particular drug used. The antibodies can be used as competitive agents to inhibit or reduce an undesirable interaction, e.g., between a natural or pathological agent and the FcRn.

The FcRn binding antibody can be used to deliver macro and micromolecules, e.g., a gene into the cell for gene therapy purposes into the endothelium or epithelium and target only those tissues expressing the FcRn. The antibodies may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short range radiation emitters, including, for example, short range, high energy α-emitters, as described herein.

In the case of polypeptide toxins, recombinant nucleic acid techniques can be used to construct a nucleic acid that encodes the antibody and the cytotoxin (or a polypeptide component thereof) as translational fusions. The recombinant nucleic acid is then expressed, e.g., in cells and the encoded fusion polypeptide isolated.

Alternatively, the FcRn-binding antibody can be coupled to high energy radiation emitters, for example, a radioisotope, such as $^{131}I$, a γ-emitter, which, when localized at a site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303 316 (Academic Press 1985). Other suitable radioisotopes include a emitters, such as $^{212}$Bi, m$^{213}$Bi, and $^{211}$At, and b emitters, such as $^{186}$Re and $^{90}$Y. Moreover, $^{177}$Lu may also be used as both an imaging and cytotoxic agent.

Radioimmunotherapy (RIT) using antibodies labeled with $^{131}$I, $^{90}$Y, and $^{177}$Lu is under intense clinical investigation. There are significant differences in the physical characteristics of these three nuclides and as a result, the choice of radionuclide is very critical in order to deliver maximum radiation dose to a tissue of interest. The higher beta energy particles of $^{90}$Y may be good for bulky tumors. The relatively low energy beta particles of $^{131}$I are ideal, but in vivo dehalogenation of radioiodinated molecules is a major disadvantage for internalizing antibody. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the residence times are higher. As a result, higher activities (more mCi amounts) of $^{177}$Lu labeled agents can be administered with comparatively less radiation dose to marrow. There have been several clinical studies investigating the use of $^{17}$Lu labeled antibodies in the treatment of various cancers. (Mulligan T et al., 1995, *Clin. Canc. Res.* 1: 1447-1454; Meredith R F, et al., 1996, *J. Nucl. Med.* 37:1491-1496; Alvarez R D, et al., 1997, *Gynecol. Oncol.* 65: 94-101).

Use of the therapeutic methods to treat autoimmunity has a number of benefits. Since the antibodies specifically recognize FcRn, other tissue is spared and high levels of the agent are delivered directly to the site where therapy is required. Treatment can be effectively monitored with clinical parameters. Alternatively, these parameters can be used to indicate when such treatment should be employed.

An FcRn-binding antibody can be administered in combination with one or more of the existing modalities for treating autoimmune disorders including, but not limited to: intravenous Ig therapy, nonsteroidal anti-inflammatory drugs (NSAID), and corticosteroids; and anti-inflammatory treatments such as cyclosporins, rapamycins or ascomycins, or their immunosuppressive analogs, e.g., cyclosporin A, cyclosporin G, FK-506, rapamycin, 40-O-(2-hydroxy)ethyl-rapamycin etc.; cyclophosphamide; azathioprene; methotrexate; brequinar; FTY 720; leflunomide; mnizoribine; mycophenolic acid; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD45, or CD58 or their ligands; or other immunomodulatory compounds, e.g., CTLA4Ig, or other adhesion molecule inhibitors, e.g. mAbs or low molecular weight inhibitors including selectin antagonists and VLA-4 antagonists. These combination therapies can be part of an immunomodulating regimens or a regimen for the treatment or prevention of allo- or xenograft acute or chronic rejection, an inflammatory disorder, or an autoimmune disorders.

Multiple Sclerosis

Multiple sclerosis (MS) is a central nervous system disease that is characterized by inflammation and loss of myelin sheaths.

Patients having MS may be identified by criteria establishing a diagnosis of clinically definite MS as defined by the workshop on the diagnosis of MS (Poser et al., Ann. Neurol. 13:227, 1983). MS may also be diagnosed by evidence of two attacks and oligoclonal bands of IgG in cerebrospinal fluid or by combination of an attack, clinical evidence of two lesions and oligoclonal band of IgG in cerebrospinal fluid. The McDonald criteria can also be used to diagnose MS. McDonald et al. (2001) *Recommended diagnostic criteria for multiple sclerosis: guidelines from the International Panel on the Diagnosis of Multiple Sclerosis*, Ann Neurol 50:121-127. The McDonald criteria include the use of MRI evidence of CNS impairment over time to be used in diagnosis of MS, in the absence of multiple clinical attacks.

Effective treatment of multiple sclerosis may be evaluated in several different ways. The following parameters can be used to gauge effectiveness of treatment. Two exemplary criteria include: EDSS (extended disability status scale), and appearance of exacerbations on MRI (magnetic resonance imaging). The EDSS is a means to grade clinical impairment due to MS (Kurtzke, Neurology 33:1444, 1983). Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to MS). A decrease of one full step can indicate an effective treatment (Kurtzke, Ann. Neurol. 36:573-79, 1994).

Exemplary symptoms associated with multiple sclerosis, which can be treated with the methods described herein, include: optic neuritis, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, muscle atrophy, spasms, cramps, hypotonia, clonus, myoclonus, myokymia, restless leg syndrome, footdrop, dysfunctional reflexes, paraesthesia, anaesthesia, neuralgia, neuropathic and neurogenic pain, l'hermitte's, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgasmy, frigidity, constipation, fecal urgency, fecal incontinence, depression, cognitive dysfunction, dementia, mood swings, emotional lability, euphoria, bipolar syndrome, anxiety, aphasia, dysphasia, fatigue, uhthoff's symptom, gastroesophageal reflux, and sleeping disorders.

In addition to or prior to human studies, an animal model can be used to evaluate the efficacy of using the two agents. An exemplary animal model for multiple sclerosis is the experimental autoimmune encephalitis (EAE) mouse model, e.g., as described in (Tuohy et al. (J. Immunol. (1988) 141: 1126-1130), Sobel et al. (J. Immunol. (1984) 132: 2393-2401), and Traugott (Cell Immunol. (1989) 119: 114-129). Mice can be administered a first and second agent described herein prior to EAE induction. Then the mice are evaluated for characteristic criteria to determine the efficacy of using the two agents in the model.

Inflammatory Bowel Disease

Inflammatory bowel diseases (IBD) include generally chronic, relapsing intestinal inflammation. IBD refers to two distinct disorders, Crohn's disease and ulcerative colitis (UC). The clinical symptoms of IBD include intermittent rectal bleeding, crampy abdominal pain, weight loss and diarrhea. A clinical index can also be used to monitor IBD such as the Clinical Activity Index for Ulcerative Colitis.

See also, Walmsley et al. Gut. 1998 July; 43(1):29-32 and Jowett et al. (2003) Scand J Gastroenterol. 38(2):164-71. An FcRn-binding antibody can be used to ameliorate at least one symptom of IBD or to ameliorate a clinical index of IBD.

Rheumatoid Arthritis

Rheumatoid arthritis is an autoimmune inflammatory disease that causes pain, swelling, stiffness, and loss of function in the joints. Rheumatoid arthritis often presents in a symmetrical pattern. The disease can affect the wrist joints and the finger joints closest to the hand. It can also affect other parts of the body besides the joints. In addition, people with rheumatoid arthritis may have fatigue, occasional fevers, and a general malaise. Positive factors for diagnosis of rheumatoid arthritis include the "rheumatoid factor" blood antibody and citrulline antibody. An FcRn-binding antibody can be useful in treating, preventing, or alleviating rheumatoid arthritis or one or more symptoms of rheumatoid arthritis.

Lupus

Systemic lupus erythematosus (SLE) is an autoimmune disorder that leads to inflammation and damage to various body tissues. SLE can be mediated by self-antibodies directed against its own DNA. Lupus can affect many parts of the body, including the joints, skin, kidneys, heart, lungs, blood vessels, and brain. Although various symptoms may present, some of the most common include extreme fatigue, painful or swollen joints (arthritis), unexplained fever, skin rashes, and kidney problems. Exemplary symptoms of lupus include painful or swollen joints, unexplained fever, and extreme fatigue. A characteristic red skin rash may appear across the nose and cheeks. Rashes may also occur on the face and ears, upper arms, shoulders, chest, and hands. Other symptoms of lupus include chest pain, hair loss, anemia, mouth ulcers, and pale or purple fingers and toes from cold and stress. Some people also experience headaches, dizziness, depression, confusion, or seizures. Positive factors for SLE diagnosis include circulating anti-nuclear antibodies, anti-DNA antibodies, and anti-Sm antibodies. An FcRn-binding antibody can be useful in treating, preventing, or alleviating SLE or one or more symptoms of SLE. Lupus, as used herein includes cutaneous lupus and lupus nephritis.

Immune Thromocytopenia (ITP)

ITP is a disease of increased peripheral platelet destruction, where patients develop antibodies that bind to specific platelet membrane proteins. The anti-platelet antibodies opsonize the platelets, leading to destruction by macrophages. Attempts to treat ITP have generally involved suppressing the immune system, which causes an increase in platelet levels. An FcRn-binding antibody can be useful in treating, preventing, or alleviating ITP, or one or more symptoms thereof.

Ankylosing Spondylitis

Ankylosing spondylitis is an autoimmune disorder that not only affects the spine, but may also affect the hips, shoulders, and knees as the tendons and ligaments around the bones and joints become inflamed, resulting in pain and stiffness. Ankylosing spondylitis tends to affect people in late adolescence or early adulthood. An FcRn-binding antibody can be useful in treating, preventing, or alleviating ankylosing spondylitis, or one or more symptoms thereof.

Pemphigus

Pemphigus is an autoimmune disorder that affects mucous membranes and the skin. The disorder is characterized by the generation of auto-antibodies against desmoglein. Desmoglein is a protein in the family of cadherins and is involved with the formation of desmosomes, which join cells to one another. Pemphigus can be classified as one of three types: pemphigus vulgaris, the most common form of the disorder, wherein auto-antibodies target desmoglein 3. In pemphigusfolicaeus auto-antibodies against desmoglein 1 are generated. The third type, and least common disorder is paraneoplastic pemphigus, wherein autoantibodies target desmoplakins and which is associated with cancers such as lymphoma. The disorders are commonly diagnosed by a dermatologist by the appearance of the skin and is conformed by the detection of auto-antibodies against desmoglein. Methods of treatment include the administration of steroids and/or the administration of a CD20 antibody such as Rituximab (Rituxan)

Cancer

"Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Carcinomas are malignant cancers that arise from epithelial cells and include adenocarcinoma and squamous cell carcinoma. Sarcomas are cancer of the connective or supportive tissue and include osteosarcoma, chondrosarcoma and gastrointestinal stromal tumor. Hematopoietic cancers, such as leukemia, are able to outcompete the normal hematopoietic compartments in a subject, thereby leading to hematopoietic failure (in the form of anemia, thrombocytopenia and neutropenia) ultimately causing death. A person of ordinary skill in the art can classify a cancer as a sarcoma, carcinoma or hematopoietic cancer.

Cancer, as used herein, includes the following types of cancer, breast cancer, biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chromic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastoma; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will be known to one of ordinary skill in the art.

Treatment of Fetuses

FcRn mediates the transport of maternal IgG across epithelial cell barriers to fetus. The antibodies described herein can be used to deliver macromolecular drugs, e.g., antibiotics, and/or small molecules to fetuses in utero. The fetus may be suffering from a condition or disorder (e.g., an enteric infection or metabolic disorder) that requires treatment. The drug or molecule for treating the condition or disorder can be conjugated to a FcRn binding antibody and administered to a pregnant woman who has an in utero fetus that is in need of treatment. The conjugated FcRn-binding antibody binds to FcRn and is thereby transported to the fetus via the placenta. The fetus receives the drug or molecule treatment.

Immunadsorption

In some embodiments, the invention provides methods for the removal of an unwanted therapeutic antibody from an individual. In some embodiments, the unwanted therapeutic antibody is an IgG antibody. In some embodiments the unwanted therapeutic antibody is an anti-VLA4 antibody such as Natalizumab (Tysabri, Biogen Idec/Elan), efalizumab (Raptiva, Genentech), bevacizumab (Avastin, Genentech) and Fc fusion proteins such as etanercept (Enbrel, Amgen/Wyeth). Natalizumab monoclonal antibody therapy has been associated with Progressive Multifocal Leukoencephalopathy (PML). Depletion of the therapeutic antibody from the bloodstream and/or the rest of the body may alter the progression of PML.

In some embodiments, the treatment methods presented herein may be combined with methods to remove or partially remove therapeutic antibodies from the bloodstream of a subject. In some embodiments, the anti-FcRn antibodies presented herein may be combined with a capture protein that can bind a therapeutic antibody, resulting in an increased clearance of the therapeutic antibody from the bloodstream. In some embodiments, the method of removal or partial removal of the therapeutic antibody from the bloodstream of a subject is plasma exchange (PLEX). In some embodiments, the anti-FcRn antibodies can be administered to a subject undergoing plasma exchange. In some embodiments, the anti-FcRn antibodies can be used as an immunoadsorbant for FcRn in the plasma exchange process.

In plasma exchange (also called apheresis or plasmapheresis) blood is taken from the body and plasma containing an unwanted agent, such as cholesterol or a therapeutic antibody, is removed from the blood by a cell separator. Blood can be removed from the body in batches or it can be removed in a continuous flow mode, with the latter allowing for the reintroduction of the processed blood into the body. The removed plasma comprising the unwanted agent can be discarded and the patient can receive donor plasma or saline with added proteins in return. In some embodiments, multiple rounds of plasma exchange may be needed to remove the unwanted agent from the blood or to lower the level of the unwanted agent in the blood to an acceptable level. In some embodiments the blood is "filtered" and the unwanted agent removed, before returning the blood to the patient. Methods of plasma exchange are known in the art and are described, for example, in U.S. Pat. No. 6,960,178.

Plasma exchange has been shown to reduce therapeutic antibody levels in the blood of a subject and the restoration of homeostasis (See e.g., Khatri et al; 2009; Neurology 72:402-409).

An IgG based therapeutic antibody (such as natalizumab) can be removed from blood, plasma or serum by contacting the blood with the capture protein Staphylococcal protein A, which will bind the Fc region of IgG and remove the IgG antibody from the bloodstream. Other capture proteins can be used for different isotype antibodies. In some embodiments, the anti-FcRn antibodies can be used as a capture protein in the plasma exchange process, resulting in the removal of FcRn from the bloodstream, thereby increasing the amount of "free" therapeutic antibody. The resulting "free" therapeutic antibody will have a shorter half-life than antibody present prior to treatment and/or can be removed from the blood more readily with a different capture protein (such as protein A). In some embodiments, the anti-FcRn antibodies are administered to a patient during or before plasma exchange. In some embodiments, the anti-FcRn antibodies can be immobilized and used in a column, resulting in the binding of FcRn. In some embodiments, the blood of a patient that contains a therapeutic antibody is contacted both with immobilized anti-FcRn antibody and immobilized protein A.

In some embodiments the anti-FcRn antibodies presented herein can be used in "rescue" therapy for therapeutic antibodies that have been administered and have shown an adverse effect. In some embodiments, an anti-FcRn antibody can be used as an alternative for plasma exchange. The administration of an anti-FcRn can accomplish therapeutic antibody depletion without the risks associated with plasmapheresis and plasma exchange such as vascular access, citrate therapy and donor plasma sourcing.

Human Leukocyte Antigens

Human leukocyte antigens (HLA) present peptides and antigens on the outside of the cell, which are subsequently recognized by T-cells, which in their turn can activate B-cells. The panel of HLA genes available is unique for each person. Any cell displaying an HLA that is "non-self" will result in the induction of an immune response. In general, the more different the "non-self" HLA from the self HLA, the stronger the immune response. For instance, in the case of organ transplants, subjects with similar HLA genes are preferred to minimize the immune response. Donor-specific HLA antibodies have been found to be associated with graft failure in kidney, heart, lung and liver transplantation.

In some embodiments, the invention provides methods for the decreasing the level of "non-self" HLA antibodies in an individual. Decreasing the level of "non-self" HLA antibodies can result in the suppression of an immune response, e.g., during organ transplantation. In some embodiments a person that will be undergoing organ transplation is administered an anti-FcRn antibody. In some embodiments a person that is undergoing organ transplation is administered an anti-FcRn antibody. In some embodiments a person that has received an organ transplation is administered an anti-FcRn antibody. Assays for measuring the levels of HLA antibodies are well-known in the art.

Diagnostic Uses

Antibodies that bind to FcRn and identified by the method described herein and/or detailed herein have in vitro and in vivo diagnostic utilities.

In one aspect, the disclosure provides a diagnostic method for detecting the presence of an FcRn, in vitro or in vivo (e.g., in vivo imaging in a subject). The method can include localizing FcRn to a subcellular location, e.g., the endosome. The method can include: (i) contacting a sample with FcRn-binding antibody; and (ii) detecting formation of a complex between the FcRn-binding antibody and the sample. The method can also include contacting a reference sample (e.g., a control sample) with the antibody, and determining the extent of formation of the complex between the antibody and the sample relative to the same for the reference sample. A change, e.g., a statistically significant change, in the formation of the complex in the sample or subject relative to the control sample or subject can be indicative of the presence of FcRn in the sample.

Another exemplary method includes: (i) administering the FcRn-binding antibody to a subject; and (iii) detecting formation of a complex between the FcRn-binding antibody and the subject. The detecting can include determining location or time of formation of the complex.

The FcRn-binding antibody can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the FcRn-binding antibody and FcRn can be detected by measuring or visualizing either the antibody bound to the FcRn or unbound antibody. Conventional detection assays can be used, e.g., an enzyme-linked immunosorbent assays (ELISA), a radioimmunoassay (RIA) or tissue immunohistochemistry. Further to labeling the FcRn-binding antibody, the presence of FcRn can be assayed in a sample by a competition immunoassay utilizing standards labeled with a detectable substance and an unlabeled FcRn-binding antibody. In one example of this assay, the biological sample, the labeled standards, and the FcRn-binding antibody are combined and the amount of labeled standard bound to the unlabeled antibody is determined. The amount of FcRn in the sample is inversely proportional to the amount of labeled standard bound to the FcRn-binding antibody.

Fluorophore and chromophore labeled antibodies can be prepared. Because antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, 1968, *Science* 162:526 and Brand, L. et al., 1972, *Annu. Rev. Biochem.* 41:843 868. The antibodies can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the antibody can be used to detect the presence or localization of the FcRn in a sample, e.g., using fluorescent microscopy (such as confocal or deconvolution microscopy).

Histological Analysis. Immunohistochemistry can be performed using the antibodies described herein. For example, the antibody can be synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation.

Of course, the antibody can be unlabeled at the time of binding. After binding and washing, the antibody is labeled in order to render it detectable.

Protein Arrays. The FcRn-binding antibody can also be immobilized on a protein array. The protein array can be used as a diagnostic tool, e.g., to screen medical samples (such as isolated cells, blood, sera, biopsies, and the like). Of course, the protein array can also include other ligands, e.g., that bind to FcRn or to other target molecules.

Methods of producing polypeptide arrays are described, e.g., in De Wildt et al., 2000, *Nat. Biotechnol.* 18:989-994; Lueking et al., 1999, *Anal. Biochem.* 270:103-111; Ge, 2000, *Nucleic Acids Res.* 28, e3, I-VII; MacBeath and Schreiber, 2000, *Science* 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the antibodies can be grown on a filter in an arrayed format. Antibody production is induced, and the expressed polypeptides are immobilized to the filter at the location of the cell. An antibody array can be contacted with a labeled target to determine the extent of binding of the target to each immobilized antibody. Information about the extent of binding at each address of the array can be stored as a profile, e.g., in a computer database. The antibody array can be produced in replicates and used to compare binding profiles, e.g., of a target and a non-target.

FACS (Fluorescence Activated Cell Sorting). The FcRn-binding antibody can be used to label cells, e.g., cells in a sample (e.g., a patient sample). The antibody is also attached (or attachable) to a fluorescent compound. The cells can then be sorted using fluorescence activated cell sorter (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

The sorter can also deflect the cell and separate cells bound by the antibody from those cells not bound by the antibody. The separated cells can be cultured and/or characterized.

In vivo Imaging. Also featured is a method for detecting the presence of a FcRn-expressing tissues in vivo. The method includes (i) administering to a subject (e.g., a patient having an autoimmune disorder) an anti-FcRn antibody, conjugated to a detectable marker; (ii) exposing the subject to a means for detecting said detectable marker to the FcRn-expressing tissues or cells. For example, the subject is imaged, e.g., by NMR or other tomographic means.

Examples of labels useful for diagnostic imaging include radiolabels such as $^{131}$I, $^{111}$In, $^{123}$I, $^{99m}$Tc, $^{32}$P, $^{125}$I, $^3$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short range radiation emitters, such as isotopes detectable by short range detector probes can also be employed. The antibody can be labeled with such reagents using known techniques. For example, see Wensel and Meares, 1983, *Radioimmunoimaging and Radioimmunotherapy*, Elsevier, New York for techniques relating to the radiolabeling of antibodies and D. Colcher et al., 1986, *Meth. Enzymol.* 121: 802 816.

A radiolabeled antibody can also be used for in vitro diagnostic tests. The specific activity of a isotopically-labeled antibody depends upon the half life, the isotopic purity of the radioactive label, and how the label is incorporated into the antibody.

Procedures for labeling polypeptides with the radioactive isotopes (such as $^{14}$C, $^3$H, $^{35}$S, $^{121}$I, $^{32}$P, $^{131}$I) are generally known. For example, tritium labeling procedures are described in U.S. Pat. No. 4,302,438. Iodinating, tritium labeling, and $^{35}$S labeling procedures, e.g., as adapted for murine monoclonal antibodies, are described, e.g., by Coding, J. W. (*Monoclonal antibodies: principles and practice: production and application of monoclonal antibodies in cell biology, biochemistry, and immunology* 2nd ed. London; Orlando: Academic Press, 1986. pp 124 126) and the references cited therein. Other procedures for iodinating polypeptides, such as antibodies, are described by Hunter and Greenwood, 1962, *Nature* 144:945, David et al., 1974, *Biochemistry* 13:1014 1021, and U.S. Pat. Nos. 3,867,517 and 4,376,110. Radiolabeling elements which are useful in imaging include $^{123}$I, $^{131}$I, $^{111}$In, and $^{99m}$Tc, for example. Procedures for iodinating antibodies are described by Greenwood, F. et al., 1963, *Biochem. J.* 89:114 123; Marchalonis, J., 1969, *Biochem. J.* 113:299 305; and Morrison, M. et al., 1971, *Immunochemistry* 289 297. Procedures for $^{99m}$Tc labeling are described by Rhodes, B. et al. in Burchiel, S. et al. (eds.), *Tumor Imaging: The Radioimmunochemical Detection of Cancer*, New York: Masson 111 123 (1982) and the references cited therein. Procedures suitable for $^{111}$In labeling antibodies are described by Hnatowich, D. J. et al., 1983, *J. Immunol. Methods*, 65:147 157, Hnatowich, D. et al., 1984, *J. Applied Radiation*, 35:554 557, and Buckley, R. G. et al., 1984, *F.E.B.S.* 166:202 204.

In the case of a radiolabeled antibody, the antibody is administered to the patient, is localized to cells bearing the antigen with which the antibody reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65 85 (Academic Press 1985). Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments is used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 mm to about 10 nM in diameter). Particles can have ferromagnetic, antiferromagnetic, or superparamagnetic properties. Particles can include, e.g., magnetite ($Fe_3O_4$), $\gamma$-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as sepharose, dextran, dextrin, starch and the like.

The FcRn-binding antibody can also be labeled with an indicating group containing of the NMR active $^{19}$F atom, or a plurality of such atoms inasmuch as (i) substantially all of naturally abundant fluorine atoms are the $^{19}$F isotope and, thus, substantially all fluorine containing compounds are NMR active; (ii) many chemically active polyfluorinated compounds such as trifluoroacetic anhydride are commercially available at relatively low cost; and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett, 1982, *Sci. Am.* 246:78 88 to locate and image tissues expressing FcRn.

The disclosure also features kits comprising an antibody that binds to FcRn and instructions for diagnostic use, e.g., the use of the FcRn-binding antibody or antigen-binding fragment thereof, to detect FcRn, in vitro, e.g., in a sample, e.g., a biopsy or cells from a patient having an autoimmune disorder, or in vivo, e.g., by imaging a subject. The kit can further contain a least one additional reagent, such as a label or additional diagnostic agent. For in vivo use the antibody can be formulated as a pharmaceutical composition.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

Example 1: DX2504 and Cysteine Mutants Thereof

The light chain of the DX-2504 anti-FcRn antibody has an unpaired cysteine in the first position of CDR3. This cysteine is adjacent to the cysteine in the FR3 that pairs with the cysteine in the FR1 of light chains. We constructed two mutants that replace the cysteine in the CDR3 with either a serine or an alanine. (See below and see also FIG. 9).
Mutants
1) 532A-X53-C02: cys to ser mutant
2) 532A-X54-B03: cys to ala mutant

```
Sequence Alignment of the Light Chains of DX-2504 (SEQ ID NO: 8), 532A-X53-C02
(SEQ ID NO: 10), and 532A-X54-B03 (SEQ ID NO: 11)
                    FR1-L                 CDR1-L          FR2-L            CDR2-L
DX-2504:       QSALTQPASVSGSPGQSITTSC  TGTGSDVGSYNLVS  WYQQHPGKAPKLMIY  GDSQRPS
532A-X53-C02   QSALTQPASVSGSPGQSITISC  TGTGSDVGSYNLVS  WYQQHPGKAPKLMIY  GDSQRPS
532A-X54-B03   QSALTQPASVSGSPGQSITTSC  TGTGSDVGSYNLVS  WYQQHPGKAPKLMIY  GDSQRPS FR3-L                            CDR3-L        FR4-L
DX-2504:       GVSNRFSGSKSGNTASLTISGLQAEDEADYYC  CSYAGSGIYV  FGTGTKVTVL
532A-X53-C02:  GVSNRFSGSKSGNTASLTISGLQAEDEADYYC  SSYAGSGIYV  FGTGTKVTVL
532A-X54-B03:  GVSNRFSGSKSGNTASLTISGLQAEDEADYYC  ASYAGSGIYV  FGTGTKVTVL
```

Size Exclusion Chromatography (SEC) Analysis of DX-2504, 532A-X53-C02 and 532-X54-B03

Antibody purity was assessed by injecting 50 µg protein over a Tosoh G3000 SWXL column equilibrated in 0.2M Sodium Phosphate, pH: 6.9 on a Waters 2695 HPLC system with UV detection. Integrated peak areas were expressed as % monomer (i.e. intact antibody), % high molecular weight aggregates (% HMW), and % low molecular weight species (% LMW) in Table 1. (See also FIG. 1).

TABLE 1

Summary of SEC Results

| Isolate | % HMWA | % Monomer | % LMW |
|---|---|---|---|
| DX-2504 | 2.71 | 96.8 | 0.5 |
| 532A-X53-C02 | 1.23 | 98.8 | NA |
| 532A-X54-B03 | 1.62 | 98.4 | NA |

SDS-PAGE Analysis of DX-2504, 532A-X53-C02 and 532-X54-B03

Antibodies were treated with 50 mM N-ethylmaleimide followed by SDS-PAGE sample buffer and heated for 10 minutes at 72° C. to block free thiol that may lead to gel artifacts. Antibody (4 µg) was loaded onto a 4-12% gradient NuPAGE gel and stained with Simply Blue Safe Stain, prior to densitometry analysis using a UVP system (Table 2). (See also FIG. 2)

TABLE 2

Summary of Densitometry Analyses
Densitometry Analysis on Non-reduced mAb Samples

| Band I.D. | DX-2504 | 532A-X54-B03 | 532A-X53-C02 |
|---|---|---|---|
| 2H/2L (Monomer) | 81.6% | 92.8% | 92.4% |
| 2H/1L | 13.8% | 6.5% | 6.8% |
| 2H | 4.5% | 0.7% | 0.9% |

Temperature Stability of DX-2504, 532A-X53-C02 and 532-X54-B03

DX-2504, 532A-X53-C02 and 532-X54-B03_samples were incubated at 37° C. for 1 month. Samples were taken at different time points for analysis using analytical SEC. Temperature stability of DX-2504 and cysteine mutants is presented based on the change in % monomer. (See FIG. 3).

pH Stability of DX-2504, 532A-X53-C02 and 532-X54-B03

DX-2504, 532A-X53-C02 and 532-X54-B03 samples were incubated in different pH conditions at room temperature for 1 month. Samples were taken at different time points for analysis using analytical SEC. pH stability of DX-2504 and cysteine mutants is presented based on the change in % monomer. (See FIG. 4).

Stability of DX-2504, 532A-X53-C02 and 532-X54-B03 at pH 8.3

Figure 5:
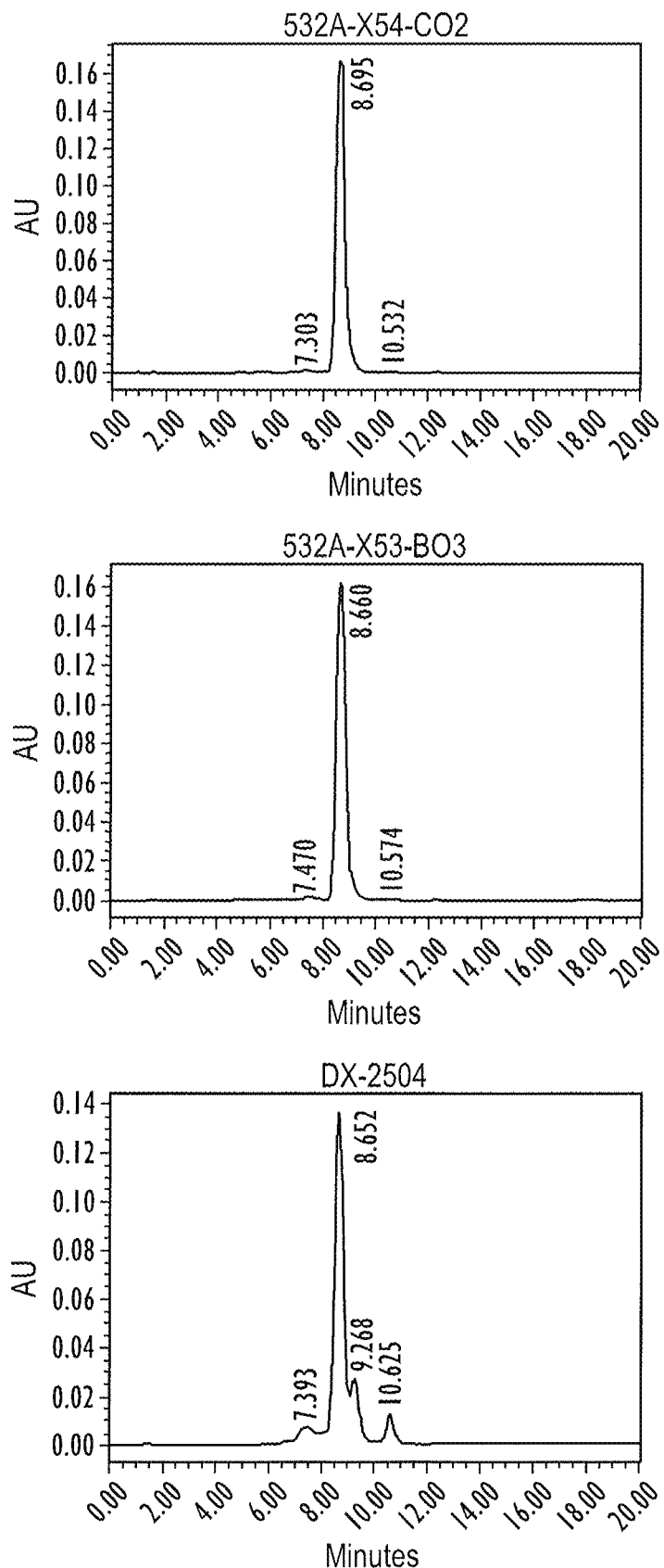
FIG. 5 shows the stability at pH 8.3 of DX-2504, 532A-X53-C02 and 532A-X54-B03.

Stability was assessed using SEC as described in the paragraph above Table 1. The SEC analysis of the antibodies at pH 8.3 is shown since it illustrates the improved stability of the cysteine mutants over DX-2504 at tested pH condition. (See FIG. 5).

Thiol Titration with DTNB

The presence of free cysteine thiols in the purified antibody solutions was assessed by reacting 10 µM antibody with 10 mM DTNB (Ellman's reagent, or 5,5'-dithio-bis (2-nitrobenzoic acid)) in the presence or absence of the denaturation reagent 6 M guanidine hydrochloride for 0.5 hours at 37° C. before reading the absorbance of the reaction at 412 nm ($\varepsilon=14,100$ M$^{-1}$ cm$^{-1}$). The concentration of thiol was divided by the concentration of antibody to obtain the mol thiol/mol of mAb. (See Table 3 below).

TABLE 3

Summary of Thiol Titration Data
DTNB Assay - 10 µM mAb

| Sample I.D | Free Thiol/mol mAb Not Denatured | Free Thiol/mol mAb Denatured |
|---|---|---|
| DX-2504 | 0.06 | 0.62 |
| 532A-X54-B03 | 0.05 | 0.31 |
| 532A-X53-C02 | 0.05 | 0.25 |

Stability of DX-2504, 532A-X53-C02 and 532-X54-B03 Towards Chemical Denaturation.

Figure 6:
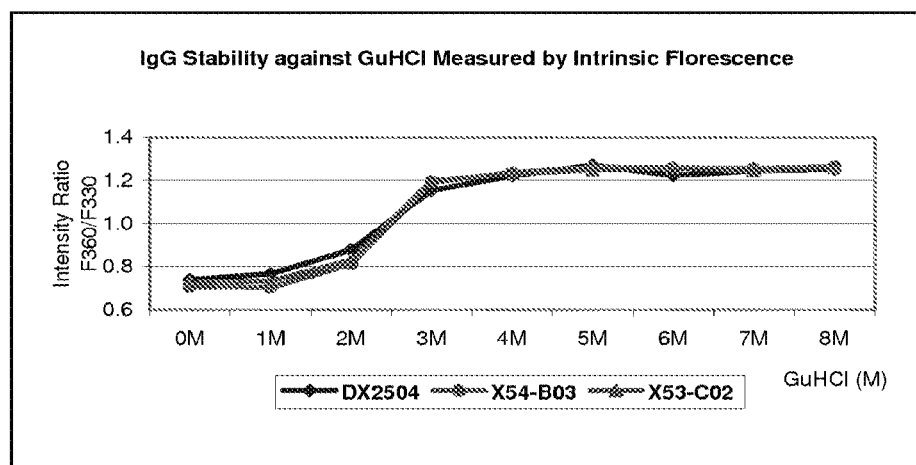
FIG. 6 shows the stability towards chemical denaturation of DX-2504, 532A-X53-C02 and 532A-X54-B03.

Protein stability of DX-2504 and cysteine mutants was measured by monitoring intrinsic fluorescence as a function of chemical denaturant guanidine hydrochloride (GuHCl) concentration. 1 mg/ml of each antibody product were prepared with different concentration of GuHCl 1 to 8M. Fluorescence was measured and the intensity ratio of 360/330 as a function of GuHCl concentration is plotted. Cysteine mutants show better stability for structural conformation changes against denaturant reagent. (See FIG. 6).

Surface Plasmon Resonance (SPR or Biacore) Kinetic Analysis of the Interaction of hFcRn with Immobilized DX-2504, 532A-X53-C02 and 532-X54-B03.

SPR measurements were performed using a Biacore 3000. DX-2504, 532A-X53-C02 and 532-X54-B03 were immobilized by amine coupling on CM5 sensor chips at immobilization densities of ~220 RU. To measure the kinetic parameters of DX-2504 interaction with FcRn analyte, two-fold serial dilutions prepared from 100 nM of FcRn were injected in duplicate for 5 min at 50 l/min with a 15 minute dissociation phase. The sensor chip surface was regenerated with a 30 sec pulse of 10 mM glycine pH 1.5 at a flow rate of 75 l/min followed by a 15 second pulse of buffer. Measurements were performed at 25° C. using HBS-P as the running buffer. The reference flow cell was activated and blocked in a mock amine coupling reaction. The data was fit to a 1:1 binding model using Biaevalution v.4.1 software. (See Table 4, FIG. 7 and FIG. 8).

TABLE 4

Summary of SPR Results

| | Sample | $k_a$ (M$^{-1}$s$^{-1}$) | $k_d$ (s$^{-1}$) | $K_D$ (nM) |
|---|---|---|---|---|
| pH 6.0 | 532A-X54-B03 | $1.7 \times 10^5$ | $3.1 \times 10^{-4}$ | 1.8 |
| | 532A-X53-C02 | $3.1 \times 10^5$ | $4.3 \times 10^{-4}$ | 1.4 |
| | DX-2504 lot 040709 | $2.4 \times 10^5$ | $3.5 \times 10^{-4}$ | 1.5 |
| pH 7.5 | 532A-X54-B03 | $1.1 \times 10^5$ | $2.2 \times 10^{-4}$ | 2.0 |
| | 532A-X53-C02 | $1.9 \times 10^5$ | $3.2 \times 10^{-4}$ | 1.7 |
| | DX-2504 lot 040709 | $1.5 \times 10^5$ | $2.8 \times 10^{-4}$ | 1.9 |

Example 2: Deletion Mutant of DX-2504

The heavy chain of the DX-2504 anti-FcRn antibody contains a lysine at the last position (C-terminus) in the heavy chain. Mutant DX-2507 (light chain SEQ ID NO: 18, heavy chain SEQ ID NO:19) contains the same light chain as that of DX-2504 and a mutated heavy chain, which was constructed by deleting the C-terminal lysine residue in the heavy chain of DX-2504. A sequence alignment between the C-terminal fragment of DX-2504 heavy chain (SEQ ID NO:20) and that of DX-2507 heavy chain (SEQ ID NO:21) is shown below:

```
DX 2504:
SDGSFFLYSKLTVDKSRWQQGNVFSCSVMHEALHNHYTQKSLSLSPGK

DX 2507:
SDGSFFLYSKLTVDKSRWQQGNVFSCSVMHEALHNHYTQKSLSLSPG
```

Pharmacologic Profile and Toxicokinetic Profile of DX-2504 and DX-2507 in Cynomolgus Monkeys Six naïve female cynomolgus monkeys were assigned to 2 dose groups each consisting of 3 animals. Table 5 provides a summary of the study design. All animals were dosed 20 mg/kg of the test antibody via subcutaneous (SC) injection once on Study Day 0 and Study Day 7. Group 1 animals were administered DX-2504 and Group 2 animals were administered DX-2507. Blood was collected from all animals at the following time points: Day 0 (prior to dosing and 2 and 12 hours post-dose), Days 1, 2, 3, 4, 5, 6, Day 7 (prior to dosing and 2 and 12 hours post-dose), Days 8, 9, 10, 11, 12, 13, 14, 17, 21, 24, 28, 31 and 35. Serum samples for toxicokinetics of DX-2504 and DX-2507 were analyzed using a qualified ELISA method (DRD-910-029). Total cynomolgus monkey IgG levels were analyzed using a qualified ELISA method (DRD_910-033).

TABLE 5

Study Design

| Group | # of Animals | Test Ab | Dose level (mg/kg/dose) | Route | Dose Concentration (mg/mL) | Dose volume (mL/kg) |
|---|---|---|---|---|---|---|
| 1 | 3 | DX-2504 | 20 | SC | 18.2 | 1.10 |
| 2 | 3 | DX-2507 | 20 | SC | 35.6 | 0.56 |

DX-2504 serum concentrations were detected from 2 hours post-dose on Day 0 through Day 11 in 2 animals and Day 13 in one animal. DX-2507 serum concentrations were detected from 2 hours post-dose on Day 0 through Day 11, Day 12, and Day 17 in individual animals. The results thus obtained show that the serum concentrations of DX-2507 were much higher than those of DX-2504 in the test animals, indicating that DX-2507 was more stable in vivo than DX-2504. FIG. 13.

Cynomolgus monkey IgG levels were reduced following administration of both DX-2504 and DX-2507 (FIG. 14). Following administration of the Day 0 dose, mean total IgG levels were reduced to 42% and 33% of pre-dose baseline levels in the DX-2504 and DX-2507 dose groups, respectively. Prior to the Day 7 dose, mean total IgG levels increased to 45% and 37% of predose baseline levels in the same treatment groups. Following administration of the Day 7 dose, mean total IgG levels were reduced to 42% of predose baseline values in the DX-2504 group and to 30% of predose baseline values in the DX-2507 group. Total IgG levels retuned to predose baseline values on Day 13 in the DX-2504-treated animals and on Day 21 in the DX-2507-treated animals.

The mean toxicokinetic parameters for DX-2504 and DX-2507 are summarized in Table 6.

TABLE 6

Mean (SD) Toxicokinetic parameters

| Test Ab | Study Day | $C_{max}$ (ug/mL) | $AUC_{last}$ (d*ug/mL) | CL/F (mL/d/Kg) | Vz/F (mL/Kg) | t1/2 (d) |
|---|---|---|---|---|---|---|
| DX-2504 | 0 | 51.9 (25.8) | 70.8 (32.2) | 341.0 (204.5) | 879.1 (407.0) | 1.9 (0.2) |
| | 7* | 32.0 (15.7) | 47.5 (20.0) | 492.3 (264.0) | 312.4 (252.0) | 0.4 (0.1) |
| DX-2507 | 0 | 75.3 (19.7) | 135.6 (29.4) | 152.0 (31.8) | 74.1 (35.0) | 0.3 (0.1) |
| | 7* | 71.6 (4.7) | 120.3 (3.2) | 166.3 (4.3) | 73.6 (24.8) | 0.3 (0.1) |

*Serum concentration profiles were corrected for predose (Day 7) baseline concentrations The toxicokinetic parameters for both DX-2504 and DX-2507 were substantially consistent on days 0 and 7. The overall exposure of DX-2507 was greater than that observed for DX-2504. The mean maximum concentration ($C_{max}$) and plasma/serum concentration-time curve ($AUC_{last}$) values for DX-2507 on either Day 0 or Day 7 were between 2 to 3-fold greater than the corresponding values calculated for DX-2504. In addition, the corresponding mean apparent clearance (CL/F) and distribution volume (Vz/F) values for DX-2504 were between 2 to 12-fold greater than DX-2507.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety, particularly for the use or subject matter referenced herein.

What is claimed is:

1. An isolated antibody comprising:

a heavy chain (HC) that comprises a HC variable region ($V_H$) and a HC constant region ($C_H$), wherein the $V_H$ comprises a complementarity determining region (HC CDR) 1, a HC CDR2, and a HC CDR3, wherein the HC CDR3 has the amino acid sequence LAIGDSY (SEQ ID NO: 24), the $C_H$ has a deletion at the position corresponding to the C-terminal lysine residue of SEQ ID NO: 17, and the $V_H$ comprises an amino acid sequence having at least 95% homology with SEQ ID NO: 9; and a light chain (LC) that comprises a LC variable region ($V_L$) and a LC constant region ($C_L$), wherein the $V_L$ comprises a complementarity determining region (LC CDR) 1, a LC CDR2, and a LC CDR3, wherein the LC CDR3 has the amino acid sequence SSYAGSGIYV (SEQ ID NO: 12) and wherein the $V_L$ comprises an amino acid sequence having at least 95% homology with SEQ ID NO: 10;

wherein the antibody binds an FcRn.

2. The isolated antibody of claim 1, wherein the antibody comprises:

a $V_H$ CDR1 and a $V_H$ CDR2 that, in combination, have at least 85% homology with EYAMG (SEQ ID NO: 22) and SIGSSGGQTKYADSVKG (SEQ ID NO: 23), respectively, and a $V_L$ CDR1 and a $V_L$ CDR2 that, in combination, have at least 85% homology with TGTGSDVGSYNLVS (SEQ ID NO: 14) and GDSQRPS (SEQ ID NO: 15), respectively.

3. The isolated antibody of claim 2, wherein the antibody comprises:

a $V_H$ CDR1 and a $V_H$ CDR2 that, in combination, have at least 90% homology with EYAMG (SEQ ID NO: 22) and SIGSSGGQTKYADSVKG (SEQ ID NO: 23), respectively; and a $V_L$ CDR1 and a $V_L$ CDR2 that, in combination, have at least 90% homology with TGTGSDVSYNLVS (SEQ ID NO: 14) and GDSQRPS (SEQ ID NO: 15), respectively.

4. The isolated antibody of claim 3, wherein the antibody comprises:

a $V_H$ CDR1 and a $V_H$ CDR2 that, in combination, have at least 95% homology with EYAMG (SEQ ID NO: 22) and SIGSSGGQTKYADSVKG (SEQ ID NO: 23), respectively; and a $V_L$ CDR1 and a $V_L$ CDR2 that, in combination, have at least 95% homology with TGTGSDVSYNLVS (SEQ ID NO: 14) and GDSQRPS (SEQ ID NO: 15), respectively.

5. The isolated antibody of claim 1, wherein the antibody comprises one or more mutations within the framework regions of SEQ ID NO: 9 and/or SEQ ID NO: 10.

6. The isolated antibody of claim 1, wherein the antibody is human or humanized.

7. The isolated antibody of claim 1, wherein the antibody is a full-length antibody.

8. The isolated antibody of claim 1, wherein the antibody is an antigen-binding fragment.

9. A pharmaceutical composition comprising the isolated antibody of claim 1 and a pharmaceutically acceptable carrier.

10. An isolated antibody comprising:
- a heavy chain (HC) that comprises a HC variable region ($V_H$) and a HC constant region ($C_H$), wherein the $V_H$ comprises a complementarity determining region (HC CDR) 1, a HC CDR2, and a HC CDR3, wherein the HC CDR3 has the amino acid LAIGDSY (SEQ ID NO: 24), the $C_H$ has a deletion at the position corresponding to the C-terminal lysine residue of SEQ ID NO: 17, and the $V_H$ comprises an amino acid sequence having up to 5 amino acid substitutions compared to SEQ ID NO: 9; and
- a light chain (LC) that comprises a LC variable region ($V_L$) and a LC constant region ($C_L$), wherein the $V_L$ comprises a complementarity determining region (LC CDR) 1, a LC CDR2, and a LC CDR3, wherein the LC CDR3 has the amino acid sequence SSYAGSGIYV (SEQ ID NO: 12), and wherein the $V_L$ comprises an amino acid sequence having up to 5 amino acid substitutions compared to SEQ ID NO: 10;
wherein the antibody binds an FcRn.

11. The isolated antibody of claim 10, wherein the antibody comprises:
- a $V_H$ CDR1 and a $V_H$ CDR2 that collectively have up to 5 amino acid substitutions compared to EYAMG (SEQ ID NO: 22) and SIGSSGGQTKYADSVKG (SEQ ID NO: 23), respectively, and
- a $V_L$ CDR1 and a $V_L$ CDR2 that collectively have up to 5 amino acid substitutions compared to TGTGSDVGSYNLVS (SEQ ID NO: 14) and GDSQRPS (SEQ ID NO: 15), respectively.

12. The isolated antibody of claim 10, wherein the antibody contains one or more mutations within the framework regions of SEQ ID NO: 9 and/or SEQ ID NO: 10.

13. The isolated antibody of claim 10, wherein the antibody is human or humanized.

14. The isolated antibody of claim 10, wherein the antibody is a full-length antibody.

15. The isolated antibody of claim 10, wherein the antibody is an antigen-binding fragment.

16. A pharmaceutical composition comprising the isolated antibody of claim 10 and a pharmaceutically acceptable carrier.

* * * * *